US008916365B2

(12) United States Patent  
Macool et al.

(10) Patent No.: US 8,916,365 B2
(45) Date of Patent: Dec. 23, 2014

(54) EXPRESSION OF CYTOSOLIC MALIC ENZYME IN TRANSGENIC YARROWIA TO INCREASE LIPID PRODUCTION

(71) Applicant: E I du Pont de Nemours and Company, Wilmington, DE (US)

(72) Inventors: Daniel Joseph Macool, Rutledge, PA (US); Zhixiong Xue, Chadds Ford, PA (US); Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/804,348

(22) Filed: Mar. 14, 2013

(65) Prior Publication Data

US 2013/0260427 A1  Oct. 3, 2013

Related U.S. Application Data

(60) Provisional application No. 61/619,574, filed on Apr. 3, 2012.

(51) Int. Cl.
| | | |
|---|---|---|
| *C12P 7/64* | (2006.01) | |
| *C12N 9/00* | (2006.01) | |
| *C12N 9/02* | (2006.01) | |
| *C12N 1/20* | (2006.01) | |
| *C07H 21/04* | (2006.01) | |
| *C12N 15/80* | (2006.01) | |

(52) U.S. Cl.
CPC ......... *C12N 15/80* (2013.01); *C12Y 101/01038* (2013.01); *C12Y 101/0104* (2013.01); *C21N 9/0006* (2013.01); *C12P 7/6472* (2013.01); *C12Y 101/01039* (2013.01)
USPC ........ 435/134; 435/183; 435/189; 435/252.3; 435/320.1; 536/23.2

(58) Field of Classification Search
None
See application file for complete search history.

(56) References Cited

U.S. PATENT DOCUMENTS

| | | |
|---|---|---|
| 7,408,052 B2 | 8/2008 | Cheikh et al. |
| 7,851,199 B2 | 12/2010 | Bailey et al. |
| 2010/0305341 A1 | 12/2010 | Bailey et al. |
| 2011/0021843 A1 | 1/2011 | Bailey et al. |
| 2011/0039299 A1 | 2/2011 | Bailey et al. |
| 2011/0039327 A1 | 2/2011 | Winkler et al. |
| 2011/0223641 A1 | 9/2011 | Stephanopoulos et al. |

FOREIGN PATENT DOCUMENTS

WO    2007120423 A2    10/2007

OTHER PUBLICATIONS

Accession Q6C5F0. Aug. 16, 2004.*
Y. Abe et al., Structural Basis of Presequence Recognition by the Mitochondrial Protein Import Receptor TOM20, Cell, vol. 100 (2000), pp. 551-560.
A. Beopoulos, Ingenierie Genetique De La Levure Oleagineuse *Yarrowia lipolytica* Pour La Production De Lipides, L'Institute Des Sciences Et Industries Du Vivant Et De L'Enrivonment (Agro Paris Tech), Specialite: Biotechnologie, Presented April 8, 2010, pp. 1-184 (Translation Currently Unavailable).
A. Beopoulous et al., An Overview of Lipid Metabolism in Yeasts and Its Impact on Biotechnological Processes, Applied Microbiol. Biotechnol., vol. 90 (2011), pp. 1193-1206.
A. Beopoulos et al., *Yarrowia lipolytica* as a Model for Bio-Oil Production, Progress in Lipid Research, Vol. 48 (2009), pp. 375-387.
Brix et al., Differntial Recognition of Preproteins by the Purified Cytosolic Domains of the Mitochondrial Import Receptors TOM20, TOM22 and TOM70, The Journal of Biological Chemistry, vol. 272, No. 33 (1997), pp. 20730-20735.
Claros et al., Computational Method to Predict Mitochondrially Imported Proteins and Theier Targeting Sequences, Eur. J. Biochem., vol. 241 (1996), pp. 779-786.
Dos Santos et al., Manipulation of Malic Enzyme in *Saccharomyces cerevisiae* for Increasing NADPH Production Capacity Aerobically in Different Cellular Compartments, Metabolic Engineering, vol. 6 (2004), pp. 352-363.
Emanuelsson et al., Predicting Subcellular Localization of Proteins Based on Their N-Terminal Amino Acid Sequence, J. Mol. Biol. Vol. 300 (2000), pp. 1005-1016.
Guda et al., Target: A New Method for Predicting Protein Subcellular Localization in Eukaroytes, Bioinformatics, Original Paper, vol. 21, No. 21 (2005), pp. 3963-3969.
Morin et al., Transcriptomoic Analyses During the Transition From Biomass Production to Lipid Accumulation in the Oleaginous Yeast *Yarrowia lipolytica*, PLOS ONE, vol. 6, Issue 11, E27966 (2011), pp. 1-13.
Ratledge, Regulation of Lipid Acumulation in Oleaginous Micro-Organisms, Regulation of Fatty Acid Synthesis, Biochemical Society Transcripts, vol. 30 (200), pp. 1047-1050.
Roise et al., Mitochondial Presequences, Journal of Biological Chemistry, vol. 263, No. 10 (1988), pp. 4509-4511.
Small et al., Predotar: A Tool for Rapidly Screening Proteomes for N-Terminal Targeting Sequences, Proteomics, vol. 4 (2004), pp. 1581-1590.
Sokolov et al., Subcellular Location of Enzymes Mediating Glucose Metabolism in Various Groups of Yeast, Biochemistry Moscow, vol. 60, No. 10 (1995), pp. 1325-1331.
Wynn et al., The Role of Malic Enzyme in the Regulation of Lipid Accumulation in Filamentous Fungi, Microbiology, vol. 145 (1999), pp. 1911-1917.
Wynn et al., Malic Enzyme Is a Mjaor Source of NADPH for Lipid Accumulation by *Aspergillus nidulans*, Microbiology, vol. 143 (1997), pp. 253-257.
Zelle et al., Anaplerotic Role for Cytosolic Malic Enzyme in Engineering *Saccharomyces cerevisiae* Strains, Applied and Environmental Microbiology, vol. 77, No. 3 (2011), pp. 732-738.
Zhang et al., Malic Enzyme: The Controlling Activity for Lipid Production, Overexpression of Malic Enzyme in *Mucor circinelloides* Leads to a 2.5-Fold Increase in Lipid Accumulation, Microbiology, vol. 153 (2007), pp. 2013-2025.
International Search Report, PCT International Application PCT/US2013/031839, Mailed June 4, 2013.

* cited by examiner

*Primary Examiner* — Christian Fronda

(57) ABSTRACT

Transgenic *Yarrowia* species are disclosed herein that comprise a polynucleotide encoding a cytosolic malic enzyme, a lipid content that is at least about 35% by weight of the dry cell weight of the *Yarrowia* species, and an engineered polyunsaturated fatty acid (PUFA) biosynthetic pathway, wherein overexpression of the cytosolic malic enzyme increases lipid content.

19 Claims, 8 Drawing Sheets

Figure 2:
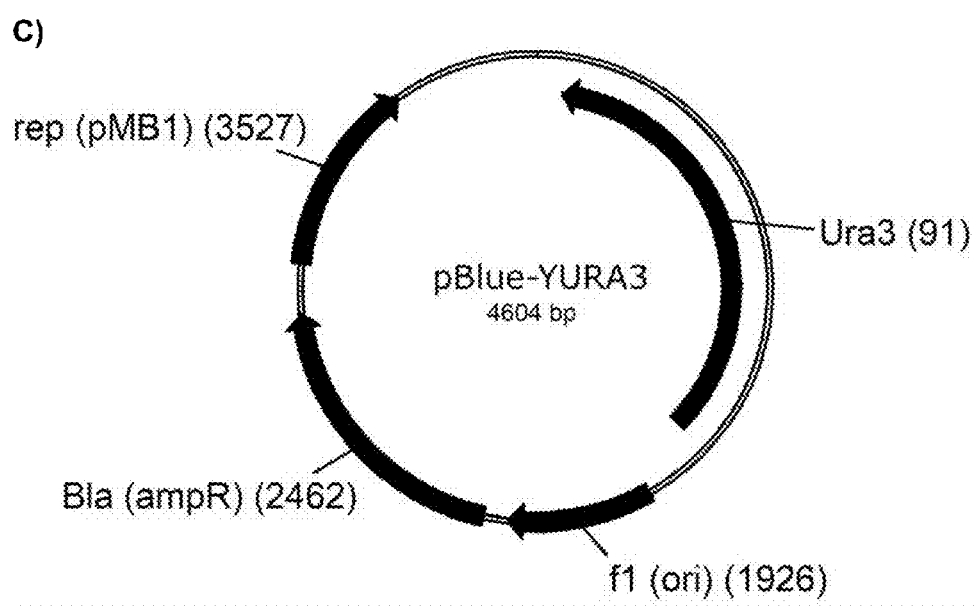

```
                              1                                                50
ScME [SEQ ID NO:2]    (1)   MLRTRLSVSVAARSQLTRSLTASRTAPLRRWPIQQSRLYSSNTRSHKATT
SpME [SEQ ID NO:3]    (1)   -------------------------------------------------
YlME [SEQ ID NO:1]    (1)   ---------------------------------MLRLRTMRPTQISVRAALG 51                                               100
ScME [SEQ ID NO:2]   (51)   TRENTFQKPYSDEEVTKTPVGSRARKIFEAPHPHATRLTVEGAIECPLES
SpME [SEQ ID NO:3]    (1)   -----------------------------MPAGTKEQIECPLKG
YlME [SEQ ID NO:1]   (20)   PTAAARNMSSSSPSSFEYSSYVKGTREIGHRKAPTTRLSVEGPIYVGFDG 101                                              150
ScME [SEQ ID NO:2]  (101)   FQLLNSPLFNKGSAFTQEEREAFNLEALLPPQVNTLDEQLERSYKQLCYL
SpME [SEQ ID NO:3]   (16)   VTLLNSPRYNKDTAFTPEERQKFEISSRLPPIVETLQQQVDRCYDQYKAI
YlME [SEQ ID NO:1]   (70)   IRLLNLPHLNKGSGFPLNERREFRLSGLLPSAEATLEEQVDRAYQQFKKC 151                                              200
ScME [SEQ ID NO:2]  (151)   -KTPLAKNDFMTSLRVQNKVLYFALTRRHIKELVPIIYTPTEGDAIAAYS
SpME [SEQ ID NO:3]   (66)   GDEFLQKNLYLSQLSVTNQFLFYALISQHLIEMIPIIYTPTEGDAIKQFS
YlME [SEQ ID NO:1]  (120)   -GTPLAKNGFCTSLKFQNEVLYYALLLKHVKEVFPIIYTPTQGEAIEQYS 201                                              250
ScME [SEQ ID NO:2]  (200)   HRFRKPEGVFLDITEPDS--IECRLATYGGDKDVDYIVVSDSEGILGIGD
SpME [SEQ ID NO:3]  (116)   DIYRYPEGCYLDIDHNDLSYIKQQLSEFGKSDSVEYIIITDSEGILGIGD
YlME [SEQ ID NO:1]  (169)   RLFRRPEGCFLDITSPYD--VEERLGAFGDHDDIDYIVVTDSEGILGIGD 251                                              300
ScME [SEQ ID NO:2]  (248)   QGIGGVRIAISKLALMTLCGGIHPGRVLPVCLDVGTNNKKLARDELYMGN
SpME [SEQ ID NO:3]  (166)   QGVGGVLISVAKGHLMTLCAGLDPNRFLPIVLDVGTNNETHRKNHQYMGL
YlME [SEQ ID NO:1]  (217)   QGVGGIGISIAKLALMTLCAGVNPSRVIPVVLDTGTNNQELLHDPLYLGR 301                                              350
ScME [SEQ ID NO:2]  (298)   KFSRIRGKQYDDFLEKFIKAVKKVYPSAVLHFEDFGVKNARRLLEKYRYE
SpME [SEQ ID NO:3]  (216)   RKDRVRGEQYDSFLDNVIKAIREVFPEAFIHFEDFGLANAKRILDHYRPD
YlME [SEQ ID NO:1]  (267)   RMPRVRGKQYDDFIDNFVQSARRLYPKAVIHFEDFGLANAHKILDKYRPE 351                                              400
ScME [SEQ ID NO:2]  (348)   LPSFNDDIQGTGAVVMASLIAALKHTNRDLKDTRVLIYGAGSAGLGIADQ
SpME [SEQ ID NO:3]  (266)   IACFNDDIQGTGAVALAAIIGALEVTKSPLTEQRIMIFGAGTAGVGIANQ
YlME [SEQ ID NO:1]  (317)   IPCFNDDIQGTGAVTLASITAALKVLGKNITDTRILVYGAGSAGMGIAEQ 401                                              450
ScME [SEQ ID NO:2]  (398)   IVNHMVTHGVDKEEARKKIFLMDRRGLILQSY-EANSTPAQHVYAKSDAE
SpME [SEQ ID NO:3]  (316)   IVAGMVTDGLSLDKARGNLFMIDRCGLLLERH-AKIATDGQKPFLKKDSD
YlME [SEQ ID NO:1]  (367)   VYDNLVAQGLDDKTARQNIFLMDRPGLLTTALTDEQMSDVQKPFAKDKAN 451                                              500
ScME [SEQ ID NO:2]  (447)   WAGINT--RSLHDVVENVKPTCLVGCSTQAGAFTQDVVEEMHKHNPRPII
SpME [SEQ ID NO:3]  (365)   FKEVPSGDINLESAIALVKPTILLGCSGQPGKFTEKAIREMSKHVERPII
YlME [SEQ ID NO:1]  (417)   YEGVDT--KTLEHVVAAVKPHILIGCSTQPGAFNEKVVKEMLKHTPRPII
```

Figure 1

```
                           501                                    550
ScME [SEQ ID NO:2]  (495)  FPLSNPTRLHEAVPADLMKWTNNNALVATGSPFPPVDG----YRISENNN
SpME [SEQ ID NO:3]  (415)  FPISNPTTLMEAKPDQIDKWSDGKALIATGSPLPPLNRNGKKYVISQCNN
Y1ME [SEQ ID NO:1]  (465)  LPLSNPTRLHEAVPADLYKWTDGKALVATGSPFDPVNG----KETSENNN 551                                    600
ScME [SEQ ID NO:2]  (541)  CYSFPGIGLGAVLSRATTITDKMISAAVDQLAELSPLREGDSRPGLLPGL
SpME [SEQ ID NO:3]  (465)  ALLYPALGVACVLSRCKLLSDGMLKAASDALATVPRSLFAAD-EALLPDL
Y1ME [SEQ ID NO:1]  (511)  CFVFPGIGLGAILSRSKLITNTMIAAAIECLAEQAPILKNHD-EGVLPDV 601                                    650
ScME [SEQ ID NO:2]  (591)  DTITNTSARLATAVILQALEEGTARIEQEQVPGGAPGETVKVPRDFDECL
SpME [SEQ ID NO:3]  (514)  NNAREISRHIVFAVLKQAVSEGMS--------------TVDLPKDDAKLK
Y1ME [SEQ ID NO:1]  (560)  ALIQIISARVATAVVLQAKAEGLATVEEELKPG--TKEHVQIPDNFDECL 651              679
ScME [SEQ ID NO:2]  (641)  QWVKAQMWEPVYRPMIKVQHDPSVHTNQL
SpME [SEQ ID NO:3]  (550)  EWIIEREWNPEYKPFV-------------
Y1ME [SEQ ID NO:1]  (608)  AWVETQMWRPVYRPLIHVRDYD-------
```

Figure 1 (cont.)

A)
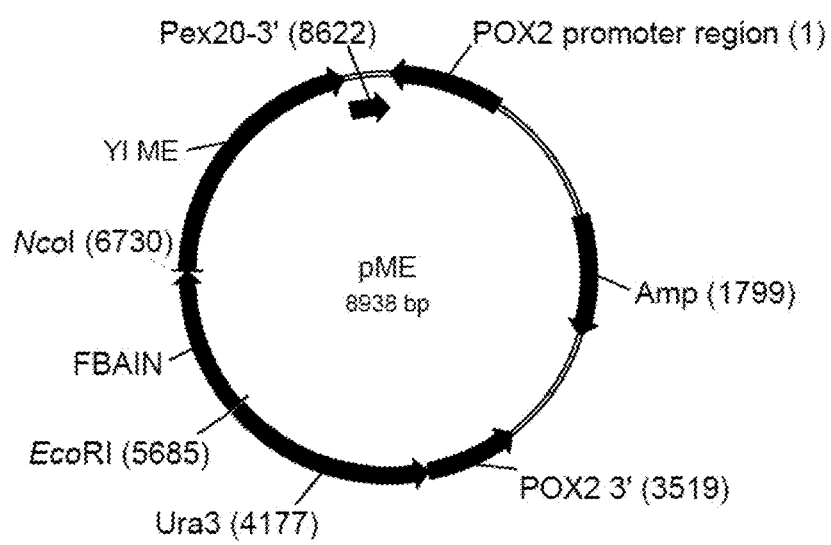
B)
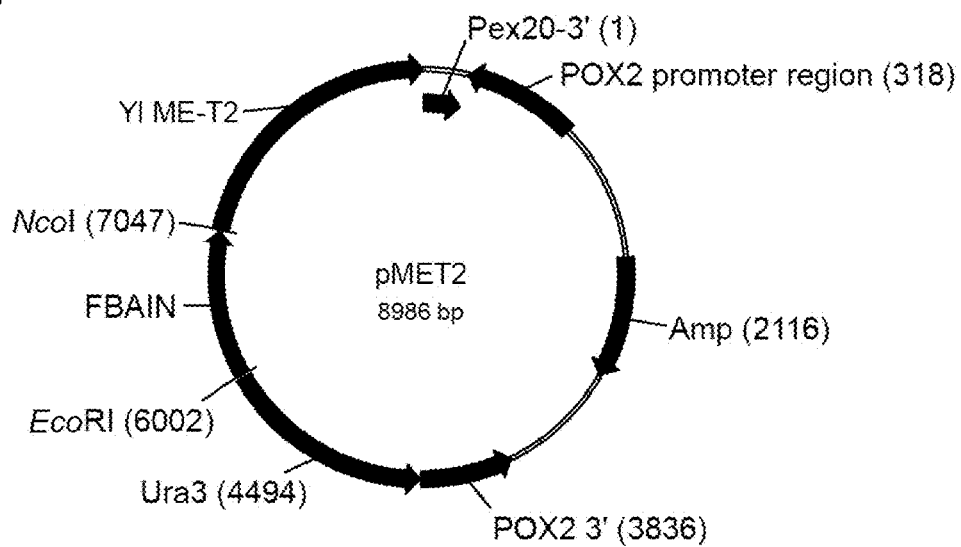
Figure 2

```
                                    1                                              50
Translation of Y1ME-T2    (1)  --------------------------------------------------
   Translation of Y1ME    (1)  MVRLRTMRPTQTSVRAALGPTAAARNMSSSSPSSFEYSSYVKGTREIGHR 51                                            100
Translation of Y1ME-T2    (1)  -MATTRLSVEGPIYVGFDGIRLLNLPHLNKGSGFPLNERREFRLSGLLPS
   Translation of Y1ME   (51)  KAPTTRLSVEGPIYVGFDGIRLLNLPHLNKGSGFPLNERREFRLSGLLPS 101                                            150
Translation of Y1ME-T2   (50)  AEATLEEQVDRAYQQFKKCGTPLAKNGFCTSLKFQNEVLYYALLLKHVKE
   Translation of Y1ME  (101)  AEATLEEQVDRAYQQFKKCGTPLAKNGFCTSLKFQNEVLYYALLLKHVKE 151                                            200
Translation of Y1ME-T2  (100)  VFPIIYTPTQGEAIEQYSRLFRRPEGCFLDITSPYDVEERLGAFGDHDDI
   Translation of Y1ME  (151)  VFPIIYTPTQGEAIEQYSRLFRRPEGCFLDITSPYDVEERLGAFGDHDDI 201                                            250
Translation of Y1ME-T2  (150)  DYIVVTDSEGILGIGDQGVGGIGISIAKLALMTLCAGVNPSRVIPVVLDT
   Translation of Y1ME  (201)  DYIVVTDSEGILGIGDQGVGGIGISIAKLALMTLCAGVNPSRVIPVVLDT 251                                            300
Translation of Y1ME-T2  (200)  GTNNQELLHDPLYLGRRMPRVRGKQYDDFIDNFVQSARRLYPKAVIHFED
   Translation of Y1ME  (251)  GTNNQELLHDPLYLGRRMPRVRGKQYDDFIDNFVQSARRLYPKAVIHFED 301                                            350
Translation of Y1ME-T2  (250)  FGLANAHKILDKYRPEIPCFNDDIQGTGAVTLASITAALKVLGKNITDTR
   Translation of Y1ME  (301)  FGLANAHKILDKYRPEIPCFNDDIQGTGAVTLASITAALKVLGKNITDTR 351                                            400
Translation of Y1ME-T2  (300)  ILVYGAGSAGMGIAEQVYDNLVAQGLDDKTARQNIFLMDRPGLLTTALTD
   Translation of Y1ME  (351)  ILVYGAGSAGMGIAEQVYDNLVAQGLDDKTARQNIFLMDRPGLLTTALTD 401                                            450
Translation of Y1ME-T2  (350)  EQMSDVQKPFAKDKANYEGVDTKTLEHVVAAVKPHILIGCSTQPGAFNEK
   Translation of Y1ME  (401)  EQMSDVQKPFAKDKANYEGVDTKTLEHVVAAVKPHILIGCSTQPGAFNEK 451                                            500
Translation of Y1ME-T2  (400)  VVKEMLKHTPRPIILPLSNPTRLHEAVPADLYKWTDGKALVATGSPFDPV
   Translation of Y1ME  (451)  VVKEMLKHTPRPIILPLSNPTRLHEAVPADLYKWTDGKALVATGSPFDPV 501                                            550
Translation of Y1ME-T2  (450)  NGKETSENNNCFVFPGIGLGAILSRSKLITNTMIAAAIECLAEQAPILKN
   Translation of Y1ME  (501)  NGKETSENNNCFVFPGIGLGAILSRSKLITNTMIAAAIECLAEQAPILKN 551                                            600
Translation of Y1ME-T2  (500)  HDEGVLPDVALIQIISARVATAVVLQAKAEGLATVEEELKPGTKEHVQIP
   Translation of Y1ME  (551)  HDEGVLPDVALIQIISARVATAVVLQAKAEGLATVEEELKPGTKEHVQIP 601          630
Translation of Y1ME-T2  (550)  DNFDECLAWVETQMWRPVYRPLIHVRDYD-    (SEQ ID NO:5)
   Translation of Y1ME  (601)  DNFDECLAWVETQMWRPVYRPLIHVRDYD-    (SEQ ID NO:7)
```

Figure 3

EXPRESSION OF CYTOSOLIC MALIC ENZYME IN TRANSGENIC *YARROWIA* TO INCREASE LIPID PRODUCTION

This application claims the benefit of U.S. Provisional Application No. 61/619,574, filed Apr. 3, 2012, which is incorporated herein by reference in its entirety.

FIELD OF THE INVENTION

This invention is in the field of biotechnology. More specifically, this invention pertains to transgenic *Yarrowia* species overexpressing cytosolic malic enzyme in order to increase lipid content.

BACKGROUND OF THE INVENTION

Research has been directed to understanding lipid and fatty acid (FA) biosynthetic pathways, and genetic engineering has been used to introduce these biosynthetic pathways into host organisms. For example, a variety of different hosts including plants, algae, fungi, stramenopiles and yeast are being investigated as means for commercial polyunsaturated fatty acid (PUFA) production. Genetic engineering has demonstrated that the natural abilities of some hosts, even those natively limited to linoleic acid (LA, 18:2 omega-6) or alpha-linolenic acid (ALA, 18:3 omega-3) fatty acid production, can be substantially altered to result in high-level production of various long-chain omega-3/omega-6 PUFAs.

Although the literature reports a number of recent examples whereby various portions of the omega-3/omega-6 PUFA biosynthetic pathway responsible for EPA production have been introduced into plants and non-oleaginous yeast, significant efforts have focused on the use of the oleaginous yeast, *Yarrowia lipolytica* (U.S. Pat. Nos. 7,238,482; 7,932,077; U.S. Pat. Appl. Publ. No. 2009-0093543-A1; U.S. Pat. Appl. Publ. No. 2010-0317072-A1). Oleaginous yeast are defined as those yeast that are naturally capable of oil synthesis and accumulation, wherein oil accumulation is at least 25% of the cellular dry weight, or those yeast genetically engineered such that they become capable of oil synthesis and accumulation, wherein oil accumulation is at least 25% of the cellular dry weight.

Still there remains considerable interest in increasing lipid accumulation in fungi. Expression of malic enzyme in the cytosol in *Saccharomyces cerevisiae* has been shown to increase NADPH production (2004, dos Santos et al., *Metabol. Engineering* 6:352-363). Given the role of NADPH as a reducing agent in fatty acid synthesis, malic enzyme has been investigated as a possible factor for altering lipid production. Zhang et al. (2007, *Microbiology* 153:2013-2025) have found that overexpression of malic enzyme in wild type *Mucor circinelloides* leads to a 2.5-fold increase in lipid accumulation. Consistent with this finding, studies have shown that malic enzyme expression in *M. circinelloides* and *Mortierella alpina* is correlated with lipid accumulation (1999, Wynn et al., *Microbiology* 145:1911-1917; 2002, Ratledge, *Biochem. Soc. Trans.* 30:1047-1050). Also, a mutant *Aspergillus nidulans* isolate lacking malic enzyme activity was shown to accumulate half as much lipid as produced by *A. nidulans* strains having malic enzyme (1997, Wynn et al., *Microbiology* 143:253-257).

However, studies in wild type *Y. lipolytica* suggest that malic enzyme may not play as large a role in lipid production. Beopoulos et al. (2011, *Appl. Microbiol. Biotechnol.* 90:1193-1206) briefly report that the overexpression of the mitochondrial form of malic enzyme did not affect lipid accumulation in *Y. lipolytica*.

Notwithstanding the foregoing disclosures, surprisingly, it has been found that the lipid content of a transgenic *Yarrowia* species, comprising an engineered polyunsaturated fatty acid biosynthetic pathway and having a lipid content of at least about 35% by weight of the dry cell weight of the *Yarrowia* species, can be increased by overexpressing cytosolic malic enzyme.

SUMMARY OF THE INVENTION

In one embodiment, the invention concerns a transgenic *Yarrowia* species that comprises (i) a polynucleotide encoding a cytosolic malic enzyme, (ii) a lipid content that is at least about 35% by weight of the dry cell weight of the *Yarrowia* species, and (iii) an engineered polyunsaturated fatty acid (PUFA) biosynthetic pathway, wherein overexpression of the cytosolic malic enzyme increases lipid content.

In a second embodiment, the cytosolic malic enzyme encoded by the polynucleotide comprises a dysfunctional mitochondrial targeting sequence. In a third embodiment, the cytosolic malic enzyme lacks a mitochondrial targeting sequence.

In a fourth embodiment, the cytosolic malic enzyme encoded by the polynucleotide comprises an amino acid sequence having at least about 90% sequence identity to SEQ ID NO:5 and has malic enzyme activity.

In a fifth embodiment, the transgenic *Yarrowia* species has a lipid content that is at least about 50% by weight of the dry cell weight of the *Yarrowia* species.

In a sixth embodiment, the engineered PUFA biosynthetic pathway comprised by the transgenic *Yarrowia* species produces at least one PUFA such as linoleic acid, alpha-linolenic acid, gamma-linolenic acid, stearidonic acid, eicosadienoic acid, dihomo-gamma-linolenic acid, arachidonic acid, eicosatrienoic acid, eicosatetraenoic acid, eicosapentaenoic acid, docosatetraenoic acid, omega-3 docosapentaenoic acid, omega-6 docosapentaenoic acid, or docosahexaenoic acid. Preferably, the engineered PUFA biosynthetic pathway produces eicosapentaenoic acid.

In a seventh embodiment, the transgenic *Yarrowia* species is *Yarrowia lipolytica*.

In an eighth embodiment, the invention concerns a method for increasing the lipid content of a transgenic *Yarrowia* species that comprises:

a) culturing the transgenic *Yarrowia* species of the invention, wherein a microbial oil comprising at least one PUFA is produced, and b) optionally, recovering the microbial oil of step (a).

With respect to the method, the cytosolic malic enzyme may comprise a dysfunctional mitochondrial targeting sequence or the cytosolic malic enzyme does not comprise a mitochondrial targeting sequence. Furthermore, the cytosolic malic enzyme may comprise an amino acid sequence having at least about 90% sequence identity to SEQ ID NO:5 and has malic enzyme activity.

In still another aspect of the method, the lipid content of the *Yarrowia* species is at least about 50% by weight of the dry cell weight of the *Yarrowia* species.

In yet another aspect of the method, the engineered PUFA biosynthetic pathway produces at least one PUFA selected from the group consisting of linoleic acid, alpha-linolenic acid, gamma-linolenic acid, stearidonic acid, eicosadienoic acid, dihomo-gamma-linolenic acid, arachidonic acid, eicosatrienoic acid, eicosatetraenoic acid, eicosapentaenoic acid, docosatetraenoic acid, omega-3 docosapentaenoic acid, omega-6 docosapentaenoic acid, and docosahexaenoic acid. Preferably, the at least one PUFA produced is eicosapentaenoic acid.

BRIEF DESCRIPTION OF THE DRAWINGS AND SEQUENCES

FIG. 1: An alignment of the amino acid sequences of MEs expressed by *Saccharomyces cerevisiae* (ScME), *Schizosaccharomyces pombe* (SpME) and *Yarrowia lipolytica* (YIME) is shown. The underlined amino acids in the depicted YIME sequence represent a predicted mitochondrial targeting sequence (MTS).

FIG. 2: Plasmids for ectopic expression of *Y. lipolytica* MEs are shown. Construct pME (A) contains a cassette (FBAIN::YIME::PEX20) for overexpression of full length (native) *Y. lipolytica* ME (YIME), whereas construct pMET2 (B) contains a cassette (FBAIN::YIME-T2::PEX20) for overexpression of truncated (cytosolic) *Y. lipolytica* ME (YIME-T2). Construct pBlue-YURA3 (C) was used for control purposes.

FIG. 3: An alignment of the amino acid sequences of YIME and YIME-T2 is shown. This version of YIME differs by one residue (second amino acid) compared to the ME natively expressed in *Y. lipolytica* that is shown in FIG. 1.

Figure 4:
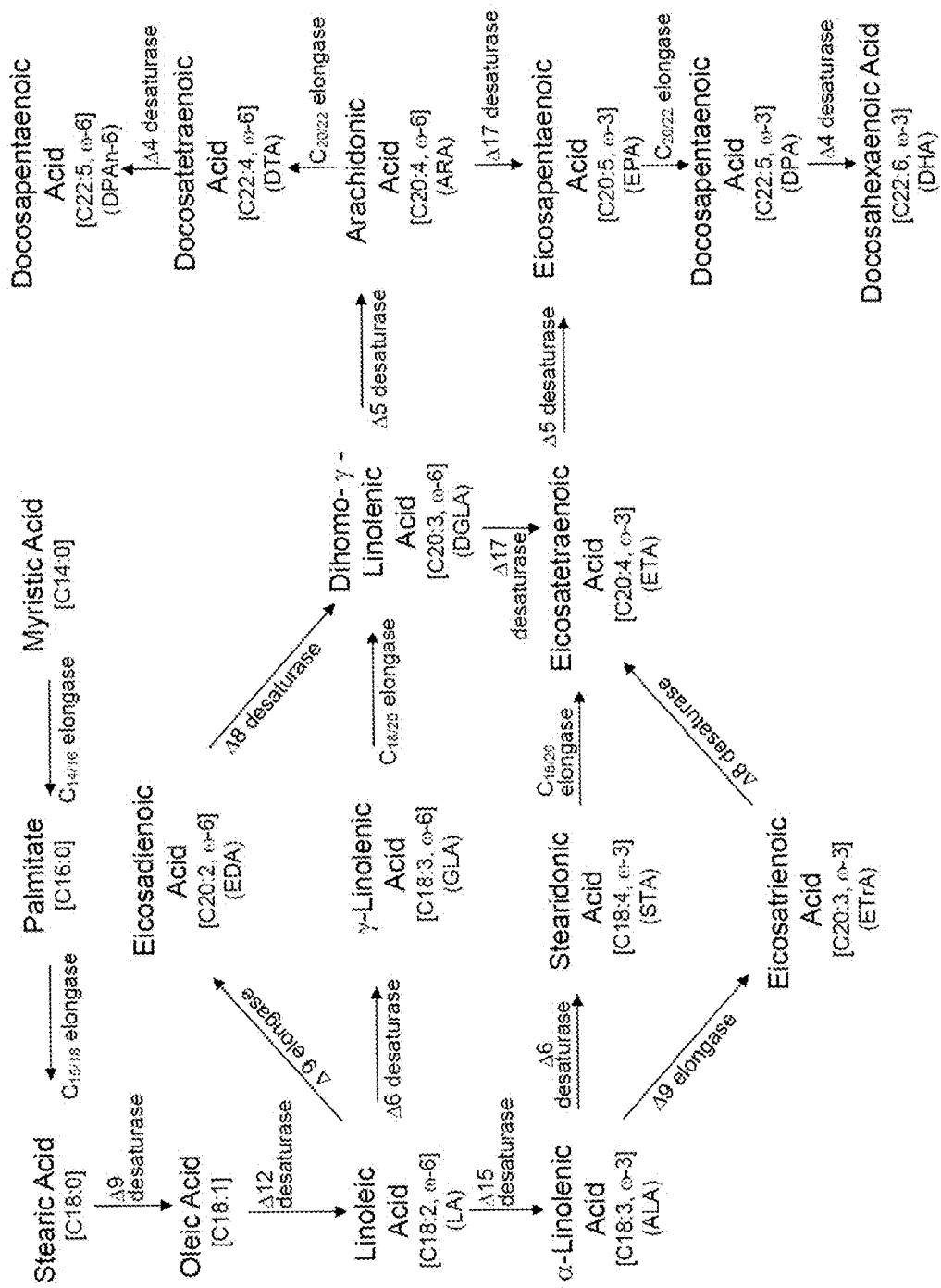

FIG. 4: Biosynthetic pathways for producing omega-3 and omega-6 fatty acids in *Yarrowia* are shown.

Figure 5:
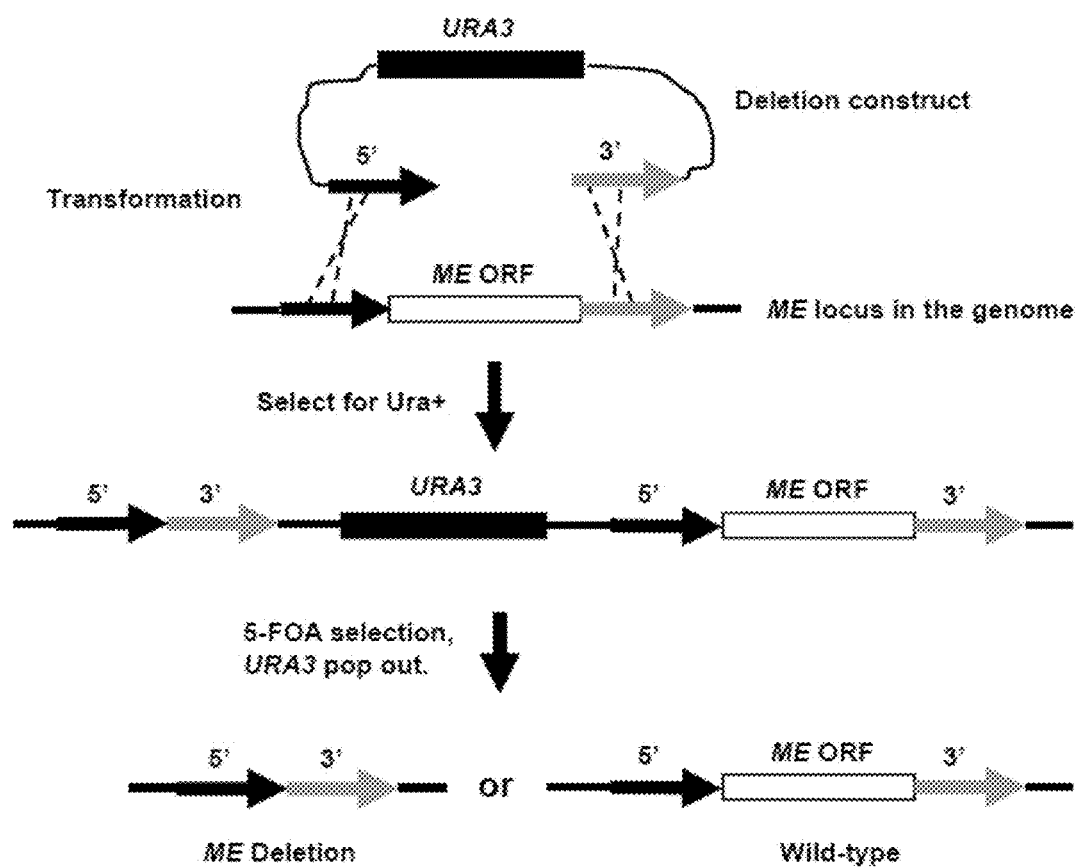

FIG. 5: The general scheme for disrupting the ME gene locus in a genome is shown. Briefly, transformants that have been targeted with the ME deletion construct are selected for a Ura+ phenotype, followed by selection with 5-fluoroorotic acid (5-FOA) for a Ura− phenotype. Screening is then performed for Ura− clones in which the ME gene has been recombined out of the genome along with the URA3 gene.

Figure 6:
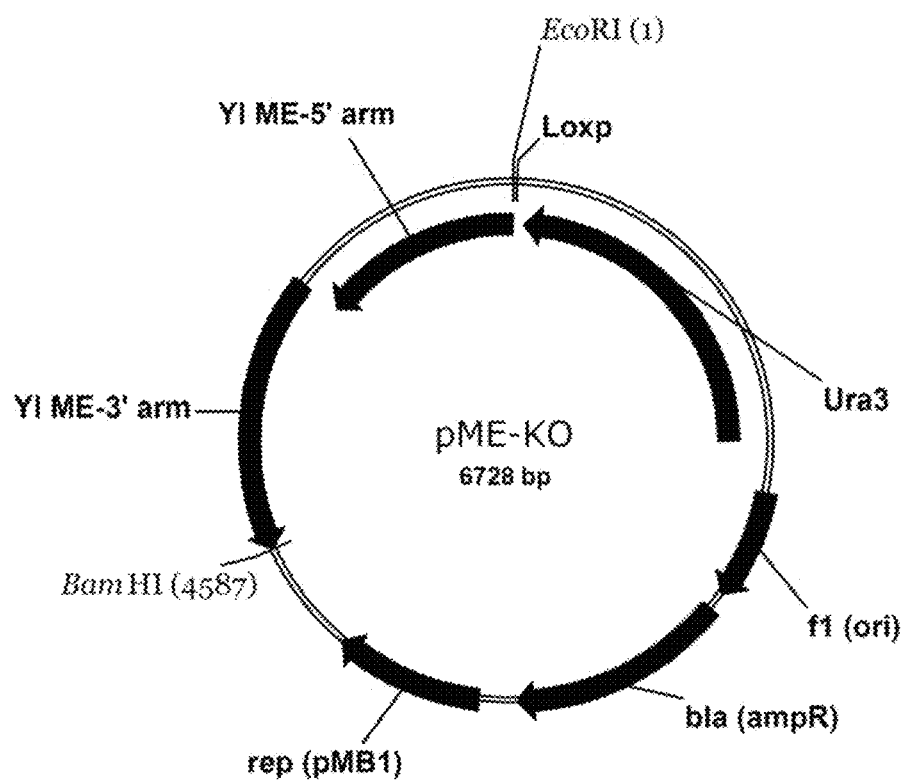

FIG. 6: Shown is plasmid pME-KO for knocking out the ME gene in *Y. lipolytica*.

TABLE 1

Summary of Gene and Protein SEQ ID Numbers

| Description | Nucleic acid SEQ ID NO. | Protein SEQ ID NO. |
|---|---|---|
| Malic enzyme, derived from *Yarrowia lipolytica* (YIME) | 1 | (629 a.a.) |
| Malic enzyme, derived from *Saccharomyces cerevisiae* (ScME) | 2 | (669 a.a.) |
| Malic enzyme, derived from *Schizosaccharomyces pombe* (SpME) | 3 | (565 a.a.) |
| Cytosolic *Yarrowia lipolytica* malic enzyme (YIME-T2), used in construct pMET2 | 4 | 5 (578 a.a.) |
| Malic enzyme, derived from *Yarrowia lipolytica* (YIME), used in construct pME (comprises L2V mutation) | 6 | 7 (629 a.a.) |
| Primer ME-TN2 | 8 | |
| Primer ME-T2 | 9 | |
| Plasmid construct pMET2 | 10 | |
| Primer ME-F | 11 | |
| Primer ME-R | 12 | |
| Plasmid construct pME | 13 | |
| Plasmid construct pBlue-YURA3 | 14 | |
| Plasmid construct pME-KO | 15 | |
| Primer YME-5-1 | 16 | |
| Primer YME-5-2 | 17 | |
| Primer YME-3-1 | 18 | |
| Primer YME-3-2 | 19 | |
| Primer YME-5-confirm-1 | 20 | |
| Primer YME-5-confirm-2 | 21 | |
| Primer YME-3-confirm-1 | 22 | |
| Primer YME-3-confirm-2 | 23 | |

TABLE 1-continued

Summary of Gene and Protein SEQ ID Numbers

| Description | Nucleic acid SEQ ID NO. | Protein SEQ ID NO. |
|---|---|---|
| *Yarrowia* malate dehydrogenase (MDH), mitochondrial | 24 | 25 (338 a.a.) |
| *Yarrowia* malate dehydrogenase (MDH), peroxisomal (carboxy terminus ends with . . . PPAN) | 26 | 27 (331 a.a.) |
| *Yarrowia* malate dehydrogenase (MDH), peroxisomal (carboxy terminus ends with . . . PPAKI) | 28 | 29 (332 a.a.) |
| *Yarrowia* malate dehydrogenase (MDH), mitochondrial (Phe2Val) | | 30 (338 a.a.) |
| Primer YMDH1-F | 31 | |
| Primer YMDH1-R | 32 | |

DETAILED DESCRIPTION OF THE INVENTION

All patents, patent applications, and publications cited are incorporated herein by reference in their entirety.

The following definitions are provided.

"Eicosapentaenoic acid" is abbreviated as "EPA".

"American Type Culture Collection" is abbreviated as "ATCC".

"Polyunsaturated fatty acid(s)" is abbreviated as "PUFA(s)".

"Triacylglycerols" are abbreviated as "TAGs".

"Total fatty acids" are abbreviated as "TFAs".

"Fatty acid methyl esters" are abbreviated as "FAMEs".

"Dry cell weight" is abbreviated as "DCW".

"Weight percent" is abbreviated as "wt %".

As used herein the term "invention" or "present invention" is intended to refer to all aspects and embodiments of the invention as described in the claims and specification herein and should not be read so as to be limited to any particular embodiment or aspect.

The term "malic enzyme" refers to an (S)-malate:NADP+ oxidoreductase (decarboxylating), pyruvic-malic carboxylase, NADP+-specific malic enzyme, or NADP+-malic enzyme. Malic enzyme carries out the irreversible decarboxylation of malate to pyruvate with the formation of NADPH from NADP+. Malic enzyme has the Enzyme Commission entries EC 1.1.1.39 and EC 1.1.1.40. The term "cytosolic malic enzyme" refers to a malic enzyme is targeted to the cytosol (cytoplasm) in the cell. Cytosolic targeting can occur if the malic enzyme lacks a mitochondrial targeting sequence or has a dysfunctional mitochondrial targeting sequence. The terms "malic enzyme" and "ME" are used interchangeably herein.

The term "mitochondrial targeting sequence" refers to an amino acid sequence that directs a protein to localize to the mitochondria. The terms "mitochondrial targeting sequence", "MTS", and "mitochondrial signal peptide" are used interchangeably herein. The MTS is generally located at the N-terminus of a protein and comprises one or more amphipathic helixes that have alternating hydrophobic amino acids and positively charged amino acids. The structure of the MTS permits a protein's interaction with mitochondrial surface receptors and subsequent translocation through the inner and outer mitochondrial membrane layers into the mitochondrial matrix, where the MTS is then cleaved. The MTS is generally twenty to eighty amino acids in length. Mitochondrial targeting sequence physiology has been described (e.g., *Molecular Biology of the Cell*, Alberts et al. 4th Edition, Garland Science: NY (2002).

The term "dysfunctional mitochondrial targeting sequence" refers to an MTS that does not have mitochondrial targeting function. An MTS may be dysfunctional by virtue of containing a deletion, insertion, and/or amino acid changes that alter the structural features of the MTS such that the MTS does not interact with mitochondrial surface receptors or allow mitochondrial membrane translocation. For example, a dysfunctional MTS may be rendered by removing or structurally impairing one or more amphipathic helixes of the MTS.

The term "lipids" refers to any fat-soluble (i.e., lipophilic), naturally-occurring molecule. A general overview of lipids is provided in U.S. Pat. Appl. Publ. No. 2009-0093543-A1 (see Table 2 therein).

The term "oil" refers to a lipid substance that is liquid at 25° C.; oil is hydrophobic and soluble in organic solvents. In oleaginous organisms, oil constitutes a major part of the total lipids "Oil" is composed primarily of triacylglycerols ["TAGs"], but may also contain other neutral lipids, phospholipids and free fatty acids. The fatty acid composition in the oil and the fatty acid composition of the total lipids are generally similar; thus, an increase or decrease in the concentration of fatty acids in the total lipids will correspond with an increase or decrease in the concentration of fatty acids in the oil, and vice versa.

The term "triacylglycerols" ["TAGs"] refers to neutral lipids composed of three fatty acyl residues esterified to a glycerol molecule. TAGs can contain long-chain PUFAs and saturated fatty acids, as well as shorter chain saturated and unsaturated fatty acids.

The term "total fatty acids" ["TFAs"] herein refers to the sum of all cellular fatty acids that can be derivatized to fatty acid methyl esters ["FAMEs"] by the base transesterification method (as known in the art) in a given sample, which may be the biomass or oil, for example. Thus, total fatty acids include fatty acids from neutral lipid fractions (including diacylglycerols, monoacylglycerols and TAGs) and from polar lipid fractions (including, e.g., the phosphatidylcholine and the phosphatidylethanolamine fractions), but not free fatty acids.

The term "total lipid content" of cells is a measure of TFAs as a percent of the dry cell weight ["DCW"], although total lipid content can be approximated as a measure of FAMEs as a percent of the DCW ["FAMEs % DCW"]. Thus, total lipid content ["TFAs % DCW"] is equivalent to, e.g., milligrams of total fatty acids per 100 milligrams of DCW.

The concentration of a fatty acid in the total lipids is expressed herein as a weight percent of TFAs ["% TFAs"], e.g., milligrams of a given fatty acid per 100 milligrams of TFAs. Unless otherwise specifically stated herein, reference to the percent of a given fatty acid with respect to total lipids or oil is equivalent to the concentration of the fatty acid as % TFAs (e.g., % EPA of total lipids or oil is equivalent to EPA % TFAs).

In some cases, it is useful to express the content of a given fatty acid(s) in a cell as its weight percent of the dry cell weight ["% DCW"]. Thus, for example, a measure of EPA productivity ["EPA % DCW"] would be determined according to the following formula: (EPA % TFAs)*(TFAs % DCW)]/100. The content of a fatty acid(s) such as EPA in a cell as its weight percent of the dry cell weight ["% DCW"] can be approximated, however, as: (EPA % TFAs)*(FAMEs % DCW)]/100.

The terms "lipid profile" and "lipid composition" are interchangeable and refer to the amount of individual fatty acids contained in a particular lipid fraction, such as in the total lipid or the oil, wherein the amount is expressed as a wt % of TFAs. The sum of each individual fatty acid present in the mixture should be 100.

The term "oleaginous" as used in certain embodiments describes those organisms that tend to store their energy source in the form of lipid (Weete, In: Fungal Lipid Biochemistry, 2nd Ed., Plenum, 1980). An oleaginous microorganism can comprise, or can accumulate or produce, about 25% or more of its dry cell weight as oil (i.e., ≥25 TFAs % DCW).

The term "oleaginous yeast" refers to those microorganisms classified as yeasts that make oil. Examples of oleaginous yeast include, for example, the genera *Yarrowia, Candida, Rhodotorula, Rhodosporidium, Cryptococcus, Trichosporon* and *Lipomyces*.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["ω-6" or "n-6"] versus "omega-3 fatty acids" ["ω-3" or "n-3"] are provided in U.S. Pat. No. 7,238,482, which is incorporated herein by reference.

Nomenclature used to describe PUFAs herein is given in Table 2. In the "Shorthand Notation" column, the omega-reference system is used to indicate the number of carbons, the number of double bonds and the position of the double bond closest to the omega carbon, counting from the omega carbon, which is numbered 1 for this purpose. The remainder of Table 2 summarizes the common names of omega-3 and omega-6 fatty acids and their precursors, the abbreviations that will be used throughout

TABLE 2

Nomenclature of Polyunsaturated Fatty Acids and Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 n-6 |
| gamma-Linolenic | GLA | cis-6,9,12-octadecatrienoic | 18:3 n-6 |
| Eicosadienoic | EDA | cis-11,14-eicosadienoic | 20:2 n-6 |
| Dihomo-gamma-Linolenic | DGLA | cis-8,11,14-eicosatrienoic | 20:3 n-6 |
| Arachidonic | ARA | cis-5,8,11,14-eicosatetraenoic | 20:4 n-6 |
| alpha-Linolenic | ALA | cis-9,12,15-octadecatrienoic | 18:3 n-3 |
| Stearidonic | STA | cis-6,9,12,15-octadecatetraenoic | 18:4 n-3 |
| Eicosatrienoic | EtrA | cis-11,14,17-eicosatrienoic | 20:3 n-3 |
| Eicosa-tetraenoic | ETA | cis-8,11,14,17-eicosatetraenoic | 20:4 n-3 |
| Eicosa-pentaenoic | EPA | cis-5,8,11,14,17-eicosapentaenoic | 20:5 n-3 |
| Docosa-tetraenoic | DTA | cis-7,10,13,16-docosatetraenoic | 22:4 n-6 |
| Docosa-pentaenoic | DPAn-6 | cis-4,7,10,13,16-docosapentaenoic | 22:5 n-6 |
| Docosa-pentaenoic | DPA | cis-7,10,13,16,19-docosapentaenoic | 22:5 n-3 |

TABLE 2-continued

Nomenclature of Polyunsaturated Fatty Acids and Precursors

| Common Name | Abbreviation | Chemical Name | Shorthand Notation |
|---|---|---|---|
| Docosa-hexaenoic | DHA | cis-4,7,10,13,16,19-docosahexaenoic | 22:6 n-3 |

The term "PUFA biosynthetic pathway" refers to a metabolic process that converts oleic acid to omega-6 fatty acids such as LA, EDA, GLA, DGLA, ARA, DTA and DPAn-6 and omega-3 fatty acids such as ALA, STA, ETrA, ETA, EPA, DPA and DHA. This process is described in the literature (e.g., U.S. Pat. No. 7,932,077; U.S. Pat. Appl. Publ. No. 2009-0093543-A1). Briefly, this process involves elongation of the carbon chain through the addition of carbon atoms and desaturation of the molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode these enzymes) associated with the biosynthesis of a PUFA, including: delta-4 desaturase, delta-5 desaturase, delta-6 desaturase, delta-12 desaturase, delta-15 desaturase, delta-17 desaturase, delta-9 desaturase, delta-8 desaturase, delta-9 elongase, $C_{14/16}$ elongase, $C_{16/18}$ elongase, $C_{18/20}$ elongase and/or $C_{20/22}$ elongase.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "substantial portion" of an amino acid or nucleotide sequence is that portion comprising enough of the amino acid sequence of a polypeptide or the nucleotide sequence of a gene to putatively identify that polypeptide or gene, as described in U.S. Pat. Appl. Pub. No. 2010-0317072-A1, either by manual evaluation or by computer-automated sequence comparison and identification using algorithms such as BLAST (Basic Local Alignment Search Tool; Altschul, S. F., et al., *J. Mol. Biol.*, 215:403-410 (1993)).

The term "complementary" is used to describe the relationship between nucleotide bases that are capable of hybridizing to one another. For example, with respect to DNA, adenosine is complementary to thymine and cytosine is complementary to guanine.

The term "isolated" as used in certain embodiments refers to a polynucleotide or polypeptide molecule that has been completely or partially purified from its native source. In some instances, the isolated polynucleotide or polypeptide molecule is part of a greater composition, buffer system or reagent mix. For example, the isolated polynucleotide or polypeptide molecule can be comprised within a cell or organism in a heterologous manner.

"Gene" refers to a nucleic acid fragment that expresses a specific protein, and which may refer to the coding region alone or may include regulatory sequences upstream and/or downstream to the coding region (e.g., 5' untranslated regions upstream of the transcription start site of the coding region, 3' non-coding regions). "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Regulatory sequences" refer to nucleotide sequences located upstream of the coding sequence's transcription start site, 5' untranslated regions and 3' non-coding regions, and which may influence the transcription, RNA processing or stability, or translation of the associated coding sequence. Regulatory sequences may include promoters, enhancers, silencers, 5' untranslated leader sequence, introns, polyadenylation recognition sequences, RNA processing sites, effector binding sites, stem-loop structures and other elements involved in regulation of gene expression.

"Promoter" refers to a DNA sequence capable of controlling the expression of a coding sequence or functional RNA. In general, a promoter sequence is 5' upstream of a coding sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of cell growth and/or development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The terms "3' non-coding sequence", "transcription terminator" and "terminator" refer to DNA sequences located 3' downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

The term "operably linked" in certain embodiments refers to the association of nucleic acid sequences on a single nucleic acid fragment so that the function of one is affected by the other. For example, a promoter is operably linked with a coding sequence when it is capable of affecting the expression of that coding sequence. That is, the coding sequence is under the transcriptional control of the promoter. Coding sequences can be operably linked to regulatory sequences in sense or antisense orientation.

The term "recombinant" refers to an artificial combination of two otherwise separated segments of sequence, e.g., by chemical synthesis or by the manipulation of isolated segments of nucleic acids by genetic engineering techniques. The terms "recombinant", "transgenic", "transformed", "engineered" or "modified for exogenous gene expression" are used interchangeably herein.

The term "expression", as used herein, refers to the transcription and stable accumulation of sense (mRNA) or antisense RNA. Expression also includes translation of mRNA into a polypeptide.

The term "increased" as used in certain embodiments means having a greater quantity, for example a quantity only slightly greater than the original quantity, or for example a quantity in large excess compared to the original quantity, and including all quantities in between. Alternatively, "increased" may refer to a quantity or activity that is at least 1%, 2%, 3%, 4%, 5%, 6%, 7%, 8%, 9%, 10%, 11%, 12%, 13%, 14%, 15%, 16%, 17%, 18%, 19% or 20% more than the quantity or activity for which the increased quantity or activity is being compared. The terms "increased", "greater than", and "improved" are used interchangeably herein. The term "increased" can be used to characterize the expression of a polynucleotide encoding a protein, for example, where "increased expression" can also mean "over-expression".

"Transformation" refers to the transfer of a nucleic acid molecule into a host organism. The nucleic acid molecule may be a plasmid that replicates autonomously, or it may integrate into the genome of the host organism. Host organisms containing the transformed nucleic acid fragments are referred to as "transgenic", "recombinant" or "transformed" organisms or as "transformants".

"Stable transformation" refers to the transfer of a nucleic acid fragment into the genome of a host organism, including both nuclear and organellar genomes, resulting in genetically stable inheritance (i.e., the nucleic acid fragment is "stably integrated"). In contrast, "transient transformation" refers to the transfer of a nucleic acid fragment into the nucleus, or DNA-containing organelle, of a host organism resulting in gene expression without integration or stable inheritance.

The terms "plasmid" and "vector" refer to an extra-chromosomal element often carrying genes that are not part of the central metabolism of the cell, and usually in the form of circular double-stranded DNA fragments. Such elements may have autonomously replicating sequences, genome integrating sequences, phage or nucleotide sequences, and may be linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA comprising the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter; 2) a coding sequence (i.e., ORF); and, 3) a terminator that usually contains a polyadenylation site in eukaryotes. The expression cassette(s) is usually included within a vector to facilitate cloning and transformation. Different expression cassettes can be transformed into different organisms including bacteria, yeast, plants and mammalian cells, as long as the correct regulatory sequences are used for each host.

The term "sequence analysis software" refers to any computer algorithm or software program that is useful for the analysis of nucleotide or amino acid sequences. Typical sequence analysis software includes, for example: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNASTAR (DNASTAR, Inc. Madison, Wis.); 4) SEQUENCHER (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.](1994), Meeting Date 1992, 111-120. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

"Sequence identity" or "identity" in the context of nucleic acid or polypeptide sequences in certain embodiments refers to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

Methods to determine "percent identity" and "percent similarity" are codified in publicly available computer programs. Percent identity and percent similarity can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humana: NJ (1994); 4) *Sequence Analysis in Molecular Bioloqy* (von Heinje, G., Ed.) Academic (1987); and, 5) *Sequence Analysis Primer* (Gribskov, M. and Devereux, J., Eds.) Stockton: NY (1991).

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Alternately, the "BLASTN method of alignment" is an algorithm provided by the National Center for Biotechnology Information (NCBI) to compare nucleotide sequences using default parameters, while the "BLASTP method of alignment" is an algorithm provided by the NCBI to compare protein sequences using default parameters.

Standard recombinant DNA and molecular cloning techniques used herein are well known in the art and are described by Sambrook, J., Fritsch, E. F. and Maniatis, T., Molecular Cloning: A Laboratory Manual, 2$^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience, Hoboken, N.J. (1987).

Various polypeptide amino acid sequences and polynucleotide sequences are disclosed herein as features of certain embodiments of the disclosed invention. Variants of these sequences that are at least about 70-85%, 85-90%, or 90%-95% identical to the sequences disclosed herein may be used in certain embodiments. Alternatively, a variant amino acid sequence or polynucleotide sequence in certain embodiments can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function of the disclosed sequence, or at least about 85%, 86%, 87%, 88%, 89%, 90%, 91%, 92%, 93%, 94%, 95%, 96%, 97%, 98%, or 99% of the function of the disclosed sequence.

As is shown in the Examples below, overexpression of malic enzyme, whether mitochondrial or cytosolic, had little or no impact on lipid production in wild type *Yarrowia lipolytica*.

Surprisingly and unexpectedly, it has been found that overexpression of cytosolic malic can increase lipid production in a transgenic *Yarrowia* species comprising:

(i) a polynucleotide encoding a cytosolic malic enzyme;

(ii) a lipid content that is at least about 35% of the dry cell weight of the *Yarrowia* species; and (iii) an engineered polyunsaturated fatty acid (PUFA) biosynthetic pathway.

Specifically, the transgenic *Yarrowia* species of the invention comprises, inter alia, a non-native cytosolic malic enzyme (ME)-encoding polynucleotide. In this sense, the polynucleotide encoding ME may be ectopic or heterologous to the *Yarrowia* species.

The polynucleotide encoding a cytosolic ME may be a polymer of DNA or RNA, and may be single- or double-stranded. The polynucleotide may contain nucleotides produced by the *Yarrowia* species containing the polynucleotide, or synthetic, non-natural or altered nucleotides (e.g., nucleotide base analogue). The polynucleotide may be in the form of a linear fragment or as a component of a larger nucleotide construct (e.g., plasmid, vector, linear or circular construct). The polynucleotide or a construct containing the polynucleotide may be chromosomal or episomal. The polynucleotide may alternatively be characterized as a gene, genetic sequence, nucleic acid sequence, DNA sequence, complementary DNA (cDNA) sequence, or RNA sequence.

The polynucleotide may contain an open reading frame (ORF) encoding a cytosolic ME (i.e., cytosolic ME coding sequence), as well as elements that regulate the expression of the cytosolic ME ORF. Alternatively, the polynucleotide may have an amino acid coding sequence having one or more introns that can be removed via gene splicing (e.g., a genomic copy of the cytosolic ME gene). Regulatory elements may include a promoter and/or a 3' transcriptional termination sequence (i.e., terminator sequence). Other elements may include translation leader sequences, introns, polyadenylation recognition sequences, RNA processing sites, effector binding sites, stem-loop structures and/or other elements involved in regulation of gene expression.

The above regulatory element(s) may be operably linked to the cytosolic ME coding region such that ME expression is functionally modulated by the element. In this sense, the element is active or operational in the *Yarrowia* species. Also, the polynucleotide may be considered to be expressible or capable of being expressed in the *Yarrowia* species. The activity of the promoter can be constitutive (for cytosolic ME overexpression) or have specific activity subject to a particular environmental stimulus (i.e., inducible). The regulatory elements may be native to, or heterologous to, the *Yarrowia* species containing the polynucleotide. A heterologous cytosolic ME gene cassette having one or more non malic enzyme gene regulatory elements and/or non-Yarrowia-derived regulatory elements may be characterized as chimeric. Examples of promoter and terminator sequences that may be used are provided in the below Examples section, and are also disclosed in U.S. Appl. Publ. Nos. 2006/0035351A1 and 2010/0068789A1, which are both incorporated herein by reference.

The expression of the amino acid coding sequence of the polynucleotide encoding the cytosolic ME in the *Yarrowia* species may be characterized as upregulated, enhanced, increased, elevated, or overexpressed in comparison to the level of expression that may have existed in the *Yarrowia* species before introducing the polynucleotide thereto (i.e., a control *Yarrowia*). Since *Yarrowia* species are believed to not have a native cytosolic ME gene, any level of exogenous expression of cytosolic ME from the polynucleotide can be characterized as upregulated or overexpressed, for example, as compared to the *Yarrowia* species before it was modified to contain the cytosolic ME-encoding polynucleotide (or as compared to some other suitable control such as a wild type *Yarrowia* or a transformed *Yarrowia* containing but not expressing a cytosolic ME-encoding polynucleotide, etc.). Nevertheless, the increased level of cytosolic ME expression in the *Yarrowia* species modified to contain the polynucleotide may be characterized to be at least about 5%, 10%, 20%, 30%, 40%, 50%, 60%, 75%, 80%, 90%, 100%, 150%, 200%, 500%, or 1000% above the expression of cytosolic ME in the *Yarrowia* species before it was modified to contain the cytosolic ME-encoding polynucleotide (or a corresponding *Yarrowia* control).

The terms "control cell" and "suitable control cell" are used interchangeably and may be referenced with respect to a cell in which a particular modification (e.g., over-expression of a polynucleotide, down-regulation of a polynucleotide) has been made (i.e., an "experimental cell"). A control cell may be any cell that does not have or does not express the particular modification of the experimental cell. Thus, a control cell may be an untransformed wild type cell or may be genetically transformed but does not express the genetic transformation. For example, a control cell may be a direct parent of the experimental cell, which direct parent cell does not have the particular modification that is in the experimental cell. Alternatively, a control cell may be a parent of the experimental cell that is removed by one or more generations. Alternatively still, a control cell may be a sibling of the experimental cell, which sibling does not comprise the particular modification that is present in the experimental cell. A sibling cell that could serve as a control cell could be a cell in which a plasmid for protein over-expression is inserted, but not expressed, in the sibling cell, whereas the plasmid is expressed in the experimental cell. It is well within the skill in the art to determine whether a cell can be a control cell.

The amino acid coding sequence of the polynucleotide encoding a cytosolic ME may be optimized for recognition by the protein translation machinery of the *Yarrowia* species into which the polynucleotide is placed. For example, the cytosolic ME ORF may be derived from a species other than *Yarrowia*, but codon-optimized for expression in *Yarrowia*. Codon optimization in this manner can be performed following the codon usage profile for *Yarrowia lipolytica* as provided in U.S. Pat. No. 7,125,672.

As an alternative to exogenous polynucleotide expression, the polynucleotide encoding a cytosolic ME may be expressed in *Yarrowia* from the native ME gene locus itself, but which has been appropriately modified. Since the native ME gene in *Yarrowia* encodes a mitochondrial ME, this gene would have to be modified using a genetic targeting technique (e.g., sequence knock-out) to remove all or part of the mitochondrial targeting sequence encoded at the 5'-end of the native *Yarrowia* ME ORF. Other modifications at the native *Yarrowia* ME gene locus could include the addition of a constitutive promoter, additional regulatory elements for overexpressing the modified gene, and/or modification of the translation start site so that the modified gene will produce ME localized in cytoplasm.

The cytosolic ME encoded by the polynucleotide may be characterized as a polypeptide that comprises the amino acid sequence of a cytosolic ME. The cytosolic ME can also be characterized as a cytosolic (S)-malate:NADP$^+$ oxidoreductase (decarboxylating), pyruvic-malic carboxylase, NADP$^+$-specific malic enzyme, or NADP$^+$-malic enzyme (Enzyme Commission entries EC 1.1.1.39 and EC 1.1.1.40).

Malic enzymes are responsible for various essential physiological functions in living organisms. The end products of the ME reaction (pyruvate, $CO_2$, NAD(P)H; see below) feed into numerous biological pathways such as the TCA cycle and reductive biosynthesis processes. Certain NADP-dependent isoforms of ME are found in bacteria, yeast, fungi, birds and mammals and primarily play a role in biosynthetic reactions such as lipid biosynthesis and desaturation through the provision of NADPH. Several isoforms of NADP-dependent ME exist in fungi through the action of post-translational modifications (either partial proteolytic cleavage, phosphorylation or dephosphorylation) (Saayman et al., 2006, S. *Afr. J. Enol. Vitic.* 27:113-122).

Malic enzyme activity catalyzes the following reaction:

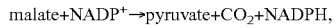

which can also be expressed as:

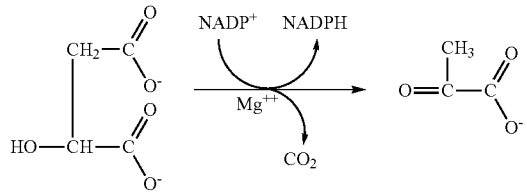

This reaction constitutes the oxidative decarboxylation of L-malate to pyruvate and $CO_2$. L-malate may also referred to as (S)-malate. Cytosolic ME activity may be NADP$^+$ (nicotinamide adenine dinucleotide phosphate)-dependent; in this sense, the cytosolic ME encoded by the polynucleotide may also be characterized, for example, as NADP$^+$-dependent ME, NADP$^+$-dependent cytosolic ME, or NADPH-producing ME. Methods for measuring cytosolic ME activity are well known in the art (e.g., Pongratz et al., 2009, *Methods. Enzymol.* 457:425-450; Geer et al., 1980, *Comp. Biochem. Physiol.* 65B:25-34; Fukuda et al., 2005, *Archaea.* 1:293-301).

Catalysis by ME generally proceeds in three steps: dehydrogenation of malate to produce oxaloacetate, decarboxylation of oxaloacetate to produce enolpyruvate, and tautomerisation of enolpyruvate to produce pyruvate. The active site residues of a ME can be roughly divided into four categories: (1) divalent cation-binding residues; (2) substrate-binding residues; (3) NAD(P)$^+$ cofactor binding residues; and (4) catalytic residues. A metal ion serves as a bridge to properly position malate at the active site (Saayman et al., 2006, S. *Afr. J. Enol. Vitic.* 27:113-122).

In one embodiment of the invention, the cytosolic malic enzyme encoded by the polynucleotide does not comprise a mitochondrial targeting sequence (MTS). The cytosolic ME may be derived from a mitochondrial ME from which the MTS has been removed. Since the cytosolic ME lacks an MTS—therefore it is not a mitochondrial ME—this ME does not locate to mitochondria, but rather locates within the cytosol of the cell. The cytosolic ME can also be characterized as a cytoplasmic ME or as an extramitochondrial ME. Alternatively, the cytosolic ME may be derived from or represent a malic enzyme that localizes to the cytosol in its native form (i.e., no genetic engineering or other modification is necessary to endow the property of cytosolic localization).

The MTS of a mitochondrial ME is located at the N-terminus of the protein. Therefore, removal of the MTS from a mitochondrial ME would involve deleting amino acid residues from or within the N-terminus. In this sense, a cytosolic ME obtained by removing the MTS from a mitochondrial ME can be characterized as amino-truncated or N-terminal-truncated with respect to the mitochondrial ME from which the cytosolic ME is derived.

An MTS can be identified as comprising an alternating pattern of hydrophobic amino acids and positively charged amino acids. Generally, an MTS has one or more helical sequences containing abundant positive charges on one face and hydrophobic residues on the other face (amphipathic helix). Depending on the nature and sequence of the MTS being manipulated, approximately the first 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, or 80 amino acids of the N-terminus of a mitochondrial ME can be removed to provide a cytosolic ME, or stretches of about 5, 10, 15, 20, 25, 30, 40, 45, 50, 55, 60, 65, 70, 75, or 80 contiguous amino acids within an MTS of a mitochondrial ME can be removed to provide a cytosolic ME. Alternatively, the amino acids of an MTS sub-structure (see Neupert, 1997, *Ann. Rev. Biochem.* 66:863-917, incorporated herein by reference) may be altered, deleted, or disrupted by insertion.

In another embodiment of the invention, the cytosolic malic enzyme encoded by the polynucleotide comprises a dysfunctional mitochondrial targeting sequence. For example, the cytosolic ME may lack a functional MTS by virtue of (i) lacking all or a portion of the MTS, (ii) containing one or more amino acid changes (e.g., resulting from genetic mutation or alteration) that inhibits MTS function, and/or (iii) providing to, or expressing in, a cell a factor that inhibits malic enzyme MTS function (e.g., small molecule, antibody, antigen-binding antibody fragment, aptamer etc.). An example of a cytosolic ME is a *Y. lipolytica* mitochondrial ME that lacks a functional MTS (e.g., a *Y. lipolytica* mitochondrial ME that lacks any or all of the amino acids of an MTS).

An MTS may be identified using an algorithm such as that described by Emanuelsson et al. (2000, *J. Mol. Biol.* 300: 1005-1016). Other algorithms for identifying an MTS in a protein include, for example, MitoProt (Claros et al., 1996, *Eur. J. Biochem.* 241:779-786), Predotar (Small et al., 2004, *Proteomics* 4:1581-1590), and pTARGET (Guda et al., 2005, *Bioinformatics* 21:3963-3969). Alternatively, an MTS may be identified by aligning a query sequence with one or more MTS amino acid sequences that have been characterized in other proteins.

In general, an MTS functions by first binding to a receptor on the outer mitochondrial membrane (transporter of outer membrane, or "Tom") via interactions through the hydrophobic surface(s) of the MTS (Roise et al., 1988, *J. Biol. Chem.* 263:4509-4511). Then the MTS, through its positively charged surface(s), transfers to another Tom receptor complex (Brix et al., 1997, *J. Biol. Chem.* 272:20730-20735) containing a channel. Following translocation through the Tom channel into the mitochondrial inter-membrane space, the basic residues of the MTS mediate interaction with a highly acidic complex (transporter of inner membrane, or "Tim"), which mediates importation of the MTS-containing protein into the mitochondrial matrix (Abe et al., 2000, *Cell* 100:551-560). Once transport is complete, the MTS is usually cleaved from the protein (Neupert, 1997, *Ann. Rev. Biochem.* 66:863-917).

The MTS of a malic enzyme may be identified and/or made dysfunctional with respect to any of these molecular interactions. For example, binding assays may be performed to determine if certain ME N-terminal amino acids of a putative MTS bind to the above-described receptor-channel complexes of the mitochondrial outer and inner membranes. Removing and/or altering one or more of those amino acids that mediate ME's binding to these factors may prevent the MTS from targeting ME to mitochondria.

The cytosolic ME encoding-polynucleotide may be derived from a polynucleotide encoding an ME from a *Yarrowia* species or from a different organism. Malic enzymes are widely distributed in nature and have been reported in the yeasts *S. pombe, Rhodotorula glutinis, Z. bailii, S. cerevisiae* and *C. utilis*. The *S. cerevisiae, C. utilis* and *S. pombe* MEs are bifunctional and can react with both malate and oxaloacetate. The *S. cerevisiae* ME can use both $NAD^+$ and $NADP^+$ as an electron acceptor, with $NAD^+$ being favoured. The *C. utilis* ME uses either $NAD^+$ or $NADP^+$ for the decarboxylation of oxaloacetate, but only $NADP^+$ for the decarboxylation of L-malate. Yeast MEs show variability with respect to their substrate affinities and metal requirements. The *S. pombe* ME has a very high substrate affinity ($K_m=3.2$ mM) as opposed to the ME of *S. cerevisiae* ($K_m=50$ mM). The *C. utilis* and *S. pombe* cytosolic MEs require the divalent cations $Mn^{2+}$ or $Mg^{2+}$ for activity, in contrast to the mitochondrial *S. cerevisiae* ME which prefers $Mn^{2+}$ (Saayman et al., 2006, *S. Afr. J. Enol. Vitic.* 27:113-122).

The cytosolic ME can be derived, for example, from any of the polypeptides provided in SEQ ID NO:1, SEQ ID NO:2, or SEQ ID NO:3 (FIG. 1), or GenBank Accession Nos. NP_012896, ABL67725, XP_504112, XP_001683592.1, AAF54860.1, AAF54859.1, NP_731739.1, NP_524880.2, EHQ58305.1, AEY64427.1, EHP69692.1, EHP69535.1, AEX51047.1, ZP_09413940.1 EHM12738.1, EHM10701.1, AEV69826.1, AEV24956.1, AEV24553.1, ZP_09201798.1, AEV29176.1, AEV33715.1, ACU98038.1, EAZ89719.1, AET68238.1, AET65914.1, EHI48436.1, YP_003543293.1, YP_003134865.1, ADE35429.1, ACL02315.1, ZP_08187924.1, ZP_08182502.1, ZP_08177630.1, EGD19865.1, EGD14411.1, ZP_01730858.1, AAB07709.1, AAA41563.1, XP_001913406.1, ADX74453.1, ACZ23235.1, ACU98385.1, YP_003316069.1, YP_003148857.1, YP_003154265.1, ZP_09629862.1, ACR47743.1, EHP37708.1, AEX51358.1, YP_004063227.1, ADR27874.1, ADN70279.1, ADN63267.1, NP_439983.1, YP_004076148.1, ZP_09517186.1, EHN27331.1, ZP_09329416.1, EHL58360.1, ADT98313.1, ZP_09289264.1, ZP_09285866.1, ZP_09267857.1, BAL27832.1, YP_001655800.1, EHK74844.1, YP_004510107.1, YP_003142912.1, EHJ97543.1, EBA14945.1, ZP_09091420.1, ZP_08429361.1, ABV78885.1, ZP_05120299.1, EGJ31523.1, ADJ15331.1, ADI89962.1, EGJ23089.1, ZP_08663698.1, ZP_05586166.1, ZP_04466958.1, ABM45933.1, ZP_06862982.1, ZP_03833419.1,ZP_03513851.1, ZP_02331708.1, ZP_07448622.1, ZP_02153123.1,ZP_02151206.1, ZP_01916022.1, ZP_01883625.1, ZP_01870789.1, AAC47396.1, BAE47514.1, EHQ60523.1, NP_838014.1, YP_001019404.1, YP_984283.1, AAF37577.1, CAA39690.1, CCC74376.1, BAB76295.1, YP_647281.1, NP_422343.1, NP_244034.1, YP_001239856.1, XP_002283814.1, AEW62565.1, YP_001232212.1, YP_001235403.1, YP_001002607.1, EEU87611.1, NP_002386.1, NP_001155058.1, EFG91746.1, AAF54860.1, NP_524880.2, AEC06242.1, NP_001105383.1, AAA41563.1, EAT42717.1, AAK97531.1, XP_002572611.1, NP_001138325.1, NP_001015690.1, NP_001128692.1, NP_001231187.1, NP_001082582.1, NP_001003627.2, XP_532217.3, XP_848770.1, XP_001499853.2, XP_001499424.2, XP_518610.3, ADK56109.1, EDN59877.1, ABL67725.1, GAA86393.1, XP_001267753.1, ABM30154.1, CAX41101.1, XP_001825515.1, EHA55338.1, XP_001395105.2, XP_001390670.2, XP_003236013.1, EEA25978.1, XP_002548578.1, EGU77660.1, or XP_448858.1. With any of these ME polypeptides, those that are mitochondrial may be appropriately modified (see above) to render cytosolic targeting or localization. A variant of any of these polypeptides may be used, but should have ME enzymatic activity (e.g., see above) and cytosolic localization. Such a variant may comprise an amino acid sequence that is at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of the reference ME. Preferably, a variant ME comprises an amino acid sequence that is at least about 90% identical to the reference ME. Where one of these reference MEs is mitochondrial, it should be understood that a variant thereof that localizes to the cytosol may contain mutations, deletions, and/or insertions in the MTS that interfere with MTS targeting activity (see above).

The cytosolic ME encoded by the polynucleotide may be prokaryotic or eukaryotic, and may be from bacteria, fungi, yeasts, plants, animals, protozoa, or algae. The *Yarrowia* species may contain 1, 2, 3, 4, 5, 6, 7, 8, or more polynucleotides encoding the same or a combination of different cytosolic ME polypeptides.

A cytosolic ME polypeptide encoded by the polynucleotide may comprise SEQ ID NO:5 (FIG. 3). SEQ ID NO:5 represents a *Yarrowia* mitochondrial ME from which the first 53 amino acids have been removed. Alternatively, a variant of this cytosolic ME may comprise an amino acid sequence that is at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:5. Such a variant should have ME enzymatic activity (e.g., see above) and cytosolic localization. In one embodiment of the invention, the cytosolic malic enzyme comprises an amino acid sequence having at least about 90% sequence identity to SEQ ID NO:5 and has malic enzyme activity.

A cytosolic ME polypeptide encoded by the polynucleotide may comprise of an amino acid sequence that is at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:7 (FIG. 3); such a variant should localize to the cytosol and have ME enzymatic activity (e.g., see above). Given that SEQ ID NO:7 represents a mitochondrial ME, it should be understood that a variant thereof that localizes to the cytosol has mutations, deletions, and/or insertions (see above) in the MTS that interfere with MTS targeting activity.

An example of a polynucleotide sequence encoding a cytosolic ME is one that comprises SEQ ID NO:4, which encodes SEQ ID NO:5. Alternatively, given the degeneracy of the genetic code, a polynucleotide may comprise a variant of SEQ ID NO:4 that encodes SEQ ID NO:5. For example, such a variant polynucleotide may be at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:4 and encode SEQ ID NO:5. Another polynucleotide may have a sequence encoding a variant Yarrowia ME polypeptide described above.

The Basic Local Alignment Search Tool (BLAST) algorithm, which is available online at the National Center for Biotechnology Information (NCBI) website, may be used to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4.

Within a cellular context, a cytosolic ME can alternatively be provided by altering (e.g., amino acid mutation, deletion, or insertion) a protein that interacts with the MTS of a mitochondrial ME to effect mitochondrial transport. Such an alteration may inhibit the MTS-interacting protein from binding the MTS domain, thereby preventing mitochondrial transport of the ME. Thus, the "mitochondrial ME" may become a cytosolic ME by virtue of not being targeted to the mitochondria. Examples of MTS-interacting proteins that play a role in ME mitochondrial targeting that can be altered for the above purpose are disclosed by Neupert (1997, *Ann. Rev. Biochem.* 66:863-917).

The cytosolic ME encoded by the polynucleotide, including any variant thereof (e.g., homolog, mutant, deletant, etc.), has malic enzyme activity (see above). Where a variant has lower activity compared to its reference ME (e.g., native ME, wild type ME, unaltered ME, endogenous ME, etc.), the activity of the variant ME should have at least about 20%, 30%, 40%, 50%, 60%, 70%, 80%, 85%, 90%, 91%, 92%, 93%, 94%, 95%, 96%, 97%, 98%, or 99% of the activity of the reference ME.

The amino acid sequence of the cytosolic ME encoded by the polynucleotide may comprise an added protein tag or epitope, such that the ME is expressed as a tagged protein (i.e., fusion protein) that can be more easily detected or isolated. The tag or epitope should not interfere with ME enzymatic activity (e.g., see above) and cytosolic targeting.

The preferred *Yarrowia* species used to practice the invention is *Yarrowia lipolytica*. Examples of *Y. lipolytica* strains that can be used to prepare the transgenic *Yarrowia* species provided herein are available from the American Type Culture Collection (ATCC, Manassas, Va.): strain designations ATCC #20362, #8862, #8661, #8662, #9773, #15586, #16617, #16618, #18942, #18943, #18944, #18945, #20114, #20177, #20182, #20225, #20226, #20228, #20327, #20255, #20287, #20297, #20315, #20320, #20324, #20336, #20341, #20346, #20348, #20363, #20364, #20372, #20373, #20383, #20390, #20400, #20460, #20461, #20462, #20496, #20510, #20628, #20688, #20774, #20775, #20776, #20777, #20778, #20779, #20780, #20781, #20794, #20795, #20875, #20241, #20422, #20423, #32338, #32339, #32340, #32341, #34342, #32343, #32935, #34017, #34018, #34088, #34922, #34922, #38295, #42281, #44601, #46025, #46026, #46027, #46028, #46067, #46068, #46069, #46070, #46330, #46482, #46483, #46484, #46436, #60594, #62385, #64042, #74234, #76598, #76861, #76862, #76982, #90716, #90811, #90812, #90813, #90814, #90903, #90904, #90905, #96028, #201241, #201242, #201243, #201244, #201245, #201246, #201247, #201249, or #201847.

In addition to the polynucleotide encoding a cytosolic malic enzyme, transgenic *Yarrowia* species of the invention also comprise an engineered PUFA biosynthetic pathway.

For example, the metabolic process wherein oleic acid is converted to EPA involves elongation of the carbon chain through the addition of carbon atoms and desaturation of the molecule through the addition of double bonds. This requires a series of special desaturation and elongation enzymes present in the endoplasmic reticulum membrane. However, as described below, multiple alternate pathways exist for EPA production.

Specifically, FIG. 4 depicts the pathways described below. All pathways require the initial conversion of oleic acid to linoleic acid ["LA"], the first of the omega-6 fatty acids, by a delta-12 desaturase. Then, using the "delta-9 elongase/delta-8 desaturase pathway" and LA as substrate, long-chain omega-6 fatty acids are formed as follows: 1) LA is converted to eicosadienoic acid ["EDA"] by a delta-9 elongase; 2) EDA is converted to dihomo-gamma-linolenic acid ["DGLA"] by a delta-8 desaturase; 3) DGLA is converted to arachidonic acid ["ARA"] by a delta-5 desaturase; 4) ARA is converted to docosatetraenoic acid ["DTA"] by a $C_{20/22}$ elongase; and, and 5) DTA is converted to docosapentaenoic acid ["DPAn-6"] by a delta-4 desaturase.

The delta-9 elongase/delta-8 desaturase pathway can also use alpha-linolenic acid ["ALA"] as substrate to produce long-chain omega-3 fatty acids as follows: 1) LA is converted to ALA, the first of the omega-3 fatty acids, by a delta-15 desaturase; 2) ALA is converted to eicosatrienoic acid ["ETrA"] by a delta-9 elongase; 3) ETrA is converted to eicosatetraenoic acid ["ETA"] by a delta-8 desaturase; 4) ETA is converted to eicosapentaenoic acid ["EPA"] by a delta-5 desaturase; 5) EPA is converted to docosapentaenoic acid ["DPA"] by a $C_{20/22}$ elongase; and 6) DPA is converted to docosahexaenoic acid ["DHA"] by a delta-4 desaturase. Optionally, omega-6 fatty acids may be converted to omega-3 fatty acids. For example, ETA and EPA are produced from DGLA and ARA, respectively, by delta-17 desaturase activity. Advantageously for the purposes herein, the delta-9 elongase/delta-8 desaturase pathway enables production of an EPA oil that lacks significant amounts of gamma-linolenic acid ["GLA"].

Alternate pathways for the biosynthesis of omega-3/omega-6 fatty acids utilize a delta-6 desaturase and $C_{18/20}$ elongase, that is, the "delta-6 desaturase/delta-6 elongase pathway". More specifically, LA and ALA may be converted to GLA and stearidonic acid ["STA"], respectively, by a delta-6 desaturase; then, a $C_{18/20}$ elongase converts GLA to DGLA and/or STA to ETA.

Economical commercial production of EPA in a recombinant Yarrowia sp. host cell requires consideration of a variety of variables, including the EPA concentration ["EPA % TFAs"] and total lipid content ["TFAs % DCW"]. Furthermore, it is desirable to reduce the production of intermediate fatty acids and by-product fatty acids in the final oil product in order to maximize production of the desired fatty acid, i.e., EPA.

neither EPA nor an intermediate fatty acid that can be further converted to EPA.

U.S. Pat. Appl. Publ. No. 2009-0093543-A1 describes optimized strains of recombinant Yarrowia lipolytica having the ability to produce microbial oils comprising at least about 43.3 EPA % TFAs, with less than about 23.6 LA % TFAs (an EPA:LA ratio of 1.83). The preferred strain was Y4305, whose maximum production was 55.6 EPA % TFAs, with an EPA:LA ratio of 3.03. Generally, the EPA strains of U.S. Pat. Appl. Publ. No. 2009-0093543-A1 comprised the following genes of the omega-3/omega-6 fatty acid biosynthetic pathway:

a) at least one gene encoding delta-9 elongase;

b) at least one gene encoding delta-8 desaturase;

c) at least one gene encoding delta-5 desaturase;

d) at least one gene encoding delta-17 desaturase;

e) at least one gene encoding delta-12 desaturase;

f) at least one gene encoding $C_{16/18}$ elongase; and g) optionally, at least one gene encoding diacylglycerol cholinephosphotransferase (CPT1).

Examples of preferred genes having the enzymatic functionalities described above are set forth in Table 3 (although these genes are not intended to be limiting).

TABLE 3

Preferred Desaturases and Elongases for EPA Biosynthesis in Yarrowia lipolytica

| ORF | Organism | Patent Reference | Wildtype Abbreviation | Codon-Optimized Abbreviation | Mutant Abbreviation |
|---|---|---|---|---|---|
| delta-9 elongase | Euglena gracillis | U.S. Pat. No. 7,645,604 | "EgD9e" | "EgD9eS" | — |
| | Eutreptiella sp. CCMP389 | U.S. Pat. No. 7,645,604 | "E389D9e" | "E389D9eS" | — |
| | Euglena anabaena UTEX 373 | U.S. Pat. Appl. Publ. No. 2008-0254522-A1; Intl. App. Publ. No. WO 2008/128241 | "EaD9e"* | "EaD9eS" | — |
| delta-8 desaturase | Euglena gracilis | U.S. Pat. No. 7,256,033; U.S. Pat. No. 7,709,239 | "EgD8"* | "EgD8S"* | "EgD8M"* |
| | Euglena anabaena UTEX 373 | U.S. Pat. Appl. Publ. No. 2008-0254521-A1; Intl. Appl. Publ. No. WO 2008/124194 | "EaD8"* | "EaD8S" | — |
| delta-5 desaturase | Euglena gracilis | U.S. Pat. No. 7,678,560; U.S. Pat. Appl. Publ. No. 2010-0075386-A1 | "EgD5" | "EgD5S" | "EgD5M"; "EgD5SM" |
| | Peridinium sp. CCMP626 | U.S. Pat. 7,695,950; U.S. Pat. Appl. Publ. No. 2010-0075386-A1 | "RD5" | "RD5S" | — |
| | Euglena anabaena UTEX 373 | U.S. Pat. Appl. Publ. No. 2008-0274521-A1; U.S. Pat. Appl. Publ. No. 2010-0075386-A1 | "EaD5"* | "EaD5S"* | "EaD5SM" |
| delta-17 desaturase | Phytophthora ramorum | U.S. Pat. No. 7,465,793 | "PrD17" | "PrD17S" | — |
| | Pythium aphanidematum | U.S. Pat. No. 7,556,949 | "PaD17" | "PaD17S" | — |
| delta-12 desaturase | Fusarium moniliforme | U.S. Pat. No. 7,504,259 | "FmD12"* | "FmD12S" | — |
| $C_{16/18}$ elongase | Mortierella alpina | U.S. Pat. No. 7,470,532 | "ELO3" | — | — |
| Diacylglycerol cholinephosphotransferase | Yarrowia lipolytica | Intl. Appl. Publ. No. WO 2006/052870 | "YlCPT" | — | — |

*Notes: EaD9e was identified as "EaD9Elo1" in U.S. Pat. Appl. Publ. No. 2008-0254522-A1; EgD8 was identified as "Eg5" in U.S. Pat. No. 7,256,033; EgD8S was identified as "D8SF" in U.S. Pat. No. 7,256,033; EgD8M was identified as "EgD8S-23" in U.S. Pat. No. 7,709,239; EaD8 was identified as "EaD8Des3" in U.S. Pat. Appl. Publ. No. 2008-0254521-A1; EaD5 was identified as "EaD5Des1" in U.S. Pat. Appl. Publ. No. 2008-0274521-A1; and FmD12 was identified as "Fm2" in U.S. Pat. No. 7,504,259.

Intermediate fatty acids are those fatty acids (e.g., oleic acid, LA, ALA, EDA, DGLA, ETA) that can be further converted to EPA by the action of other metabolic pathway enzymes. In contrast, by-product fatty acids (e.g., sciadonic acid, juniperonic acid) refer to any fatty acid produced that is As one skilled in the art will appreciate from the foregoing discussion, one or more of the above PUFA biosynthetic pathway enzymes may be derived from Yarrowia and/or from one or more oleaginous organisms. Such other oleaginous organisms may be characterized as an oleaginous microbe, yeast, mold, fungus, oomycete, bacteria, algae, stramenopile, or protist (e.g., euglenoid). Examples of oleaginous yeast, aside from *Yarrowia*, include species of the genera *Candida, Rhodotorula, Rhodosporidium, Cryptococcus, Trichosporon* and *Lipomyces*. Examples of oleaginous fungi include species of the genera *Fusarium* (e.g., *Fusarium lateritium*), *Mortierella* (e.g., *Mortierella alpina*) and *Mucor* (e.g., *Mucor rouxii* and *Mucor circinelloides*), which are all filamentous fungi. Examples of oleaginous algae include species of the genera *Entomophthora, Pythium* and *Porphyridium*.

In one embodiment of the invention, the engineered PUFA biosynthetic pathway produces at least one PUFA selected from the group consisting of linoleic acid, alpha-linolenic acid, gamma-linolenic acid, stearidonic acid, eicosadienoic acid, dihomo-gamma-linolenic acid, arachidonic acid, eicosatrienoic acid, eicosatetraenoic acid, eicosapentaenoic acid, docosatetraenoic acid, omega-3 docosapentaenoic acid, docosahexaenoic acid and omega-6 docosapentaenoic acid. Preferably, the PUFA produced is eicosapentaenoic acid.

In addition to (i) a polynucleotide encoding a cytosolic malic enzyme and (ii) an engineered polyunsaturated fatty acid (PUFA) biosynthetic pathway, the transgenic *Yarrowia* species of the invention also comprises a lipid content that is at least about 35% by weight of the dry cell weight of said *Yarrowia* species.

Examples of such high lipid-containing transgenic *Yarrowia* strains are Z1978, L250, L258, Z5565, Z5567, Z5575, Z5576, Z5620, Z5623, Z5625, Z5581, Z5582, Z5583, Z5584, Z5570, Z5571, Z5572, Z5574, Z5585 and Z5627, all of which are disclosed in U.S. Appl. Publ. No. 2012/0052537 A1, the disclosure of which is incorporated herein by reference. Other examples of high lipid-containing transgenic *Yarrowia* strains that can be used in practicing the invention are disclosed in U.S. Appl. Publ. No. 2010/0317072 A1 (e.g., strains Y8647, Y9028, Y9029, Y9031, Y9481, Y9502, Y9508 and Y9510), all of which are hereby incorporated by reference. All of these exemplary *Yarrowia* strains are capable of producing a lipid content greater than about 35% by weight of the dry cell weight of the respective strain.

The transgenic *Yarrowia* species may have a lipid content (i.e., total lipids or oil) that is by weight at least about 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65% of the DCW of the *Yarrowia* species. In a preferred embodiment of the invention, the lipid content is at least about 50% by weight of the dry cell weight of the *Yarrowia* species.

The level of total lipids or oil (TFAs % DCW) produced by the transgenic *Yarrowia* species may increase at least about 4%, 5%, 6%, 7%, 8%, 9%, 10%, 11%, 12%, 13%, 14%, or 15% relative to the total lipid/oil content that was in the *Yarrowia* species prior to insertion of a cytosolic ME-encoding polynucleotide (or relative to another suitable control such as a wild type *Yarrowia* or a transformed *Yarrowia* containing but not expressing a cytosolic ME-encoding polynucleotide, etc.).

Constructs or vectors comprising the gene(s) of interest may be introduced into a host cell by any standard technique. These techniques include transformation (e.g., lithium acetate transformation [*Methods in Enzymology*, 194:186-187 (1991)]), biolistic impact, electroporation, microinjection, or any other method that introduces the gene(s) of interest into the host cell. As an example, U.S. Pat. Nos. 4,880,741 and 5,071,764, and Chen et al. (*Appl. Microbiol. Biotechnol.*, 48(2):232-235 (1997)), describe integration techniques for *Yarrowia lipolytica*, based on linearized fragments of DNA.

For convenience, a *Yarrowia* cell that has been manipulated by any method to take up a DNA sequence (e.g., an expression cassette) is referred to herein as "transformed", "engineered", "transformant" or "recombinant". The transformed host will have at least one copy of the expression cassette and may have two or more, depending upon whether the expression cassette is integrated into the genome or is present on an extrachromosomal element having multiple copies. The transformed host cell can be identified by various selection techniques, as described for example in U.S. Pat. Nos. 7,238,482 and 7,259,255.

Preferred selection methods for use herein are resistance to kanamycin, hygromycin and the amino glycoside G418, as well as ability to grow on media lacking uracil, leucine, lysine, tryptophan or histidine. In alternate embodiments, 5-fluoroorotic acid (5-fluorouracil-6-carboxylic acid monohydrate; "5-FOA") is used for selection of yeast Ura⁻ mutants (U.S. Pat. Appl. Publ. No. 2009-0093543-A1), or a native acetohydroxyacid synthase (or acetolactate synthase; E.C. 4.1.3.18) that confers sulfonyl urea herbicide resistance (Intl. Appl. Publ. No. WO 2006/052870) is utilized for selection of transformants. A unique method of "recycling" a pair of preferred selection markers for their use in multiple sequential transformations, by use of site-specific recombinase systems, is also taught in U.S. Pat. Appl. Publ. No. 2009-0093543-A1.

It may be desirable to manipulate a number of different genetic elements that control aspects of transcription, RNA stability, translation, protein stability and protein location, oxygen limitation and secretion from the host cell. More specifically, gene expression in certain embodiments may be controlled by altering the following: the nature of the relevant promoter and terminator sequences; the number of copies of the cloned gene; whether the gene is plasmid-borne or integrated into the genome of the host cell; the final cellular location of the synthesized foreign protein; the efficiency of translation in the host organism; the intrinsic stability of the cloned gene protein within the host cell; and the codon usage within the cloned gene, such that its frequency approaches the frequency of preferred codon usage of the host cell. Several of these methods of overexpression will be discussed below and are useful during genetic manipulation of recombinant microbial host cells as a means to overexpress genes.

Promoters useful to drive expression of heterologous genes in microbial host cells are numerous and known to those skilled in the art. Expression can be accomplished in an induced or constitutive fashion. Induced expression can be accomplished by inducing the activity of a regulatable promoter operably linked to the gene of interest, while constitutive expression can be achieved by the use of a constitutive promoter operably linked to the gene of interest. Virtually any promoter (i.e., native, synthetic, or chimeric) capable of directing expression of a gene is suitable, although transcriptional and translational regions from the host species are particularly useful.

In general, the terminator can be derived from the 3' region of the gene from which the promoter was obtained or from a different gene. A large number of terminators are known and function satisfactorily in a variety of hosts, when utilized both in the same and different genera and species from which they were derived. The terminator usually is selected more as a matter of convenience rather than because of any particular property. Preferably, the terminator is derived from a yeast gene. The terminator can also be synthetic, as one of skill in the art can utilize available information to design and synthesize a terminator. A terminator may be unnecessary, but it is highly preferred.

Although not intended to be limiting, preferred promoters and terminators for use in a recombinant microbial host cell of the genus *Yarrowia* are those taught in U.S. Pat. Appl. Publ. No. 2009-0093543-A1, U.S. Pat. Appl. Publ. No. 2010-0068789-A1, U.S. Pat. Pub. No. 2011-0059496-A1, U.S. Provisional Pat. Appl. No. 61/469,933, U.S. Provisional Pat. Appl. No. 61/470,539, U.S. Provisional Pat. Appl. No. 61/471,736, and U.S. Provisional Pat. Appl. No. 61/472,742, the disclosure of each which is hereby incorporated by reference.

Additional copies (i.e., more than one copy) of the PUFA biosynthetic pathway desaturases, elongases, etc. genes may be introduced into the recombinant microbial host cell to thereby increase EPA production and accumulation. Specifically, additional copies of genes may be cloned within a single expression construct; and/or additional copies of the cloned gene(s) may be introduced into the host cell by increasing the plasmid copy number or by multiple integration of the cloned gene into the genome.

It is noted that when preparing an optimized recombinant microbial host cell according to the methodology herein, copies of various desaturases, elongases, DGLA synthases, etc. are often referred to. If, for example, 2 copies of a delta-9 elongase are required, this can refer to: 1) two copies of an identical coding sequence for a particular delta-9 elongase isolated from a single species; or 2) one coding sequence for a delta-9 elongase isolated from a species "A" and one coding sequence for a delta-9 elongase isolated from a species "B", thus collectively resulting in two delta-9 elongases.

In general, once a DNA cassette (e.g., comprising a chimeric gene comprising a promoter, ORF and terminator) suitable for expression in a recombinant microbial host cell has been obtained, it is either placed in a plasmid vector capable of autonomous replication in the host cell or directly integrated into the genome of the host cell. Integration of expression cassettes can occur randomly within the host genome or can be targeted through the use of constructs containing regions of homology with the host genome sufficient to target recombination with the host locus. Although not relied on herein, all or some of the transcriptional and translational regulatory regions can be provided by the endogenous locus where constructs are targeted to an endogenous locus.

The transgenic *Yarrowia* species in certain embodiments may further comprise a heterologous polynucleotide encoding a malate dehydrogenase (MDH) enzyme. In other words, cytosolic ME can be co-expressed with an MDH. The MDH in certain embodiments is MDH (EC 1.1.1.37), which is an enzyme that reversibly catalyzes the oxidation of malate to oxaloacetate using the reduction of NAD$^+$ to NADH. Since MDH (EC 1.1.1.37) also catalyzes the reverse of this reaction (i.e., oxaloacetate to malate), the expression of MDH can increase the amount of malate substrate available to cytosolic ME. This in turn can help sustain cytosolic ME production of NADPH when converting malate to pyruvate. This intersection of the MDH and cytosolic ME reactions can be illustrated as follows (where MAE is malic enzyme and PYC is pyruvate carboxylase):

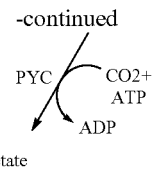

Alternatively, the MDH in certain embodiments is a "malate dehydrogenase (NADP+)", which can also be referred to as "(S)-malate:NADP$^+$ oxidoreductase". Malate dehydrogenase (NADP+) (EC 1.1.1.82) is an enzyme that catalyzes the chemical reaction: (S)-malate+NADP$^+$→oxaloacetate+NADPH+H$^+$. Malate dehydrogenase (NADP+) belongs to the oxidoreductase family of enzymes, specifically those acting on the CH—OH group of donor with NAD$^+$ or NADP$^+$ as acceptor. The NADPH produced from this reaction represents source of NADPH for fatty acid synthesis.

The MDH (EC 1.1.1.37 or EC 1.1.1.82) in certain embodiments can be prokaryotic or eukaryotic, and may be from bacteria, fungi, yeasts, plants, animals, protozoa, algae, or stramenopiles. The *Yarrowia* species may contain 1, 2, 3, 4, 5, 6, 7, 8, or more heterologous polynucleotides encoding the same or a combination of different MDH enzymes. The MDH can be a mitochondrial MDH, cytosolic MDH, or peroxisomal MDH, for example. Several MDH enzymes, both EC 1.1.1.37 and EC 1.1.1.82, are known in the art.

In certain embodiments of the invention, the MDH co-expressed with cytosolic ME in the *Yarrowia* species may be a *Yarrowia* MDH. Such an MDH can be over-expressed using a heterologous polynucleotide in the *Yarrowia* species, taking into account native gene expression of the MDH. The *Yarrowia* MDH can comprise SEQ ID NO:25, for example. SEQ ID NO:25 is a mitochondrial MDH. Alternatively, the *Yarrowia* MDH can comprise an amino acid sequence that is at least about 90%, 91%, 92%, 93%, 94%, 95%, 96%, 97%, 98%, or 99% identical to SEQ ID NO:25, and have MDH activity (e.g., oxaloacetate conversion to malate). A polynucleotide encoding any of these MDH amino acid sequences can be used, such as SEQ ID NO:24, for example. In certain embodiments, the MDH comprises SEQ ID NO:30, which differs from SEQ ID NO:25 by one amino acid residue (contains a valine residue instead of a phenylalanine residue at position 2).

The *Yarrowia* MDH can comprise SEQ ID NO:27 or SEQ ID NO:29 in certain embodiments of the invention. SEQ ID NO:27 and SEQ ID NO:29 are peroxisomal MDH enzymes. Alternatively, the *Yarrowia* MDH can comprise an amino acid sequence that is at least about 90%, 91%, 92%, 93%, 94%, 95%, 96%, 97%, 98%, or 99% identical to SEQ ID NO:27 or SEQ ID NO:29, and have MDH activity (e.g., oxaloacetate conversion to malate). A polynucleotide encoding any of these MDH amino acid sequences can be used, such as SEQ ID NO:26 or SEQ ID NO:28, for example.

With respect to engineered recombinant *Y. lipolytica* host cells, the preferred method of expressing genes in this microbial host is by integration of a linear DNA fragment into the genome of the host. Integration into multiple locations within the genome can be particularly useful when high level expression of genes is desired. Preferred loci include those taught in U.S. Pat. Appl. Publ. No. 2009-0093543-A1.

Furthermore, Juretzek et al. (Yeast, 18:97-113 (2001)) note that the stability of an integrated DNA fragment in *Y. lipolytica* is dependent on the individual transformants, the recipient strain and the targeting platform used. Thus, a skilled artisan will recognize that multiple transformants of a particular recombinant microbial host must be screened in order to obtain a strain displaying the desired expression level and pattern. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618 (1-2):133-145 (1993)), Western analysis of protein expression, phenotypic analysis or GC analysis of the PUFA products.

The present invention also concerns a method for increasing the lipid content of a transgenic *Yarrowia* species that comprises:

a) culturing the transgenic *Yarrowia* species of the invention wherein a microbial oil comprising at least one PUFA is produced, and b) optionally, recovering the microbial oil of step (a).

Oil may be recovered or obtained from the transgenic *Yarrowia* species after about 12, 24, 36, 48, 60, 72, 84, 96, 100, 105, 110, 115, 120, 125, 130, 135, 140, 145, 150, 160, 170, 180, or 200 hours of culturing the *Yarrowia* species to produce a microbial oil comprising at least one PUFA.

The transgenic *Yarrowia* species of the present disclosure can be grown under conditions that optimize expression of chimeric genes (e.g., encoding desaturases, elongases, etc.) and produce the greatest and the most economical yield of one or more PUFAs. In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. For example, *Yarrowia lipolytica* is generally grown in a complex media such as yeast extract-peptone-dextrose broth ["YPD"] or a defined minimal media that lacks a component necessary for growth and thereby forces selection of the desired expression cassettes (e.g., Yeast Nitrogen Base (DIFCO Laboratories, Detroit, Mich.)).

Fermentation media for the methods and host cells described herein must contain a suitable carbon source, such as are described in U.S. Pat. No. 7,238,482 and U.S. Pat. Appl. Publ. No. 2011-0059204-A1. Although it is contemplated that the source of carbon utilized in the present invention may encompass a wide variety of carbon-containing sources, preferred carbon sources are sugars (e.g., glucose, invert sucrose, fructose and combinations of thereof), glycerols and/or fatty acids (e.g., those containing between 10-22 carbons).

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the recombinant microbial host cell and the promotion of the enzymatic pathways for EPA production. Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara et al., *Ind. Appl. Single Cell Oils*, D. J. Kyle and R. Colin, eds. pp 61-97 (1992)).

Preferred growth media for the methods and host cells described herein are common commercially prepared media, such as Yeast Nitrogen Base or corn steep liquors. Other defined or synthetic growth media may also be used. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of EPA in *Yarrowia lipolytica*. This approach is described in U.S. Pat. No. 7,238,482, as are various suitable fermentation process designs (i.e., batch, fed-batch and continuous) and considerations during growth.

Example 10 of U.S. Pat. Appl. Publ. No. 2009-0093543-A1 also provides a detailed description of parameters required for a 2-L fermentation of the recombinant *Yarrowia lipolytica* strain Y4305 (whose maximum production was 12.1 EPA % DCW [55.6 EPA % TFAs, with a ratio of EPA % TFAs to LA % TFAs of 3.03] over a period of 162 hours). This disclosure includes a description of means to prepare inocula from frozen cultures to generate a seed culture, initially culture the yeast under conditions that promoted rapid growth to a high cell density, and then culture the yeast to promote lipid and PUFA accumulation (via starving for nitrogen and continuously feeding glucose). Process variables including temperature (controlled between 30-32° C.), pH (controlled between 5-7), dissolved oxygen concentration and glucose concentration were monitored and controlled per standard operating conditions to ensure consistent process performance and final PUFA oil quality.

In some aspects of the invention, the primary product is the recombinant microbial biomass. As such, isolation and purification of the PUFA-containing oils from the microbial biomass may not be necessary (i.e., wherein the whole cell biomass is the product). However, certain end uses and/or product forms may require partial and/or complete isolation/purification of the EPA-containing oil from the microbial biomass, to result in partially purified microbial biomass, purified oil, and/or purified EPA. See U.S. Pat. Appl. Publ. No. 2010-0317072-A1 for further details regarding these aspects.

EXAMPLES

Except as specifically delineated herein, the following procedures were used in the Examples. The procedures for culturing *Y. lipolytica* strains, and for measuring the dry cell weight, lipid content and fatty acid profile thereof, were generally performed as described in U.S. Pat. Appl. Publ. Nos. 2008/0254191 and 2009/0093543, which are incorporated herein by reference. The procedures for transforming *Y. lipolytica* strains with plasmid expression vectors were generally performed as described in U.S. Pat. Appl. Publ. No. 2009/0093543, which is incorporated herein by reference. Recombinant DNA cloning and manipulation were performed using standard molecular biology procedures.

Example 1

Vector Construction for Native or Truncated (Cytosolic) *Y. lipolytica* Malic Enzyme Overexpression The amino acid sequence of *Yarrowia lipolytica* malic enzyme (ME) was analyzed to determine whether a mitochondrial targeting sequence (MTS) is contained therein. After identifying a putative MTS, vectors for full length (mitochondrial) ME and truncated (cytosolic) ME expression were constructed.

Malic Enzyme MTS Identification

*Y. lipolytica* ME sequence (YIME, SEQ ID NO:1, GenBank Acc. No. XP_504112) was analyzed using the TargetP 1.1 Server sequence analysis prediction program (Center for Biological Sequence Analysis, Technical University of Denmark, Lyngby, Denmark) as described by Emanuelsson et al. (2000, *J. Mol. Biol.* 300:10051016) to determine whether this protein may contain any particular subcellular localization sequences such as an MTS. This analysis suggested that *Yarrowia* ME contains a putative MTS of 26 amino acid residues in length (FIG. 1, underlined in YIME sequence).

It was reported that *Saccharomyces cerevisiae* malic enzyme (ScME, SEQ ID NO:2, GenBank Acc. No. EDN59877) is mitochondrial, whereas malic enzyme in *Schizosaccharomyces pombe* (SpME, SEQ ID NO:3, GenBank Acc. No. NP_587760) is cytosolic (Saayman et al., 2006, *S. Afr. J. Enol. Vitic.* 27(2):113-122). Comparing the sequences of malic enzymes from *S. cerevisiae*, *S. pombe* and *Y. lipolytica* showed that the first 55 and 85 amino acids of YIME and ScME, respectively, have no apparent counterpart in SpME (FIG. 1). This suggested that the MTS may be as long as, or contained within, the first 55 amino acid residues of YIME.

Construction of Vectors for Malic Enzyme Overexpression

A full length *Yarrowia* ME (YIME) ORF was obtained by polymerase chain reaction (PCR) amplification using 5'-end primer ME-F (SEQ ID NO:11, contains added NcoI site) and 3'-end primer ME-R (SEQ ID NO:12, contains added NotI site). These primers amplified the coding region from the ATG start codon to the stop codon, except that the second codon was changed from TTA (leu) to GTA (val) in order to engineer the added NcoI site. The PCR reaction mixture contained 1 µL of *Y. lipolytica* genomic DNA, 1 µL each of primers ME-F and ME-R (from 20 µM stocks), 22 µL water, and 25 µL Ex Taq™ premix 2×Taq PCR solution (TaKaRa Bio Inc., Siga, Japan). Amplification was carried out as follows: initial denaturation at 94° C. for 2 min, followed by 30 cycles of denaturation at 94° C. for 30 sec, primer annealing at 55° C. for 30 sec, and elongation at 72° C. for 90 sec. A final elongation period at 72° C. for 7 min was carried out, followed by reaction termination at 4° C. The DNA fragment amplified by the reaction was purified using the MinElute® Gel Extraction kit (QIAGEN, Valencia, Calif.) according to the manufacturer's protocol. The purified DNA was digested with NcoI and NotI, and cloned into an NcoI/NotI-cut plasmid having a pZP2-based vector backbone (see U.S. Pat. Appl. Publ. No. 2010/0159558 to yield the pME (SEQ ID NO:13) expression vector (FIG. 2A).

To construct a cytosolic version of *Yarrowia* ME, a DNA fragment encoding an N-terminally truncated version of YIME was created by PCR. This truncation removed the first 53 amino acids of YIME; the predicted MTS in this region was consequently removed with this sequence deletion. The YIME ORF lacking N-terminal amino acids 1-53 ("YIME-T2") was prepared as follows. Using the above PCR conditions, 5'-end primer ME-TN2 (SEQ ID NO:8, contains added NcoI site) and 3'-end primer ME-T2 (SEQ ID NO:9, contains added NotI site) were used to amplify the YIME-T2 ORF plus 203 base pairs of the 3'-untranslated region of the ME gene from *Y. lipolytica* genomic DNA. The amplified fragment was purified as above, digested with NcoI and NotI, and cloned into NcoI/NotI-cut pME vector to yield pMET2 (FIG. 2B, SEQ ID NO:10).

In both pME and pMET2, the cloned coding sequences (full length or truncated YIME, respectively) were under the transcriptional control of the FBAIN promoter of *Y. lipolytica* fructose-bisphosphate aldolase gene ("FBAIN", refer to U.S. Pat. No. 7,202,356). This promoter allows for overexpression of downstream gene sequences in *Yarrowia* species, for example. Also, both coding sequences are flanked at their 3'-ends by a terminator sequence from the *Y. lipolytica* PEX20 gene (GenBank Acc. No. AF054613). pMET2 had 203 bp of the 3' untranslated sequence of the YIME gene between the ME-T2 coding region and the PEX20 terminator. Correctly ligated constructs were confirmed by plasmid minipreparation and digestion analyses accordingly.

The constructed chimeric gene expression cassettes can be characterized in shorthand as FBAIN::YIME::PEX20 and FBAIN::YIME-T2::PEX20. An alignment of the translated YIME and YIME-T2 polypeptides is shown in FIG. 3. The sequences as amplified above can also be considered to represent cDNA sequences given that the coding region of the *Y. lipolytica* ME gene does not contain introns. The sequences of the YIME and YIME-T2 ORFs are set forth as SEQ ID NOs:6 and 4, respectively.

Example 2

ME Overexpression and its Effect on Lipid Production in *Y. lipolytica*

The effect of overexpressing wild type (full length) or cytosolic ME on the lipid content of different *Y. lipolytica* strains was determined using the constructs described in Example 1.

In the following gene overexpression studies, *Y. lipolytica* strains were transformed with either the FBAIN::YIME::PEX20 or FBAIN::YIME-T2::PEX20 chimeric gene expression cassette using plasmid pME or pMET2, respectively, that was digested with BssHII and SphI. For transformation control purposes, the strains used in each experiment were transformed with plasmid pBlue-YURA3 (FIG. 2C, SEQ ID NO:14) that was digested with KpnI and SaiI. Plasmid pBlue-YURA3 was derived from the cloning vector pBluescript®-SK(−) (Stratagene, La Jolla, Calif.) that was modified to contain the *Yarrowia* URA3 gene (GenBank Acc. No. AJ306421) in the pBluescript®-SK(−) multiple cloning site. Transformants were selected on plates lacking uracil, as the experimental and control vectors bestow a Ura$^+$ phenotype to the otherwise Ura$^−$ cells. *Y. lipolytica* strain Y2224 was used in these analyses; Y2224 is a Ura$^−$ strain of wild type strain ATCC #20362, and has a lipid content representative of wild type *Yarrowia*. The isolation of strain Y2224 is described in U.S. Pat. Appl. Publ. No. 2008/0254191, which is incorporated herein by reference.

Transformants were grown for 2 days in fermentation medium (FM, per liter: 6.70 g Yeast nitrogen base, 6.00 g KH$_2$PO$_4$, 2.00 g K$_2$HPO$_4$, 1.50 g MgSO$_4$*7H$_2$O, 20 g glucose, 5.00 g Yeast extract [BBL]), followed by 5 days of growth in high glucose medium (HGM, per liter: 80 g glucose, 2.58 g KH$_2$PO$_4$, 5.36 g K$_2$HPO$_4$, pH 7.5 [do not need to adjust]). After this incubation period, the lipid content (TFAs % DCW) and fatty acid profile of transformants were measured by gas chromatography as described in U.S. Pat. Appl. Publ. No. 2008/0254191.

Lipid Production in Strain Y2224 The lipid and fatty acid profiles of *Yarrowia* strain Y2224 transformed with pBlue-YURA3 (control), YIME, or YIME-T2 sequences are listed in Table 4. Four different (1-4) control transformants and eight (1-8) different transformants for YIME or YIME-T2 overexpression were analyzed. The detected fatty acids included 16:0 (palmitic acid), 16:1 (palmitoleic acid), 18:0 (stearic acid), 18:1 (oleic acid) and 18:2 (linoleic acid); the concentration of each fatty acid is presented as a weight percent of TFAs (i.e., "% TFAs") in Table 4.

TABLE 4

Lipid content in *Y. lipolytica* strain Y2224 overexpressing full length or cytosolic ME.

| Y2224 Transformant | TFAs % DCW | % TFAs | | | | |
|---|---|---|---|---|---|---|
| | | 16:0 | 16:1 | 18:0 | 18:1 | 18:2 |
| pBlue-YURA3-1 | 15.6 | 14.8 | 14.0 | 5.7 | 47.6 | 15.6 |
| pBlue-YURA3-2 | 14.7 | 14.9 | 14.0 | 5.8 | 47.4 | 15.6 |
| pBlue-YURA3-3 | 14.4 | 12.8 | 14.0 | 5.5 | 50.6 | 14.7 |
| pBlue-YURA3-4 | 14.2 | 13.4 | 12.3 | 5.9 | 50.4 | 15.6 |
| Average | 14.7 | 13.98 | 13.6 | 5.7 | 49 | 15.4 |
| pME-1 | 15.4 | 14.6 | 14.5 | 5.6 | 48.1 | 15.2 |
| pME-2 | 16.3 | 14.3 | 14.2 | 5.8 | 49.2 | 14.3 |
| pME-3 | 16.9 | 15.2 | 13.1 | 6.0 | 46.6 | 16.9 |
| pME-4 | 15.4 | 14.9 | 14.4 | 5.5 | 47.4 | 15.5 |
| pME-5 | 14.7 | 13.2 | 14.0 | 5.4 | 50.4 | 14.4 |
| pME-6 | 14.7 | 11.4 | 13.9 | 5.0 | 53.2 | 14.1 |
| pME-7 | 15.7 | 14.3 | 14.8 | 5.3 | 48.6 | 14.7 |
| pME-8 | 13.8 | 14.3 | 14.8 | 5.4 | 48.5 | 14.6 |
| Average | 15.4 | 14.0 | 14.2 | 5.5 | 49 | 14.96 |
| pMET2-1 | 15.1 | 14.2 | 14.7 | 5.2 | 48.1 | 14.2 |
| pMET2-2 | 13.0 | 11.9 | 12.3 | 5.4 | 49.7 | 17.6 |
| pMET2-3 | 17.6 | 14.0 | 14.1 | 5.4 | 49.0 | 14.0 |
| pMET2-4 | 14.5 | 12.5 | 14.3 | 5.1 | 51.5 | 13.7 |
| pMET2-5 | 15.5 | 13.6 | 14.2 | 5.3 | 49.4 | 13.9 |
| pMET2-6 | 15.1 | 14.0 | 14.9 | 5.0 | 49.0 | 14.1 |
| pMET2-7 | 15.0 | 14.2 | 14.9 | 5.0 | 48.4 | 14.4 |
| pMET2-8 | 13.8 | 15.1 | 12.1 | 5.5 | 48.4 | 15.9 |
| Average | 14.95 | 13.7 | 13.9 | 5.2 | 49.2 | 14.7 |

As shown in Table 4, most transformants for YIME and YIME-T2 overexpression produced a similar amount of total lipids as the ones carrying control plasmid pBlue-YURA3.

These results altogether indicate that neither the overexpression of full length ME or cytosolic ME substantially alters lipid production in a *Yarrowia* strain having wild type lipid production capacity. Specifically, neither full length or cytosolic ME overexpression significantly elevated lipid production from the wild type baseline level of about 15 TFAs % DCW under the described analytical conditions.

Lipid Production in Strain Z1978U

The pME and pME-T2 overexpression vectors were also used to transform an engineered strain of *Y. lipolytica*, Z1978U, which is a Ura⁻ strain of Z1978. The Z1978 strain can produce a lipid content greater than about 35 TFAs % DCW, with about 52 EPA % TFAs. Details regarding the development of strains Z1978 and Z1978U are provided in U.S. Appl. Publ. No. 2012/0052537 A1, which is incorporated herein by reference. The lipid and fatty acid profiles of the Z1978U transformants are listed in Table 5. Four different (1-4) control transformants and eight (1-8) different transformants for YIME or YIME-T2 overexpression were analyzed. The fatty acids detected in the total fatty acids included 18:0, 18:1, 18:2, dihomo-gamma-linolenic acid (DGLA) and eicosapentaenoic acid (EPA).

TABLE 5

Lipid content in *Y. lipolytica* strain Z1978U overexpressing full length or cytosolic ME

| Z1978U Transformant | TFAs % DCW | % TFAs | | | | | EPA % DCW |
|---|---|---|---|---|---|---|---|
| | | 18:0 | 18:1 | 18:2 | DGLA | EPA | |
| pBlue-YURA3-1 | 34.1 | 3.4 | 6.9 | 13.5 | 2.6 | 51.5 | 17.6 |
| pBlue-YURA3-2 | 33.8 | 3.4 | 6.9 | 13.4 | 2.6 | 52.2 | 17.6 |

TABLE 5-continued

Lipid content in *Y. lipolytica* strain Z1978U overexpressing full length or cytosolic ME

| Z1978U Transformant | TFAs % DCW | % TFAs | | | | | EPA % DCW |
|---|---|---|---|---|---|---|---|
| | | 18:0 | 18:1 | 18:2 | DGLA | EPA | |
| pBlue-YURA3-3 | 33.9 | 3.3 | 7.0 | 13.5 | 2.6 | 51.5 | 17.5 |
| pBlue-YURA3-4 | 33.9 | 3.4 | 7.0 | 13.6 | 2.6 | 51.4 | 17.4 |
| Average | 33.9 | 3.4 | 7.0 | 13.5 | 2.6 | 51.7 | 17.5 |
| pME-1 | 35.2 | 3.3 | 6.9 | 14.5 | 2.6 | 51.7 | 18.2 |
| pME-2 | 38.9 | 3.3 | 6.9 | 16.5 | 2.6 | 51.8 | 20.1 |
| pME-3 | 35.9 | 3.3 | 6.9 | 17.0 | 2.6 | 52.2 | 18.7 |
| pME-4 | 35.4 | 3.3 | 6.9 | 17.1 | 2.6 | 51.6 | 18.3 |
| pME-5 | 35.2 | 3.3 | 6.9 | 17.0 | 2.6 | 51.8 | 18.2 |
| pME-6 | 35.7 | 3.3 | 6.9 | 15.4 | 2.6 | 51.7 | 18.4 |
| pME-7 | 36.0 | 3.3 | 7.0 | 15.5 | 2.6 | 51.6 | 18.6 |
| pME-8 | 35.7 | 3.2 | 6.9 | 16.5 | 2.6 | 51.8 | 18.5 |
| Average | 36.0 | 3.3 | 6.9 | 16.2 | 2.6 | 51.8 | 18.6 |
| pMET2-1 | 37.8 | 2.2 | 5.7 | 16.8 | 3.4 | 54.4 | 20.5 |
| pMET2-2 | 37.9 | 3.3 | 7.0 | 17.2 | 2.6 | 51.8 | 19.6 |
| pMET2-3 | 39.6 | 3.3 | 6.9 | 17.2 | 2.6 | 51.7 | 20.5 |
| pMET2-4 | 37.4 | 3.3 | 7.0 | 16.8 | 2.6 | 51.5 | 19.2 |
| pMET2-5 | 35.7 | 3.4 | 7.1 | 16.8 | 2.6 | 51.4 | 18.3 |
| pMET2-6 | 37.7 | 3.1 | 7.1 | 16.6 | 2.7 | 51.7 | 19.5 |
| pMET2-7 | 34.2 | 3.3 | 6.9 | 16.5 | 2.6 | 51.9 | 17.8 |
| pMET2-8 | 38.4 | 3.3 | 7.0 | 16.6 | 2.6 | 51.7 | 19.9 |
| Average | 37.3 | 3.1 | 6.8 | 16.9 | 2.7 | 52.0 | 19.4 |

As shown in Table 5, most of the pME transformants showed a modest increase in lipid content (~5%) compared to the control transformants. However, most of the pME-T2 transformants produced a significantly higher lipid content (>10%) compared to the control transformants; particular examples are listed in bold in the table. The EPA content (EPA % DCW) in the pME-T2 transformants generally increased with the rise in total lipid content. Expression of cytosolic ME thus allowed increased production of lipids in strain Z1978U. This result is in contrast to the observations made above with strain Y2224 (has lipid levels representative of wild type *Yarrowia*), which on average did not exhibit a significant enhancement of lipid production with cytosolic ME overexpression.

These results altogether indicate that overexpression of cytosolic ME can significantly increase lipid production in a transgenic *Yarrowia* strain having a lipid production capacity over about 35 TFAs % DCW. Specifically, cytosolic ME overexpression in this strain increased lipid production by over 10% with respect to the control.

Lipid Production in Strain Z5567U

The above plasmids were similarly used to transform another engineered strain of *Yarrowia lipolytica*, Z5567U, which is a Ura⁻ strain of Z5567. The Z5567 strain can produce a lipid content greater than about 55.0 TFAs % DCW, with about 27.0 EPA % DCW. Details regarding the development of strains Z5567 and Z5567U are provided in U.S. Appl. Publ. No. 2012/0052537 A1, which is incorporated herein by reference. As shown in Table 6, four different (1-4) control transformants (pBlue-YURA3) and ten (1-10) different transformants for YIME or YIME-T2 overexpression in Z5567U were analyzed for lipid production. The fatty acids detected in the total fatty acids included 18:0, 18:1, 18:2, DGLA and EPA. The control and pME (full length *Yarrowia* ME) Z5567U transformants produced similar levels of total lipid. However, pMET2 (cytosolic *Yarrowia* ME) transformants produced significantly more total lipid compared to the control and pME transformants. Particular examples of total lipid levels that were elevated in pMET2 transformants are listed in Table 6 in bold.

TABLE 6

Lipid content in *Y. lipolytica* strain Z5567U overexpressing full length or cytosolic ME.

| Z5567U Transformant | TFAs % DCW | % TFAs | | | | | EPA % DCW |
|---|---|---|---|---|---|---|---|
| | | 18:0 | 18:1 | 18:2 | DGLA | EPA | |
| pBlue-YURA3-1 | 55.5 | 2.7 | 6.2 | 16.9 | 5.3 | 49.1 | 27.2 |
| pBlue-YURA3-2 | 54.1 | 2.6 | 6.2 | 16.8 | 5.3 | 49.0 | 26.5 |
| pBlue-YURA3-3 | 54.9 | 2.7 | 6.2 | 16.6 | 5.3 | 48.9 | 26.9 |
| pBlue-YURA3-4 | 54.7 | 2.6 | 6.1 | 16.5 | 5.3 | 49.2 | 26.9 |
| Average | 54.8 | 2.65 | 6.2 | 16.7 | 5.3 | 49.05 | 26.9 |
| pME-1 | 52.5 | 1.7 | 6.0 | 14.5 | 5.9 | 50.8 | 26.7 |
| pME-2 | 54.9 | 2.6 | 6.0 | 16.5 | 5.4 | 49.8 | 27.3 |
| pME-3 | 55.7 | 2.7 | 6.3 | 17.0 | 5.3 | 48.8 | 27.2 |
| pME-4 | 52.8 | 2.6 | 6.6 | 17.1 | 5.0 | 48.2 | 25.4 |
| pME-5 | 54.6 | 2.5 | 6.8 | 17.0 | 5.0 | 47.7 | 26.1 |
| pME-6 | 50.6 | 2.3 | 5.8 | 15.4 | 5.3 | 51.2 | 25.9 |
| pME-7 | 51.8 | 2.1 | 6.0 | 15.5 | 5.5 | 50.4 | 26.1 |
| pME-8 | 54.6 | 2.6 | 6.0 | 16.5 | 5.4 | 49.2 | 26.9 |
| pME-9 | 52.1 | 2.2 | 6.6 | 16.1 | 5.3 | 48.7 | 25.4 |
| pME-10 | 52.8 | 2.4 | 6.4 | 16.5 | 5.0 | 48.0 | 25.3 |
| Average | 53.2 | 2.4 | 6.25 | 16.2 | 5.3 | 49.3 | 26.2 |
| pMET2-1 | 54.9 | 2.7 | 6.2 | 16.8 | 5.3 | 49.3 | 27.0 |
| pMET2-2 | 56.0 | 2.8 | 6.5 | 17.2 | 5.2 | 47.9 | 26.8 |
| pMET2-3 | 59.4 | 2.7 | 6.5 | 17.2 | 5.2 | 48.3 | 28.7 |
| pMET2-4 | 55.8 | 2.7 | 6.3 | 16.8 | 5.2 | 48.6 | 27.1 |
| pMET2-5 | 55.8 | 2.7 | 6.3 | 16.8 | 5.3 | 49.4 | 27.6 |
| pMET2-6 | 57.2 | 2.7 | 6.2 | 16.6 | 5.3 | 48.7 | 27.9 |
| pMET2-7 | 56.9 | 2.8 | 6.2 | 16.5 | 5.4 | 49.0 | 27.9 |
| pMET2-8 | 55.5 | 2.2 | 5.9 | 16.6 | 5.2 | 50.6 | 28.1 |
| pMET2-9 | 58.8 | 2.7 | 6.3 | 16.6 | 5.4 | 59.1 | 28.8 |
| pMET2-10 | 54.3 | 2.6 | 7.1 | 17.5 | 4.9 | 47.3 | 25.7 |
| Average | 56.5 | 2.7 | 6.35 | 16.9 | 5.2 | 49.8 | 27.6 |

Expression of cytosolic ME also allowed increased production of lipids in strain Z5567U. Therefore, these results further indicate that overexpression of cytosolic ME can significantly increase lipid production in a transgenic *Yarrowia* strain having a lipid production capacity over about 35 TFAs % DCW. In this particular case, cytosolic ME overexpression increased lipid production in a strain having a lipid production capacity of over 50 TFAs % DCW under the described analytical conditions.

The results obtained using the engineered high lipid strains are in contrast to the observations made above with strain Y2224 (has lipid levels representative of wild type *Yarrowia*), which on average did not exhibit a significant enhancement of lipid production with cytosolic ME overexpression. Another difference was the effect on lipid content induced by full length ME versus cytosolic ME in Y2224 and Z5567U. In Y2224, the respective effects of overexpressing full length ME and cytosolic ME on lipid content compared to control were relatively similar. However, full length ME overexpression in strain Z5567U generally reduced lipid content compared to control, whereas cytosolic ME induced elevated lipid levels. Yet, in strain Z1978, the full length ME modestly increased lipid content, while cytosolic ME had a significantly more pronounced effect on increasing lipid levels. These data altogether indicate that cytosolic ME enhances the lipid production capacity of high lipid-producing strains of *Yarrowia*.

Based on these data, the NADPH reducing equivalents produced by cytosolic ME are likely a factor in lipid biosynthesis in *Yarrowia* strains that can produce approximately over 35 TFAs % DCW. NADPH produced by cytosolic ME in lower lipid producing *Yarrowia* strains does not appear to play as significant a role in lipid production. These observations could indicate that NADPH produced by cytosolic ME becomes more necessary for lipid biosynthesis as lipid production capacity increases in a strain (i.e., more lipid synthesis may require more reductive capacity). Interestingly, however, even though Z5567U produces more lipid than Z1978U, the effect of cytosolic ME overexpression on lipid production was more pronounced in Z1978U compared to Z5567U. For example, while cytosolic ME overexpression increased lipid production by over 10% in Z1978U (discussed above), lipid production in Z5567U was increased by over about 3% compared to the control.

In summary, the above results indicate that overexpression of cytosolic ME can significantly increase lipid production in transgenic *Yarrowia* strains having a lipid production capacity over about 35 TFAs % DCW.

Example 3

Deletion of the Gene Encoding ME and its Impact on Lipid Production in *Y. lipolytica*

Lipid production in *Yarrowia* lacking a native ME gene and in elevated lipid-producing transformants thereof was measured. Elevated lipid production was induced by diacylglycerol acyltransferase-2 (DGAT2) overexpression.

Malic Enzyme Gene Deletion

Plasmid pME-KO (FIG. 6, SEQ ID NO:15) was constructed to delete the ME gene in wild type *Yarrowia* through homologous recombination. FIG. 5 shows the general scheme of the disruption strategy. The 5'- and 3'-flanking regions of the ME gene were amplified by PCR using the following primer pairs: YME-5-1 (SEQ ID NO:16)/YME-5-2 (SEQ ID NO:17) for the 5'-flanking region, and YME-3-1 (SEQ ID NO:18)/YME-3-2 (SEQ ID NO:19) for the 3'-flanking region.

The PCR amplification was performed using *Yarrowia* genomic DNA as template. The reaction mixture contained 1 µL of the genomic DNA, 1 µL each primer (from 20 µM stocks), 22 µL water, and 25 µL Ex Taq™ premix 2×Taq PCR solution. Amplification was carried out as follows: initial denaturation at 94° C. for 2 min, followed by 30 cycles of denaturation at 94° C. for 30 sec, annealing at 55° C. for 30 sec, and elongation at 72° C. for 90 sec. A final elongation cycle at 72° C. for 7 min was carried out, followed by reaction termination at 4° C.

The two PCR products were cloned between the BamHI and EcoRI sites of pBlue-YURA3 in a three piece ligation reaction. The PCR product of the 5'-flanking region was digested with EcoRI and XhoI, and the PCR product of the 3'-flanking region was digested with XhoI and BamHI. Plasmid pBlue-YURA3 was digested with BamHI and EcoRI. The three DNA fragments were ligated together such that the two PCR products are joined together at an XhoI site, and the linked PCR products reside in between the BamHI and EcoRI sites of the vector. The resulting plasmid, pME-KO (SEQ ID NO:15) is shown in FIG. 6.

*Y. lipolytica* strain Y2224 (Ura⁻ representative of wild type *Yarrowia*, see above) was transformed with pME-KO digested with SphI. Transformants were plated on Ura-minus plates to select for integration of the constructs. Ura⁺ transformants were screened by colony PCR, using primers YME-5-confirm-1 (SEQ ID NO:20) and YME-5-confirm-2 (SEQ ID NO:21).

The reaction mixture contained 0.5 µL of each primer (20 µM stock), 14 µL water and 15 µL Ex Taq™ premix 2×Taq PCR solution. A small amount of cells was picked from the plate and added to the reaction mixture. PCR conditions were: initial denaturation at 95° C. for 5 min, followed by 35 cycles of denaturation at 94° C. for 20 sec, annealing at 55° C. for 20 sec, and elongation at 72° C. for 60 sec. A final elongation cycle at 72° C. for 7 min was carried out, followed by reaction termination at 4° C.

If the digested plasmid integrated into the *Yarrowia* genome at the ME locus, a ~1-kb fragment would have been generated by PCR. Three out of 36 transformants produced the expected PCR product. These three transformants were patched onto minimal media plates containing 350 µg/mL 5-fluoroorotic acid (5-FOA) (U.S. Pat. Appl. Publ. No. 2009-0093543) to select for cells that would undergo the second round of recombination to become Ura⁻. Cells that underwent the second round of recombination could either have (i) lost the wild type ME gene along with the deletion construct, or (ii) lost the deletion construct only, in which case the ME gene is left intact (refer to FIG. 5).

Sixteen colonies from the 5-FOA plates were selected and tested by colony PCR using primers YME-3-confirm-1 (SEQ ID NO:22) and YME-3-confirm-2 (SEQ ID NO:23). A ~1.3-kb fragment was expected if the ME gene was deleted from the strain. PCR conditions were the same as above with the confirmation PCR for the first round of recombination. Two of the Ura⁻ strains produced a PCR product having the correct size (~1.3 kb), indicating that these transformants contained the deletion. Both transformants were further confirmed for ME gene deletion by PCR using primers YME-5-confirm-2 and YME-3-confirm-1. This primer pair would amplify a 250-bp product if the ME gene was knocked out, or a ~1.7-kb product if the ME locus is wild type. Both Ura⁻ strains produced the 250-bp PCR fragment, thereby confirming that they were ME-deleted derivatives of strain Y2224.

Lipid Production in ME-deleted *Yarrowia*

Lipid measurements were made in ME-deleted strains to determine the role of ME in *Yarrowia* lipid production. As described below, ME-deleted Y2224 cells transformed with pBlue-YURA3, pME, or pME-T2 allowed this assessment with respect to native fatty acid synthesis.

A Ura⁻, ME⁻ strain of Y2224 was transformed with (i) pBlue-YURA3 digested with EcoRI and SaiI, (ii) pME digested with BssHII and SphI, or (iii) pME-T2 digested with BssHII and SphI. Transformants (selected on Ura-minus plates) were grown for 2 days in FM, followed by 5 days in HGM. The lipid content and fatty acid profiles of two transformants selected from each of the pBlue-YURA3, pME and pME-T2 transformations are shown below in Table 7; measurements were also made on two separate cultures of wild type *Yarrowia* strain ATCC #20362. The fatty acids detected in the total fatty acids included 16:0, 16:1, 18:0, 18:1 and 18:2.

TABLE 7

Lipid content in Y2224-ME⁻ strains transformed with pBlue-YURA3, pME, or pME-T2

| | TFAs | % TFAs | | | | |
|---|---|---|---|---|---|---|
| | % DCW | 16:0 | 16:1 | 18:0 | 18:1 | 18:2 |
| ATCC #20362 | 17.3 | 15.1 | 13.9 | 5.4 | 46.6 | 15.7 |
| ATCC #20362 | 17.1 | 15.0 | 13.7 | 5.6 | 46.8 | 15.6 |
| Y2224-ME⁻ + pBlue-YURA3-1 | 17.2 | 15.2 | 13.7 | 5.5 | 46.3 | 16.0 |
| Y2224-ME⁻ + pBlue-YURA3-1 | 16.8 | 15.1 | 13.9 | 5.5 | 46.8 | 15.6 |
| Y2224-ME⁻ + pME-1 | 15.1 | 14.5 | 12.9 | 5.9 | 47.9 | 15.4 |
| Y2224-ME⁻ + pME-2 | 16.9 | 17.1 | 13.0 | 6.0 | 42.2 | 18.1 |
| Y2224-ME⁻ + pMET2-1 | 17.3 | 15.1 | 13.6 | 5.5 | 46.4 | 16.1 |
| Y2224-ME⁻ + pMET2-2 | 16.2 | 15.1 | 13.3 | 5.6 | 46.2 | 16.4 |

ME deletion did not appear to have any effect on lipid production and fatty acid profile in a wild type *Yarrowia* context, as TFAs % DCW and % TFAs values were similar between wild type strain ATCC #20362 and Y2224-ME⁻+pBlue-YURA3 transformants (Table 7). This was a fair comparison given that, aside from the ME deletion, the Y2224-ME⁻ transformants only differed from ATCC #20362 at the URA3 locus and by containing a portion of the pBlue-YURA3 control vector.

The transformation of Y2224-ME⁻ strains with pME or pME-T2 allowed a comparison of the effects of overexpressing cytosolic ME or full length ME on lipid metabolism without any background effect by the native full length ME. Consistent with the results described above in which the lipid content was not significantly altered in strain Y2224 transformed with either pME or pME-T2, there was no apparent effect on lipid metabolism when either full length ME or cytosolic ME was overexpressed in Y2224-ME⁻ (Table 7).

Finally, in comparing the lipid profiles of the Y2224-ME⁻+pBlue-YURA3 transformants with the lipid profiles of the Y2224-ME⁻+pME or pME-T2 transformants, there was no significant effect on lipid content with the rescue of ME (cytosolic or full length) expression in Y2224. This is consistent with there being no discernible difference in lipid metabolism between ATCC #20362 and Y2224-ME⁻+pBlue-YURA3; i.e., if removing ME had no effect on lipid production, then adding ME back should likewise not have had any effect.

The results obtained herein with strain Y2224 altogether indicate that ME, whether full length or cytosolic, does not significantly affect lipid metabolism in *Yarrowia* that has not been modified for increased lipid production such as with transgenic strains Z1978U and Z5567U.

Example 4

Heterologous Co-expression of Polynucleotides Encoding Cytosolic Malic Enzyme and Malate Dehydrogenase in *Y. lipolytica*

This Example describes co-expressing polynucleotides, one encoding cytosolic ME and the other encoding malate dehydrogenase (MDH), in a heterologous manner in *Y. lipolytica*. This analysis is performed to determine whether MDH expression can augment the increase in lipid production that occurs when expressing cytosolic ME in *Y. lipolytica* that has a lipid content of at least about 35% of dry cell weight.

Primers YMDH1-F (SEQ ID NO:31) and YMDH1-R (SEQ ID NO:32) are used to PCR-amplify a polynucleotide encoding a *Y. lipolytica* mitochondrial MDH (SEQ ID NO:30). This polynucleotide is cloned into a vector such that it is contained within an expression cassette having suitable promoter and terminator sequences for expressing the polynucleotide in *Yarrowia*.

Transformation procedures are performed to co-express YIME-T2 and *Yarrowia* mitochondrial MDH in a *Y. lipolytica* strain that has a lipid content of at least about 35% of dry cell weight. The lipid profiles of transformants are measured as described above.

What is claimed is:

1. A transgenic *Yarrowia* species comprising:
   (i) a polynucleotide encoding a cytosolic malic enzyme;
   (ii) a lipid content that is at least about 35% by weight of the dry cell weight of said *Yarrowia* species; and
   (iii) an engineered polyunsaturated fatty acid (PUFA) biosynthetic pathway,
   wherein overexpression of the cytosolic malic enzyme increases lipid content.

2. The *Yarrowia* species of claim 1, wherein said cytosolic malic enzyme comprises a dysfunctional mitochondrial targeting sequence.

3. The *Yarrowia* species of claim 1, wherein said cytosolic malic enzyme does not comprise a mitochondrial targeting sequence.

4. The *Yarrowia* species of claim 1, wherein said cytosolic malic enzyme comprises an amino acid sequence having at least about 90% sequence identity to SEQ ID NO:5 and has malic enzyme activity.

5. The *Yarrowia* species of claim 1, wherein said lipid content is at least about 50% by weight of the dry cell weight of said *Yarrowia* species.

6. The *Yarrowia* species of claim 1, wherein said engineered PUFA biosynthetic pathway produces at least one PUFA selected from the group consisting of linoleic acid, alpha-linolenic acid, gamma-linolenic acid, stearidonic acid, eicosadienoic acid, dihomo-gamma-linolenic acid, arachidonic acid, eicosatrienoic acid, eicosatetraenoic acid, eicosapentaenoic acid, docosatetraenoic acid, omega-3 docosapentaenoic acid, omega-6 docosapentaenoic acid and docosahexaenoic acid.

7. The *Yarrowia* species of claim 6, wherein said engineered PUFA biosynthetic pathway produces eicosapentaenoic acid.

8. The *Yarrowia* species of claim 1, which species is *Yarrowia lipolytica*.

9. A method for increasing lipid content of a transgenic *Yarrowia* species that comprises:
   a) culturing the transgenic *Yarrowia* species of claim 1, wherein a microbial oil comprising at least one PUFA is produced, and
   b) optionally, recovering the microbial oil of step (a).

10. The method of claim 9, wherein said cytosolic malic enzyme comprises a dysfunctional mitochondrial targeting sequence.

11. The method of claim 9, wherein said cytosolic malic enzyme does not comprise a mitochondrial targeting sequence.

12. The method of claim 9, wherein said cytosolic malic enzyme comprises an amino acid sequence having at least about 90% sequence identity to SEQ ID NO:5 and has malic enzyme activity.

13. The method of claim 9, wherein said lipid content is at least about 50% by weight of the dry cell weight of said *Yarrowia* species.

14. The method of claim 1, wherein said engineered PUFA biosynthetic pathway produces at least one PUFA selected from the group consisting of linoleic acid, alpha-linolenic acid, gamma-linolenic acid, stearidonic acid, eicosadienoic acid, dihomo-gamma-linolenic acid, arachidonic acid, eicosatrienoic acid, eicosatetraenoic acid, eicosapentaenoic acid, docosatetraenoic acid, omega-3 docosapentaenoic acid, omega-6 docosapentaenoic acid, and docosahexaenoic acid.

15. The method of claim 14, wherein said engineered PUFA biosynthetic pathway produces eicosapentaenoic acid.

16. The *Yarrowia* species of claim 4, wherein said cytosolic malic enzyme comprises SEQ ID NO:5.

17. The *Yarrowia* species of claim 6, wherein said cytosolic malic enzyme comprises SEQ ID NO:5.

18. The method of claim 12, wherein said cytosolic malic enzyme comprises SEQ ID NO:5.

19. The method of claim 14, wherein said cytosolic malic enzyme comprises SEQ ID NO:5.

\* \* \* \* \*

SEQUENCE LISTING

<160> NUMBER OF SEQ ID NOS: 32

<210> SEQ ID NO 1
<211> LENGTH: 629
<212> TYPE: PRT
<213> ORGANISM: Yarrowia lipolytica
<220> FEATURE:
<221> NAME/KEY: MISC_FEATURE
<222> LOCATION: (1)..(629)
<223> OTHER INFORMATION: GenBank Accession No. XP_504112 (malic enzyme)

<400> SEQUENCE: 1

```
Met Leu Arg Leu Arg Thr Met Arg Pro Thr Gln Thr Ser Val Arg Ala
1               5                   10                  15

Ala Leu Gly Pro Thr Ala Ala Arg Asn Met Ser Ser Ser Pro
            20                  25                  30

Ser Ser Phe Glu Tyr Ser Ser Tyr Val Lys Gly Thr Arg Glu Ile Gly
        35                  40                  45

His Arg Lys Ala Pro Thr Thr Arg Leu Ser Val Glu Gly Pro Ile Tyr
    50                  55                  60

Val Gly Phe Asp Gly Ile Arg Leu Leu Asn Leu Pro His Leu Asn Lys
65                  70                  75                  80

Gly Ser Gly Phe Pro Leu Asn Glu Arg Glu Phe Arg Leu Ser Gly
                85                  90                  95

Leu Leu Pro Ser Ala Glu Ala Thr Leu Glu Glu Gln Val Asp Arg Ala
            100                 105                 110

Tyr Gln Gln Phe Lys Lys Cys Gly Thr Pro Leu Ala Lys Asn Gly Phe
        115                 120                 125

Cys Thr Ser Leu Lys Phe Gln Asn Glu Val Leu Tyr Tyr Ala Leu Leu
    130                 135                 140

Leu Lys His Val Lys Glu Val Phe Pro Ile Ile Tyr Thr Pro Thr Gln
145                 150                 155                 160

Gly Glu Ala Ile Glu Gln Tyr Ser Arg Leu Phe Arg Arg Pro Glu Gly
                165                 170                 175

Cys Phe Leu Asp Ile Thr Ser Pro Tyr Asp Val Glu Glu Arg Leu Gly
            180                 185                 190

Ala Phe Gly Asp His Asp Asp Ile Asp Tyr Ile Val Val Thr Asp Ser
        195                 200                 205

Glu Gly Ile Leu Gly Ile Gly Asp Gln Gly Val Gly Gly Ile Gly Ile
    210                 215                 220

Ser Ile Ala Lys Leu Ala Leu Met Thr Leu Cys Ala Gly Val Asn Pro
225                 230                 235                 240

Ser Arg Val Ile Pro Val Val Leu Asp Thr Gly Thr Asn Asn Gln Glu
                245                 250                 255

Leu Leu His Asp Pro Leu Tyr Leu Gly Arg Arg Met Pro Arg Val Arg
            260                 265                 270

Gly Lys Gln Tyr Asp Asp Phe Ile Asp Asn Phe Val Gln Ser Ala Arg
        275                 280                 285

Arg Leu Tyr Pro Lys Ala Val Ile His Phe Glu Asp Phe Gly Leu Ala
    290                 295                 300

Asn Ala His Lys Ile Leu Asp Lys Tyr Arg Pro Glu Ile Pro Cys Phe
305                 310                 315                 320

Asn Asp Asp Ile Gln Gly Thr Gly Ala Val Thr Leu Ala Ser Ile Thr
                325                 330                 335

Ala Ala Leu Lys Val Leu Gly Lys Asn Ile Thr Asp Thr Arg Ile Leu
            340                 345                 350
```

-continued

```
Val Tyr Gly Ala Gly Ser Ala Gly Met Gly Ile Ala Glu Gln Val Tyr
            355                 360                 365

Asp Asn Leu Val Ala Gln Gly Leu Asp Asp Lys Thr Ala Arg Gln Asn
    370                 375                 380

Ile Phe Leu Met Asp Arg Pro Gly Leu Leu Thr Thr Ala Leu Thr Asp
385                 390                 395                 400

Glu Gln Met Ser Asp Val Gln Lys Pro Phe Ala Lys Asp Lys Ala Asn
                405                 410                 415

Tyr Glu Gly Val Asp Thr Lys Thr Leu Glu His Val Val Ala Ala Val
            420                 425                 430

Lys Pro His Ile Leu Ile Gly Cys Ser Thr Gln Pro Gly Ala Phe Asn
        435                 440                 445

Glu Lys Val Val Lys Glu Met Leu Lys His Thr Pro Arg Pro Ile Ile
    450                 455                 460

Leu Pro Leu Ser Asn Pro Thr Arg Leu His Glu Ala Val Pro Ala Asp
465                 470                 475                 480

Leu Tyr Lys Trp Thr Asp Gly Lys Ala Leu Val Ala Thr Gly Ser Pro
                485                 490                 495

Phe Asp Pro Val Asn Gly Lys Glu Thr Ser Glu Asn Asn Asn Cys Phe
            500                 505                 510

Val Phe Pro Gly Ile Gly Leu Gly Ala Ile Leu Ser Arg Ser Lys Leu
        515                 520                 525

Ile Thr Asn Thr Met Ile Ala Ala Ile Glu Cys Leu Ala Glu Gln
    530                 535                 540

Ala Pro Ile Leu Lys Asn His Asp Glu Gly Val Leu Pro Asp Val Ala
545                 550                 555                 560

Leu Ile Gln Ile Ile Ser Ala Arg Val Ala Thr Ala Val Val Leu Gln
                565                 570                 575

Ala Lys Ala Glu Gly Leu Ala Thr Val Glu Glu Leu Lys Pro Gly
            580                 585                 590

Thr Lys Glu His Val Gln Ile Pro Asp Asn Phe Asp Glu Cys Leu Ala
        595                 600                 605

Trp Val Glu Thr Gln Met Trp Arg Pro Val Tyr Arg Pro Leu Ile His
    610                 615                 620

Val Arg Asp Tyr Asp
625

<210> SEQ ID NO 2
<211> LENGTH: 669
<212> TYPE: PRT
<213> ORGANISM: Saccharomyces cerevisiae
<220> FEATURE:
<221> NAME/KEY: MISC_FEATURE
<222> LOCATION: (1)..(669)
<223> OTHER INFORMATION: GenBank Accession No. EDN59877 (malic enzyme)

<400> SEQUENCE: 2

Met Leu Arg Thr Arg Leu Ser Val Ser Val Ala Ala Arg Ser Gln Leu
1               5                   10                  15

Thr Arg Ser Leu Thr Ala Ser Arg Thr Ala Pro Leu Arg Arg Trp Pro
            20                  25                  30

Ile Gln Gln Ser Arg Leu Tyr Ser Ser Asn Thr Arg Ser His Lys Ala
        35                  40                  45

Thr Thr Thr Arg Glu Asn Thr Phe Gln Lys Pro Tyr Ser Asp Glu Glu
    50                  55                  60
```

-continued

```
Val Thr Lys Thr Pro Val Gly Ser Arg Ala Arg Lys Ile Phe Glu Ala
 65                  70                  75                  80

Pro His Pro His Ala Thr Arg Leu Thr Val Glu Gly Ala Ile Glu Cys
                 85                  90                  95

Pro Leu Glu Ser Phe Gln Leu Leu Asn Ser Pro Leu Phe Asn Lys Gly
            100                 105                 110

Ser Ala Phe Thr Gln Glu Glu Arg Glu Ala Phe Asn Leu Glu Ala Leu
        115                 120                 125

Leu Pro Pro Gln Val Asn Thr Leu Asp Glu Gln Leu Glu Arg Ser Tyr
    130                 135                 140

Lys Gln Leu Cys Tyr Leu Lys Thr Pro Leu Ala Lys Asn Asp Phe Met
145                 150                 155                 160

Thr Ser Leu Arg Val Gln Asn Lys Val Leu Tyr Phe Ala Leu Ile Arg
                165                 170                 175

Lys His Ile Lys Glu Leu Val Pro Ile Ile Tyr Thr Pro Thr Glu Gly
            180                 185                 190

Asp Ala Ile Ala Ala Tyr Ser His Arg Phe Arg Lys Pro Glu Gly Val
        195                 200                 205

Phe Leu Asp Ile Thr Glu Pro Asp Ser Ile Glu Arg Arg Leu Ala Thr
    210                 215                 220

Tyr Gly Gly Asp Lys Asp Val Asp Tyr Ile Val Val Ser Asp Ser Glu
225                 230                 235                 240

Gly Ile Leu Gly Ile Gly Asp Gln Gly Ile Gly Gly Val Arg Ile Ala
                245                 250                 255

Ile Ser Lys Leu Ala Leu Met Thr Leu Cys Gly Gly Ile His Pro Gly
            260                 265                 270

Arg Val Leu Pro Val Cys Leu Asp Val Gly Thr Asn Asn Lys Lys Leu
        275                 280                 285

Ala Arg Asp Glu Leu Tyr Met Gly Asn Lys Phe Ser Arg Ile Arg Gly
    290                 295                 300

Lys Gln Tyr Asp Asp Phe Leu Glu Lys Phe Ile Lys Ala Val Lys Lys
305                 310                 315                 320

Val Tyr Pro Ser Ala Val Leu His Phe Glu Asp Phe Gly Val Lys Asn
                325                 330                 335

Ala Arg Arg Leu Leu Glu Lys Tyr Arg Tyr Glu Leu Pro Ser Phe Asn
            340                 345                 350

Asp Asp Ile Gln Gly Thr Gly Ala Val Val Met Ala Ser Leu Ile Ala
        355                 360                 365

Ala Leu Lys His Thr Asn Arg Asp Leu Lys Asp Thr Arg Val Leu Ile
    370                 375                 380

Tyr Gly Ala Gly Ser Ala Gly Leu Gly Ile Ala Asp Gln Ile Val Asn
385                 390                 395                 400

His Met Val Thr His Gly Val Asp Lys Glu Glu Ala Arg Lys Lys Ile
                405                 410                 415

Phe Leu Met Asp Arg Arg Gly Leu Ile Leu Gln Ser Tyr Glu Ala Asn
            420                 425                 430

Ser Thr Pro Ala Gln His Val Tyr Ala Lys Ser Asp Ala Glu Trp Ala
        435                 440                 445

Gly Ile Asn Thr Arg Ser Leu His Asp Val Val Glu Asn Val Lys Pro
    450                 455                 460

Thr Cys Leu Val Gly Cys Ser Thr Gln Ala Gly Ala Phe Thr Gln Asp
465                 470                 475                 480

Val Val Glu Glu Met His Lys His Asn Pro Arg Pro Ile Ile Phe Pro
```

-continued

```
                        485                 490                 495
Leu Ser Asn Pro Thr Arg Leu His Glu Ala Val Pro Ala Asp Leu Met
            500                 505                 510

Lys Trp Thr Asn Asn Asn Ala Leu Val Ala Thr Gly Ser Pro Phe Pro
        515                 520                 525

Pro Val Asp Gly Tyr Arg Ile Ser Glu Asn Asn Cys Tyr Ser Phe
    530                 535                 540

Pro Gly Ile Gly Leu Gly Ala Val Leu Ser Arg Ala Thr Thr Ile Thr
545                 550                 555                 560

Asp Lys Met Ile Ser Ala Ala Val Asp Gln Leu Ala Glu Leu Ser Pro
                565                 570                 575

Leu Arg Glu Gly Asp Ser Arg Pro Gly Leu Leu Pro Gly Leu Asp Thr
            580                 585                 590

Ile Thr Asn Thr Ser Ala Arg Leu Ala Thr Ala Val Ile Leu Gln Ala
        595                 600                 605

Leu Glu Glu Gly Thr Ala Arg Ile Glu Gln Glu Val Pro Gly Gly
    610                 615                 620

Ala Pro Gly Glu Thr Val Lys Val Pro Arg Asp Phe Asp Glu Cys Leu
625                 630                 635                 640

Gln Trp Val Lys Ala Gln Met Trp Glu Pro Val Tyr Arg Pro Met Ile
                645                 650                 655

Lys Val Gln His Asp Pro Ser Val His Thr Asn Gln Leu
            660                 665
```

<210> SEQ ID NO 3
<211> LENGTH: 565
<212> TYPE: PRT
<213> ORGANISM: Schizosaccharomyces pombe
<220> FEATURE:
<221> NAME/KEY: MISC_FEATURE
<222> LOCATION: (1)..(565)
<223> OTHER INFORMATION: GenBank Accession No. NP_587760 (malic enzyme)

<400> SEQUENCE: 3

```
Met Pro Ala Gly Thr Lys Glu Gln Ile Glu Cys Pro Leu Lys Gly Val
1               5                   10                  15

Thr Leu Leu Asn Ser Pro Arg Tyr Asn Lys Asp Thr Ala Phe Thr Pro
            20                  25                  30

Glu Glu Arg Gln Lys Phe Glu Ile Ser Ser Arg Leu Pro Pro Ile Val
        35                  40                  45

Glu Thr Leu Gln Gln Val Asp Arg Cys Tyr Asp Gln Tyr Lys Ala
    50                  55                  60

Ile Gly Asp Glu Pro Leu Gln Lys Asn Leu Tyr Leu Ser Gln Leu Ser
65                  70                  75                  80

Val Thr Asn Gln Thr Leu Phe Tyr Ala Leu Ile Ser Gln His Leu Ile
                85                  90                  95

Glu Met Ile Pro Ile Ile Tyr Thr Pro Thr Glu Gly Asp Ala Ile Lys
            100                 105                 110

Gln Phe Ser Asp Ile Tyr Arg Tyr Pro Glu Gly Cys Tyr Leu Asp Ile
        115                 120                 125

Asp His Asn Asp Leu Ser Tyr Ile Lys Gln Gln Leu Ser Glu Phe Gly
    130                 135                 140

Lys Ser Asp Ser Val Glu Tyr Ile Ile Thr Asp Ser Glu Gly Ile
145                 150                 155                 160

Leu Gly Ile Gly Asp Gln Gly Val Gly Gly Val Leu Ile Ser Val Ala
                165                 170                 175
```

```
Lys Gly His Leu Met Thr Leu Cys Ala Gly Leu Asp Pro Asn Arg Phe
            180                 185                 190

Leu Pro Ile Val Leu Asp Val Gly Thr Asn Asn Glu Thr His Arg Lys
        195                 200                 205

Asn His Gln Tyr Met Gly Leu Arg Lys Asp Arg Val Arg Gly Glu Gln
    210                 215                 220

Tyr Asp Ser Phe Leu Asp Asn Val Ile Lys Ala Ile Arg Glu Val Phe
225                 230                 235                 240

Pro Glu Ala Phe Ile His Phe Glu Asp Phe Gly Leu Ala Asn Ala Lys
                245                 250                 255

Arg Ile Leu Asp His Tyr Arg Pro Asp Ile Ala Cys Phe Asn Asp Asp
            260                 265                 270

Ile Gln Gly Thr Gly Ala Val Ala Leu Ala Ala Ile Ile Gly Ala Leu
        275                 280                 285

His Val Thr Lys Ser Pro Leu Thr Glu Gln Arg Ile Met Ile Phe Gly
    290                 295                 300

Ala Gly Thr Ala Gly Val Gly Ile Ala Asn Gln Ile Val Ala Gly Met
305                 310                 315                 320

Val Thr Asp Gly Leu Ser Leu Asp Lys Ala Arg Gly Asn Leu Phe Met
                325                 330                 335

Ile Asp Arg Cys Gly Leu Leu Leu Glu Arg His Ala Lys Ile Ala Thr
            340                 345                 350

Asp Gly Gln Lys Pro Phe Leu Lys Lys Asp Ser Asp Phe Lys Glu Val
        355                 360                 365

Pro Ser Gly Asp Ile Asn Leu Glu Ser Ala Ile Ala Leu Val Lys Pro
    370                 375                 380

Thr Ile Leu Leu Gly Cys Ser Gly Gln Pro Gly Lys Phe Thr Glu Lys
385                 390                 395                 400

Ala Ile Arg Glu Met Ser Lys His Val Glu Arg Pro Ile Ile Phe Pro
                405                 410                 415

Ile Ser Asn Pro Thr Thr Leu Met Glu Ala Lys Pro Asp Gln Ile Asp
            420                 425                 430

Lys Trp Ser Asp Gly Lys Ala Leu Ile Ala Thr Gly Ser Pro Leu Pro
        435                 440                 445

Pro Leu Asn Arg Asn Gly Lys Lys Tyr Val Ile Ser Gln Cys Asn Asn
    450                 455                 460

Ala Leu Leu Tyr Pro Ala Leu Gly Val Ala Cys Val Leu Ser Arg Cys
465                 470                 475                 480

Lys Leu Leu Ser Asp Gly Met Leu Lys Ala Ser Asp Ala Leu Ala
                485                 490                 495

Thr Val Pro Arg Ser Leu Phe Ala Ala Asp Glu Ala Leu Leu Pro Asp
            500                 505                 510

Leu Asn Asn Ala Arg Glu Ile Ser Arg His Ile Val Phe Ala Val Leu
        515                 520                 525

Lys Gln Ala Val Ser Glu Gly Met Ser Thr Val Asp Leu Pro Lys Asp
    530                 535                 540

Asp Ala Lys Leu Lys Glu Trp Ile Ile Glu Arg Glu Trp Asn Pro Glu
545                 550                 555                 560

Tyr Lys Pro Phe Val
                565

<210> SEQ ID NO 4
<211> LENGTH: 1737
```

<212> TYPE: DNA
<213> ORGANISM: Artificial sequence
<220> FEATURE:
<223> OTHER INFORMATION: Cytosolic malic enzyme, YlME-T2 (used in pME-T2 construct)
<220> FEATURE:
<221> NAME/KEY: CDS
<222> LOCATION: (1)..(1737)

<400> SEQUENCE: 4

```
atg gct aca acc cgt ctg tcg gtt gag ggc ccc atc tac gtg ggc ttc      48
Met Ala Thr Thr Arg Leu Ser Val Glu Gly Pro Ile Tyr Val Gly Phe
1               5                   10                  15 gac ggc att cgt ctt ctc aac ctg ccg cat ctc aac aag ggc tcg gga      96
Asp Gly Ile Arg Leu Leu Asn Leu Pro His Leu Asn Lys Gly Ser Gly
                20                  25                  30 ttc ccc ctc aac gag cga cgg gaa ttc aga ctc agt ggt ctt ctg ccc     144
Phe Pro Leu Asn Glu Arg Arg Glu Phe Arg Leu Ser Gly Leu Leu Pro
            35                  40                  45 tct gcc gaa gcc acc ctg gag gaa cag gtc gac cga gca tac caa caa     192
Ser Ala Glu Ala Thr Leu Glu Glu Gln Val Asp Arg Ala Tyr Gln Gln
        50                  55                  60 ttc aaa aag tgt ggc act ccc tta gcc aaa aac ggg ttc tgc acc tcg     240
Phe Lys Lys Cys Gly Thr Pro Leu Ala Lys Asn Gly Phe Cys Thr Ser
65                  70                  75                  80 ctc aag ttc caa aac gag gtg ctc tac tac gcc ctg ctc aag cac         288
Leu Lys Phe Gln Asn Glu Val Leu Tyr Tyr Ala Leu Leu Leu Lys His
                85                  90                  95 gtt aag gag gtc ttc ccc atc atc tat aca ccg act cag gga gaa gcc     336
Val Lys Glu Val Phe Pro Ile Ile Tyr Thr Pro Thr Gln Gly Glu Ala
                100                 105                 110 att gaa cag tac tcg cgg ctg ttc cgg cgg ccc gaa ggc tgc ttc ctc     384
Ile Glu Gln Tyr Ser Arg Leu Phe Arg Arg Pro Glu Gly Cys Phe Leu
            115                 120                 125 gac atc acc agt ccc tac gac gtg gag gag cgt ctg gga gcg ttt gga     432
Asp Ile Thr Ser Pro Tyr Asp Val Glu Glu Arg Leu Gly Ala Phe Gly
        130                 135                 140 gac cat gac gac att gac tac att gtc gtg act gac tcc gag ggt att     480
Asp His Asp Asp Ile Asp Tyr Ile Val Val Thr Asp Ser Glu Gly Ile
145                 150                 155                 160 ctc gga att gga gac caa gga gtg ggc ggt att ggt att tcc atc gcc     528
Leu Gly Ile Gly Asp Gln Gly Val Gly Gly Ile Gly Ile Ser Ile Ala
                165                 170                 175 aag ctg gct ctc atg act cta tgt gct gga gtc aac ccc tca cga gtc     576
Lys Leu Ala Leu Met Thr Leu Cys Ala Gly Val Asn Pro Ser Arg Val
                180                 185                 190 att cct gtg gtt ctg gat acg gga acc aac aac cag gag ctg ctg cac     624
Ile Pro Val Val Leu Asp Thr Gly Thr Asn Asn Gln Glu Leu Leu His
            195                 200                 205 gac ccc ctg tat ctc ggc cga cga atg ccc cga gtg cga gga aag cag     672
Asp Pro Leu Tyr Leu Gly Arg Arg Met Pro Arg Val Arg Gly Lys Gln
        210                 215                 220 tac gac gac ttc atc gac aac ttt gtg cag tct gcc cga agg ctg tat     720
Tyr Asp Asp Phe Ile Asp Asn Phe Val Gln Ser Ala Arg Arg Leu Tyr
225                 230                 235                 240 ccc aag gcg gtg atc cat ttc gag gac ttt ggg ctc gct aac gca cac     768
Pro Lys Ala Val Ile His Phe Glu Asp Phe Gly Leu Ala Asn Ala His
                245                 250                 255 aag atc ctc gac aag tat cga ccg gag atc ccc tgc ttc aac gac gac     816
Lys Ile Leu Asp Lys Tyr Arg Pro Glu Ile Pro Cys Phe Asn Asp Asp
                260                 265                 270
```

| | | |
|---|---|---|
| atc cag ggc act gga gcc gtc act ttg gcc tcc atc acg gcc gct ctc<br>Ile Gln Gly Thr Gly Ala Val Thr Leu Ala Ser Ile Thr Ala Ala Leu<br>275 280 285 | | 864 |
| aag gtg ctg ggc aaa aat atc aca gat act cga att ctc gtg tac gga<br>Lys Val Leu Gly Lys Asn Ile Thr Asp Thr Arg Ile Leu Val Tyr Gly<br>290 295 300 | | 912 |
| gct ggt tcg gcc ggc atg ggt att gct gaa cag gtc tat gat aac ctg<br>Ala Gly Ser Ala Gly Met Gly Ile Ala Glu Gln Val Tyr Asp Asn Leu<br>305 310 315 320 | | 960 |
| gtt gcc cag ggt ctc gac gac aag act gcg cga caa aac atc ttt ctc<br>Val Ala Gln Gly Leu Asp Asp Lys Thr Ala Arg Gln Asn Ile Phe Leu<br>325 330 335 | | 1008 |
| atg gac cga ccg ggt cta ctg acc acc gca ctt acc gac gag cag atg<br>Met Asp Arg Pro Gly Leu Leu Thr Thr Ala Leu Thr Asp Glu Gln Met<br>340 345 350 | | 1056 |
| agc gac gtg cag aag ccg ttt gcc aag gac aag gcc aat tac gag gga<br>Ser Asp Val Gln Lys Pro Phe Ala Lys Asp Lys Ala Asn Tyr Glu Gly<br>355 360 365 | | 1104 |
| gtg gac acc aag act ctg gag cac gtg gtt gct gcc gtc aag ccc cat<br>Val Asp Thr Lys Thr Leu Glu His Val Val Ala Ala Val Lys Pro His<br>370 375 380 | | 1152 |
| att ctc att gga tgt tcc act cag ccc ggc gcc ttt aac gag aag gtc<br>Ile Leu Ile Gly Cys Ser Thr Gln Pro Gly Ala Phe Asn Glu Lys Val<br>385 390 395 400 | | 1200 |
| gtc aag gag atg ctc aaa cac acc cct cga ccc atc att ctc cct ctt<br>Val Lys Glu Met Leu Lys His Thr Pro Arg Pro Ile Ile Leu Pro Leu<br>405 410 415 | | 1248 |
| tcc aac ccc aca cgt ctt cat gag gct gtc cct gca gat ctg tac aag<br>Ser Asn Pro Thr Arg Leu His Glu Ala Val Pro Ala Asp Leu Tyr Lys<br>420 425 430 | | 1296 |
| tgg acc gac ggc aag gct ctg gtt gcc acc ggc tcg ccc ttt gac cca<br>Trp Thr Asp Gly Lys Ala Leu Val Ala Thr Gly Ser Pro Phe Asp Pro<br>435 440 445 | | 1344 |
| gtc aac ggc aag gag acg tct gag aac aat aac tgc ttt gtt ttc ccc<br>Val Asn Gly Lys Glu Thr Ser Glu Asn Asn Asn Cys Phe Val Phe Pro<br>450 455 460 | | 1392 |
| gga atc ggg ctg gga gcc att ctg tct cga tca aag ctc atc acc aac<br>Gly Ile Gly Leu Gly Ala Ile Leu Ser Arg Ser Lys Leu Ile Thr Asn<br>465 470 475 480 | | 1440 |
| acc atg att gct gct gcc atc gag tgc ctc gcc gaa cag gcc ccc att<br>Thr Met Ile Ala Ala Ala Ile Glu Cys Leu Ala Glu Gln Ala Pro Ile<br>485 490 495 | | 1488 |
| ctc aag aac cac gac gag gga gta ctt ccc gac gta gct ctc atc cag<br>Leu Lys Asn His Asp Glu Gly Val Leu Pro Asp Val Ala Leu Ile Gln<br>500 505 510 | | 1536 |
| atc att tcg gcc cgg gtg gcc act gcc gtg gtt ctt cag gcc aag gct<br>Ile Ile Ser Ala Arg Val Ala Thr Ala Val Val Leu Gln Ala Lys Ala<br>515 520 525 | | 1584 |
| gag ggc cta gcc act gtc gag gaa gag ctc aag ccc ggc acc aag gaa<br>Glu Gly Leu Ala Thr Val Glu Glu Glu Leu Lys Pro Gly Thr Lys Glu<br>530 535 540 | | 1632 |
| cat gtg cag att ccc gac aac ttt gac gag tgt ctc gcc tgg gtc gag<br>His Val Gln Ile Pro Asp Asn Phe Asp Glu Cys Leu Ala Trp Val Glu<br>545 550 555 560 | | 1680 |
| act cag atg tgg cgg ccc gtc tac cgg cct ctc atc cat gtg cgg gat<br>Thr Gln Met Trp Arg Pro Val Tyr Arg Pro Leu Ile His Val Arg Asp<br>565 570 575 | | 1728 |
| tac gac tag<br>Tyr Asp | | 1737 |

```
<210> SEQ ID NO 5
<211> LENGTH: 578
<212> TYPE: PRT
<213> ORGANISM: Artificial sequence
<220> FEATURE:
<223> OTHER INFORMATION: Synthetic Construct

<400> SEQUENCE: 5

Met Ala Thr Thr Arg Leu Ser Val Glu Gly Pro Ile Tyr Val Gly Phe
1               5                   10                  15

Asp Gly Ile Arg Leu Leu Asn Leu Pro His Leu Asn Lys Gly Ser Gly
            20                  25                  30

Phe Pro Leu Asn Glu Arg Arg Glu Phe Arg Leu Ser Gly Leu Leu Pro
        35                  40                  45

Ser Ala Glu Ala Thr Leu Glu Glu Gln Val Asp Arg Ala Tyr Gln Gln
    50                  55                  60

Phe Lys Lys Cys Gly Thr Pro Leu Ala Lys Asn Gly Phe Cys Thr Ser
65                  70                  75                  80

Leu Lys Phe Gln Asn Glu Val Leu Tyr Tyr Ala Leu Leu Leu Lys His
                85                  90                  95

Val Lys Glu Val Phe Pro Ile Ile Tyr Thr Pro Thr Gln Gly Glu Ala
            100                 105                 110

Ile Glu Gln Tyr Ser Arg Leu Phe Arg Arg Pro Glu Gly Cys Phe Leu
        115                 120                 125

Asp Ile Thr Ser Pro Tyr Asp Val Glu Glu Arg Leu Gly Ala Phe Gly
    130                 135                 140

Asp His Asp Asp Ile Asp Tyr Ile Val Val Thr Asp Ser Glu Gly Ile
145                 150                 155                 160

Leu Gly Ile Gly Asp Gln Gly Val Gly Gly Ile Gly Ile Ser Ile Ala
                165                 170                 175

Lys Leu Ala Leu Met Thr Leu Cys Ala Gly Val Asn Pro Ser Arg Val
            180                 185                 190

Ile Pro Val Val Leu Asp Thr Gly Thr Asn Asn Gln Glu Leu Leu His
        195                 200                 205

Asp Pro Leu Tyr Leu Gly Arg Arg Met Pro Arg Val Arg Gly Lys Gln
    210                 215                 220

Tyr Asp Asp Phe Ile Asp Asn Phe Val Gln Ser Ala Arg Arg Leu Tyr
225                 230                 235                 240

Pro Lys Ala Val Ile His Phe Glu Asp Phe Gly Leu Ala Asn Ala His
                245                 250                 255

Lys Ile Leu Asp Lys Tyr Arg Pro Glu Ile Pro Cys Phe Asn Asp Asp
            260                 265                 270

Ile Gln Gly Thr Gly Ala Val Thr Leu Ala Ser Ile Thr Ala Ala Leu
        275                 280                 285

Lys Val Leu Gly Lys Asn Ile Thr Asp Thr Arg Ile Leu Val Tyr Gly
    290                 295                 300

Ala Gly Ser Ala Gly Met Gly Ile Ala Glu Gln Val Tyr Asp Asn Leu
305                 310                 315                 320

Val Ala Gln Gly Leu Asp Asp Lys Thr Ala Arg Gln Asn Ile Phe Leu
                325                 330                 335

Met Asp Arg Pro Gly Leu Leu Thr Thr Ala Leu Thr Asp Glu Gln Met
            340                 345                 350

Ser Asp Val Gln Lys Pro Phe Ala Lys Asp Lys Ala Asn Tyr Glu Gly
        355                 360                 365
```

```
Val Asp Thr Lys Thr Leu Glu His Val Val Ala Ala Val Lys Pro His
    370                 375                 380

Ile Leu Ile Gly Cys Ser Thr Gln Pro Gly Ala Phe Asn Glu Lys Val
385                 390                 395                 400

Val Lys Glu Met Leu Lys His Thr Pro Arg Pro Ile Ile Leu Pro Leu
                405                 410                 415

Ser Asn Pro Thr Arg Leu His Glu Ala Val Pro Ala Asp Leu Tyr Lys
            420                 425                 430

Trp Thr Asp Gly Lys Ala Leu Val Ala Thr Gly Ser Pro Phe Asp Pro
        435                 440                 445

Val Asn Gly Lys Glu Thr Ser Glu Asn Asn Cys Phe Val Phe Pro
    450                 455                 460

Gly Ile Gly Leu Gly Ala Ile Leu Ser Arg Ser Lys Leu Ile Thr Asn
465                 470                 475                 480

Thr Met Ile Ala Ala Ile Glu Cys Leu Ala Glu Gln Ala Pro Ile
                485                 490                 495

Leu Lys Asn His Asp Glu Gly Val Leu Pro Asp Val Ala Leu Ile Gln
                500                 505                 510

Ile Ile Ser Ala Arg Val Ala Thr Ala Val Val Leu Gln Ala Lys Ala
            515                 520                 525

Glu Gly Leu Ala Thr Val Glu Glu Leu Lys Pro Gly Thr Lys Glu
    530                 535                 540

His Val Gln Ile Pro Asp Asn Phe Asp Glu Cys Leu Ala Trp Val Glu
545                 550                 555                 560

Thr Gln Met Trp Arg Pro Val Tyr Arg Pro Leu Ile His Val Arg Asp
                565                 570                 575

Tyr Asp
```

<210> SEQ ID NO 6
<211> LENGTH: 1890
<212> TYPE: DNA
<213> ORGANISM: Artificial sequence
<220> FEATURE:
<223> OTHER INFORMATION: Malic enzyme, YlME (used in pME construct)
<220> FEATURE:
<221> NAME/KEY: CDS
<222> LOCATION: (1)..(1890)

<400> SEQUENCE: 6

```
atg gta cga cta cga acc atg cga ccc aca cag acc agc gtc agg gcg    48
Met Val Arg Leu Arg Thr Met Arg Pro Thr Gln Thr Ser Val Arg Ala
1               5                   10                  15 gcg ctt ggg ccc acc gcc gcg gcc cga aac atg tcc tcc tcc agc ccc    96
Ala Leu Gly Pro Thr Ala Ala Ala Arg Asn Met Ser Ser Ser Ser Pro
                20                  25                  30 tcc agc ttc gaa tac tcg tcc tac gtc aag ggc acg cgg gaa atc ggc    144
Ser Ser Phe Glu Tyr Ser Ser Tyr Val Lys Gly Thr Arg Glu Ile Gly
            35                  40                  45 cac cga aag gcg ccc aca acc cgt ctg tcg gtt gag ggc ccc atc tac    192
His Arg Lys Ala Pro Thr Thr Arg Leu Ser Val Glu Gly Pro Ile Tyr
        50                  55                  60 gtg ggc ttc gac ggc att cgt ctt ctc aac ctg ccg cat ctc aac aag    240
Val Gly Phe Asp Gly Ile Arg Leu Leu Asn Leu Pro His Leu Asn Lys
65                  70                  75                  80 ggc tcg gga ttc ccc ctc aac gag cga cgg gaa ttc aga ctc agt ggt    288
Gly Ser Gly Phe Pro Leu Asn Glu Arg Arg Glu Phe Arg Leu Ser Gly
                85                  90                  95 ctt ctg ccc tct gcc gaa gcc acc ctg gag gaa cag gtc gac cga gca    336
```

```
Leu Leu Pro Ser Ala Glu Ala Thr Leu Glu Glu Gln Val Asp Arg Ala
            100                 105                 110 tac caa caa ttc aaa aag tgt ggc act ccc tta gcc aaa aac ggg ttc      384
Tyr Gln Gln Phe Lys Lys Cys Gly Thr Pro Leu Ala Lys Asn Gly Phe
            115                 120                 125 tgc acc tcg ctc aag ttc caa aac gag gtg ctc tac tac gcc ctg ctg      432
Cys Thr Ser Leu Lys Phe Gln Asn Glu Val Leu Tyr Tyr Ala Leu Leu
    130                 135                 140 ctc aag cac gtt aag gag gtc ttc ccc atc atc tat aca ccg act cag      480
Leu Lys His Val Lys Glu Val Phe Pro Ile Ile Tyr Thr Pro Thr Gln
145                 150                 155                 160 gga gaa gcc att gaa cag tac tcg cgg ctg ttc cgg cgg ccc gaa ggc      528
Gly Glu Ala Ile Glu Gln Tyr Ser Arg Leu Phe Arg Arg Pro Glu Gly
                165                 170                 175 tgc ttc ctc gac atc acc agt ccc tac gac gtg gag gag cgt ctg gga      576
Cys Phe Leu Asp Ile Thr Ser Pro Tyr Asp Val Glu Glu Arg Leu Gly
                180                 185                 190 gcg ttt gga gac cat gac gac att gac tac att gtc gtg act gac tcc      624
Ala Phe Gly Asp His Asp Asp Ile Asp Tyr Ile Val Val Thr Asp Ser
                195                 200                 205 gag ggt att ctc gga att gga gac caa gga gtg ggc ggt att ggt att      672
Glu Gly Ile Leu Gly Ile Gly Asp Gln Gly Val Gly Gly Ile Gly Ile
    210                 215                 220 tcc atc gcc aag ctg gct ctc atg act cta tgt gct gga gtc aac ccc      720
Ser Ile Ala Lys Leu Ala Leu Met Thr Leu Cys Ala Gly Val Asn Pro
225                 230                 235                 240 tca cga gtc att cct gtg gtt ctg gat acg gga acc aac aac cag gag      768
Ser Arg Val Ile Pro Val Val Leu Asp Thr Gly Thr Asn Asn Gln Glu
                245                 250                 255 ctg ctg cac gac ccc ctg tat ctc ggc cga cga atg ccc cga gtg cga      816
Leu Leu His Asp Pro Leu Tyr Leu Gly Arg Arg Met Pro Arg Val Arg
                260                 265                 270 gga aag cag tac gac gac ttc atc gac aac ttt gtg cag tct gcc cga      864
Gly Lys Gln Tyr Asp Asp Phe Ile Asp Asn Phe Val Gln Ser Ala Arg
                275                 280                 285 agg ctg tat ccc aag gcg gtg atc cat ttc gag gac ttt ggg ctc gct      912
Arg Leu Tyr Pro Lys Ala Val Ile His Phe Glu Asp Phe Gly Leu Ala
    290                 295                 300 aac gca cac aag atc ctc gac aag tat cga ccg gag atc ccc tgc ttc      960
Asn Ala His Lys Ile Leu Asp Lys Tyr Arg Pro Glu Ile Pro Cys Phe
305                 310                 315                 320 aac gac gac atc cag ggc act gga gcc gtc act ttg gcc tcc atc acg     1008
Asn Asp Asp Ile Gln Gly Thr Gly Ala Val Thr Leu Ala Ser Ile Thr
                325                 330                 335 gcc gct ctc aag gtg ctg ggc aaa aat atc aca gat act cga att ctc     1056
Ala Ala Leu Lys Val Leu Gly Lys Asn Ile Thr Asp Thr Arg Ile Leu
                340                 345                 350 gtg tac gga gct ggt tcg gcc ggc atg ggt att gct gaa cag gtc tat     1104
Val Tyr Gly Ala Gly Ser Ala Gly Met Gly Ile Ala Glu Gln Val Tyr
    355                 360                 365 gat aac ctg gtt gcc cag ggt ctc gac gac aag act gcg cga caa aac     1152
Asp Asn Leu Val Ala Gln Gly Leu Asp Asp Lys Thr Ala Arg Gln Asn
            370                 375                 380 atc ttt ctc atg gac cga ccg ggt cta ctg acc acc gca ctt acc gac     1200
Ile Phe Leu Met Asp Arg Pro Gly Leu Leu Thr Thr Ala Leu Thr Asp
385                 390                 395                 400 gag cag atg agc gac gtg cag aag ccg ttt gcc aag gac aag gcc aat     1248
Glu Gln Met Ser Asp Val Gln Lys Pro Phe Ala Lys Asp Lys Ala Asn
                405                 410                 415
```

| | | | | | | | | | | | | | | | | |
|---|---|---|---|---|---|---|---|---|---|---|---|---|---|---|---|---|
| tac | gag | gga | gtg | gac | acc | aag | act | ctg | gag | cac | gtg | gtt | gct | gcc | gtc | 1296 |
| Tyr | Glu | Gly | Val | Asp | Thr | Lys | Thr | Leu | Glu | His | Val | Val | Ala | Ala | Val | |
| | | | 420 | | | | 425 | | | | 430 | | | | | |
| aag | ccc | cat | att | ctc | att | gga | tgt | tcc | act | cag | ccc | ggc | gcc | ttt | aac | 1344 |
| Lys | Pro | His | Ile | Leu | Ile | Gly | Cys | Ser | Thr | Gln | Pro | Gly | Ala | Phe | Asn | |
| | | 435 | | | | | 440 | | | | | 445 | | | | |
| gag | aag | gtc | gtc | aag | gag | atg | ctc | aaa | cac | acc | cct | cga | ccc | atc | att | 1392 |
| Glu | Lys | Val | Val | Lys | Glu | Met | Leu | Lys | His | Thr | Pro | Arg | Pro | Ile | Ile | |
| | 450 | | | | | 455 | | | | | 460 | | | | | |
| ctc | cct | ctt | tcc | aac | ccc | aca | cgt | ctt | cat | gag | gct | gtc | cct | gca | gat | 1440 |
| Leu | Pro | Leu | Ser | Asn | Pro | Thr | Arg | Leu | His | Glu | Ala | Val | Pro | Ala | Asp | |
| 465 | | | | | 470 | | | | | 475 | | | | | 480 | |
| ctg | tac | aag | tgg | acc | gac | ggc | aag | gct | ctg | gtt | gcc | acc | ggc | tcg | ccc | 1488 |
| Leu | Tyr | Lys | Trp | Thr | Asp | Gly | Lys | Ala | Leu | Val | Ala | Thr | Gly | Ser | Pro | |
| | | | | 485 | | | | | 490 | | | | | 495 | | |
| ttt | gac | cca | gtc | aac | ggc | aag | gag | acg | tct | gag | aac | aat | aac | tgc | ttt | 1536 |
| Phe | Asp | Pro | Val | Asn | Gly | Lys | Glu | Thr | Ser | Glu | Asn | Asn | Asn | Cys | Phe | |
| | | | 500 | | | | | 505 | | | | | 510 | | | |
| gtt | ttc | ccc | gga | atc | ggg | ctg | gga | gcc | att | ctg | tct | cga | tca | aag | ctc | 1584 |
| Val | Phe | Pro | Gly | Ile | Gly | Leu | Gly | Ala | Ile | Leu | Ser | Arg | Ser | Lys | Leu | |
| | | 515 | | | | | 520 | | | | | 525 | | | | |
| atc | acc | aac | acc | atg | att | gct | gct | gcc | atc | gag | tgc | ctc | gcc | gaa | cag | 1632 |
| Ile | Thr | Asn | Thr | Met | Ile | Ala | Ala | Ala | Ile | Glu | Cys | Leu | Ala | Glu | Gln | |
| | 530 | | | | | 535 | | | | | 540 | | | | | |
| gcc | ccc | att | ctc | aag | aac | cac | gac | gag | gga | gta | ctt | ccc | gac | gta | gct | 1680 |
| Ala | Pro | Ile | Leu | Lys | Asn | His | Asp | Glu | Gly | Val | Leu | Pro | Asp | Val | Ala | |
| 545 | | | | | 550 | | | | | 555 | | | | | 560 | |
| ctc | atc | cag | atc | att | tcg | gcc | cgg | gtg | gcc | act | gcc | gtg | gtt | ctt | cag | 1728 |
| Leu | Ile | Gln | Ile | Ile | Ser | Ala | Arg | Val | Ala | Thr | Ala | Val | Val | Leu | Gln | |
| | | | | 565 | | | | | 570 | | | | | 575 | | |
| gcc | aag | gct | gag | ggc | cta | gcc | act | gtc | gag | gaa | gag | ctc | aag | ccc | ggc | 1776 |
| Ala | Lys | Ala | Glu | Gly | Leu | Ala | Thr | Val | Glu | Glu | Glu | Leu | Lys | Pro | Gly | |
| | | | 580 | | | | | 585 | | | | | 590 | | | |
| acc | aag | gaa | cat | gtg | cag | att | ccc | gac | aac | ttt | gac | gag | tgt | ctc | gcc | 1824 |
| Thr | Lys | Glu | His | Val | Gln | Ile | Pro | Asp | Asn | Phe | Asp | Glu | Cys | Leu | Ala | |
| | | 595 | | | | | 600 | | | | | 605 | | | | |
| tgg | gtc | gag | act | cag | atg | tgg | cgg | ccc | gtc | tac | cgg | cct | ctc | atc | cat | 1872 |
| Trp | Val | Glu | Thr | Gln | Met | Trp | Arg | Pro | Val | Tyr | Arg | Pro | Leu | Ile | His | |
| | 610 | | | | | 615 | | | | | 620 | | | | | |
| gtg | cgg | gat | tac | gac | tag | | | | | | | | | | | 1890 |
| Val | Arg | Asp | Tyr | Asp | | | | | | | | | | | | |
| 625 | | | | | | | | | | | | | | | | |

<210> SEQ ID NO 7
<211> LENGTH: 629
<212> TYPE: PRT
<213> ORGANISM: Artificial sequence
<220> FEATURE:
<223> OTHER INFORMATION: Synthetic Construct

<400> SEQUENCE: 7

Met Val Arg Leu Arg Thr Met Arg Pro Thr Gln Thr Ser Val Arg Ala
1               5                   10                  15

Ala Leu Gly Pro Thr Ala Ala Arg Asn Met Ser Ser Ser Pro
            20                  25                  30

Ser Ser Phe Glu Tyr Ser Ser Tyr Val Lys Gly Thr Arg Glu Ile Gly
            35                  40                  45

His Arg Lys Ala Pro Thr Thr Arg Leu Ser Val Glu Gly Pro Ile Tyr
        50                  55                  60

Val Gly Phe Asp Gly Ile Arg Leu Leu Asn Leu Pro His Leu Asn Lys

```
                65                  70                  75                  80
        Gly Ser Gly Phe Pro Leu Asn Glu Arg Arg Glu Phe Arg Leu Ser Gly
                            85                  90                  95
        Leu Leu Pro Ser Ala Glu Ala Thr Leu Glu Glu Gln Val Asp Arg Ala
                        100                 105                 110
        Tyr Gln Gln Phe Lys Lys Cys Gly Thr Pro Leu Ala Lys Asn Gly Phe
                        115                 120                 125
        Cys Thr Ser Leu Lys Phe Gln Asn Glu Val Leu Tyr Tyr Ala Leu Leu
                    130                 135                 140
        Leu Lys His Val Lys Glu Val Phe Pro Ile Ile Tyr Thr Pro Thr Gln
        145                 150                 155                 160
        Gly Glu Ala Ile Glu Gln Tyr Ser Arg Leu Phe Arg Arg Pro Glu Gly
                            165                 170                 175
        Cys Phe Leu Asp Ile Thr Ser Pro Tyr Asp Val Glu Glu Arg Leu Gly
                        180                 185                 190
        Ala Phe Gly Asp His Asp Asp Ile Asp Tyr Ile Val Val Thr Asp Ser
                    195                 200                 205
        Glu Gly Ile Leu Gly Ile Gly Asp Gln Gly Val Gly Gly Ile Gly Ile
        210                 215                 220
        Ser Ile Ala Lys Leu Ala Leu Met Thr Leu Cys Ala Gly Val Asn Pro
        225                 230                 235                 240
        Ser Arg Val Ile Pro Val Val Leu Asp Thr Gly Thr Asn Asn Gln Glu
                            245                 250                 255
        Leu Leu His Asp Pro Leu Tyr Leu Gly Arg Arg Met Pro Arg Val Arg
                        260                 265                 270
        Gly Lys Gln Tyr Asp Asp Phe Ile Asp Asn Phe Val Gln Ser Ala Arg
                        275                 280                 285
        Arg Leu Tyr Pro Lys Ala Val Ile His Phe Glu Asp Phe Gly Leu Ala
                    290                 295                 300
        Asn Ala His Lys Ile Leu Asp Lys Tyr Arg Pro Glu Ile Pro Cys Phe
        305                 310                 315                 320
        Asn Asp Asp Ile Gln Gly Thr Gly Ala Val Thr Leu Ala Ser Ile Thr
                            325                 330                 335
        Ala Ala Leu Lys Val Leu Gly Lys Asn Ile Thr Asp Thr Arg Ile Leu
                        340                 345                 350
        Val Tyr Gly Ala Gly Ser Ala Gly Met Gly Ile Ala Glu Gln Val Tyr
                        355                 360                 365
        Asp Asn Leu Val Ala Gln Gly Leu Asp Asp Lys Thr Ala Arg Gln Asn
                    370                 375                 380
        Ile Phe Leu Met Asp Arg Pro Gly Leu Leu Thr Thr Ala Leu Thr Asp
        385                 390                 395                 400
        Glu Gln Met Ser Asp Val Gln Lys Pro Phe Ala Lys Asp Lys Ala Asn
                            405                 410                 415
        Tyr Glu Gly Val Asp Thr Lys Thr Leu Glu His Val Val Ala Ala Val
                        420                 425                 430
        Lys Pro His Ile Leu Ile Gly Cys Ser Thr Gln Pro Gly Ala Phe Asn
                        435                 440                 445
        Glu Lys Val Val Lys Glu Met Leu Lys His Thr Pro Arg Pro Ile Ile
                    450                 455                 460
        Leu Pro Leu Ser Asn Pro Thr Arg Leu His Glu Ala Val Pro Ala Asp
        465                 470                 475                 480
        Leu Tyr Lys Trp Thr Asp Gly Lys Ala Leu Val Ala Thr Gly Ser Pro
                            485                 490                 495
```

```
Phe Asp Pro Val Asn Gly Lys Glu Thr Ser Glu Asn Asn Cys Phe
            500                 505                 510
Val Phe Pro Gly Ile Gly Leu Gly Ala Ile Leu Ser Arg Ser Lys Leu
            515                 520                 525
Ile Thr Asn Thr Met Ile Ala Ala Ile Glu Cys Leu Ala Glu Gln
            530                 535                 540
Ala Pro Ile Leu Lys Asn His Asp Glu Gly Val Leu Pro Asp Val Ala
545                 550                 555                 560
Leu Ile Gln Ile Ile Ser Ala Arg Val Ala Thr Ala Val Val Leu Gln
                565                 570                 575
Ala Lys Ala Glu Gly Leu Ala Thr Val Glu Glu Leu Lys Pro Gly
            580                 585                 590
Thr Lys Glu His Val Gln Ile Pro Asp Asn Phe Asp Glu Cys Leu Ala
            595                 600                 605
Trp Val Glu Thr Gln Met Trp Arg Pro Val Tyr Arg Pro Leu Ile His
            610                 615                 620
Val Arg Asp Tyr Asp
625
```

```
<210> SEQ ID NO 8
<211> LENGTH: 33
<212> TYPE: DNA
<213> ORGANISM: Artificial sequence
<220> FEATURE:
<223> OTHER INFORMATION: Primer ME-TN2

<400> SEQUENCE: 8
gatcccatgg ctacaacccg tctgtcggtt gag                          33

<210> SEQ ID NO 9
<211> LENGTH: 33
<212> TYPE: DNA
<213> ORGANISM: Artificial sequence
<220> FEATURE:
<223> OTHER INFORMATION: Primer ME-T2

<400> SEQUENCE: 9
gatcgcggcc gctgcttact aaactaaact gtc                          33

<210> SEQ ID NO 10
<211> LENGTH: 8986
<212> TYPE: DNA
<213> ORGANISM: Artificial sequence
<220> FEATURE:
<223> OTHER INFORMATION: Plasmid construct pMET2

<400> SEQUENCE: 10
ggccgcaagt gtggatgggg aagtgagtgc ccggttctgt gtgcacaatt ggcaatccaa    60
gatggatgga ttcaacacag ggatatagcg agctacgtgg tggtgcgagg atatagcaac   120
ggatatttat gtttgacact tgagaatgta cgatacaagc actgtccaag tacaatacta   180
aacatactgt acatactcat actcgtaccc gggcaacggt ttcacttgag tgcagtggct   240
agtgctctta ctcgtacagt gtgcaatact gcgtatcata gtctttgatg tatatcgtat   300
tcattcatgt tagttgcgta cgggcgtcgt tgcttgtgtg attttttgagg acccatccct   360 ttggtatata agtatactct ggggttaagg ttgcccgtgt agtctaggtt atagtttttca   420 tgtgaaatac cgagagccga gggagaataa acggggggtat ttggacttgt ttttttcgcg   480
gaaaagcgtc gaatcaaccc tgcgggcctt gcaccatgtc cacgacgtgt ttctcgcccc   540
```

```
aattcgcccc ttgcacgtca aaattaggcc tccatctaga cccctccata acatgtgact    600
gtggggaaaa gtataaggga aaccatgcaa ccatagacga cgtgaaagac ggggaggaac    660
caatggaggc caaagaaatg gggtagcaac agtccaggag acagacaagg agacaaggag    720
agggcgcccg aaagatcgga aaaacaaaca tgtccaattg gggcagtgac ggaaacgaca    780
cggacacttc agtacaatgg accgaccatc tccaagccag ggttattccg gtatcacctt    840
ggccgtaacc tcccgctggt acctgatatt gtacacgttc acattcaata actttcagc    900 tacaataaga gaggctgttt gtcgggcatg tgtgtccgtc gtatggggtg atgtccgagg    960
gcgaaattcg ctacaagctt aactctggcg cttgtccagt atgaatagac aagtcaagac   1020
cagtggtgcc atgattgaca gggaggtaca agacttcgat actcgagcat tactcggact   1080
tgtggcgatt gaacagacgg cgatcgctt ctccccgta ttgccggcgc gccagctgca    1140
ttaatgaatc ggccaacgcg cggggagagg cggtttgcgt attgggcgct cttccgcttc   1200
ctcgctcact gactcgctgc gctcggtcgt tcggctgcgg cgagcggtat cagctcactc   1260
aaaggcggta atacggttat ccacagaatc aggggataac gcaggaaaga acatgtgagc   1320
aaaaggccag caaaaggcca ggaaccgtaa aaaggccgcg ttgctggcgt ttttccatag   1380
gctccgcccc cctgacgagc atcacaaaaa tcgacgctca agtcagaggt ggcgaaaccc   1440
gacaggacta taaagatacc aggcgtttcc ccctggaagc tccctcgtgc gctctcctgt   1500
tccgaccctg ccgcttaccg gatacctgtc cgcctttctc ccttcgggaa gcgtggcgct   1560
ttctcatagc tcacgctgta ggtatctcag ttcggtgtag tcgttcgct ccaagctggg   1620 ctgtgtgcac gaaccccccg ttcagcccga ccgctgcgcc ttatccggta actatcgtct   1680
tgagtccaac ccggtaagac acgacttatc gccactggca gcagccactg gtaacaggat   1740
tagcagagcg aggtatgtag cggtgctac agagttcttg aagtggtggc ctaactacgg    1800
ctacactaga agaacagtat ttggtatctg cgctctgctg aagccagtta ccttcggaaa   1860
aagagttggt agctcttgat ccggcaaaca aaccaccgct ggtagcggtg tttttttgt    1920 ttgcaagcag cagattacgc gcagaaaaaa aggatctcaa gaagatcctt tgatcttttc   1980 tacgggtct gacgctcagt ggaacgaaaa ctcacgttaa gggattttgg tcatgagatt    2040
atcaaaaagg atcttcacct agatcctttt aaattaaaaa tgaagtttta aatcaatcta   2100
aagtatatat gagtaaactt ggtctgacag ttaccaatgc ttaatcagtg aggcacctat   2160
ctcagcgatc tgtctatttc gttcatccat agttgcctga ctccccgtcg tgtagataac   2220 tacgatacg gagggcttac catctggccc cagtgctgca atgataccgc gagacccacg    2280
ctcaccggct ccagatttat cagcaataaa ccagccagcc ggaagggccg agcgcagaag   2340
tggtcctgca actttatccg cctccatcca gtctattaat tgttgccggg aagctagagt   2400
aagtagttcg ccagttaata gtttgcgcaa cgttgttgcc attgctacag gcatcgtggt   2460
gtcacgctcg tcgtttggta tggcttcatt cagctccggt tcccaacgat caaggcgagt   2520
tacatgatcc cccatgttgt gcaaaaaagc ggttagctcc ttcggtcctc cgatcgttgt   2580
cagaagtaag ttggccgcag tgttatcact catggttatg gcagcactgc ataattctct   2640
tactgtcatg ccatccgtaa gatgcttttc tgtgactggt gagtactcaa ccaagtcatt   2700
ctgagaatag tgtatgcggc gaccgagttg ctcttgcccg gcgtcaatac gggataatac   2760
cgcgccacat agcagaactt taaaagtgct catcattgga aaacgttctt cggggcgaaa   2820
actctcaagg atcttaccgc tgttgagatc cagttcgatg taacccactc gtgcacccaa   2880
```

```
ctgatcttca gcatctttta ctttcaccag cgtttctggg tgagcaaaaa caggaaggca   2940
aaatgccgca aaaagggaa taagggcgac acggaaatgt tgaatactca tactcttcct   3000
ttttcaatat tattgaagca tttatcaggg ttattgtctc atgagcggat acatatttga   3060
atgtatttag aaaaataaac aaatagggt tccgcgcaca tttccccgaa aagtgccacc    3120
tgatgcggtg tgaaataccg cacagatgcg taaggagaaa ataccgcatc aggaaattgt   3180
aagcgttaat attttgttaa aattcgcgtt aaattttgt taaatcagct cattttttaa    3240
ccaataggcc gaaatcggca aaatccctta taatcaaaa gaatagaccg atatagggtt    3300
gagtgttgtt ccagtttgga acaagagtcc actattaaag aacgtggact ccaacgtcaa   3360
agggcgaaaa accgtctatc agggcgatgg cccactacgt gaaccatcac cctaatcaag   3420
ttttttgggg tcgaggtgcc gtaaagcact aaatcggaac cctaaaggga gcccccgatt   3480
tagagcttga cggggaaagc cggcgaacgt ggcgagaaag gaagggaaga aagcgaaagg   3540
agcgggcgct agggcgctgg caagtgtagc ggtcacgctg cgcgtaacca ccacacccgc   3600
cgcgcttaat gcgccgctac agggcgcgtc cattcgccat tcaggctgcg caactgttgg   3660
gaagggcgat cggtgcgggc ctcttcgcta ttacgccagc tggcgaaagg gggatgtgct   3720
gcaaggcgat taagttgggt aacgccaggg ttttcccagt cacgacgttg taaaacgacg   3780
gccagtgaat tgtaatacga ctcactatag ggcgaattgg gcccgacgtc gcatgcgctg   3840
atgcactttt ggtctgaaag agatgcattt tgaatcccaa acttgcagtg cccagtgac    3900 atacatctcc gcgttttgga aaatgttcag aaacagttga ttgtgttgga atggggaatg   3960
gggaatggaa aaatgactca agtatcaatt ccaaaaactt ctctggctgg cagtacctac   4020
tgtccatact actgcatttt ctccagtcag gccactctat actcgacgac acagtagtaa   4080
aacccagata atttcgacat aaacaagaaa acagacccaa taatatttat atatagtcag   4140
ccgtttgtcc agttcagact gtaatagccg aaaaaaaatc caaagtttct attctaggaa   4200
aatatattcc aatattttta attcttaatc tcatttattt tattctagcg aaatacattt    4260
cagctacttg agacatgtga tacccacaaa tcggattcgg actcggttgt tcagaagagc   4320
atatggcatt cgtgctcgct tgttcacgta ttcttcctgt tccatctctt ggccgacaat   4380
cacacaaaaa tggggttttt tttttaattc taatgattca ttacagcaaa attgagatat   4440
agcagaccac gtattccata atcaccaagg aagttcttgg gcgtcttaat taagtcatac   4500
acaagtcagc tttcttcgag cctcatataa gtataagtag ttcaacgtat tagcactgta   4560
cccagcatct ccgtatcgag aaacacaaca acatgcccca ttggacagat catgcggata   4620
cacaggttgt gcagtatcat acatactcga tcagacaggt cgtctgacca tcatacaagc   4680
tgaacaagcg ctccatactt gcacgctctc tatatacaca gttaaattac atatccatag   4740
tctaacctct aacagttaat cttctggtaa gcctcccagc cagccttctg gtatcgcttg   4800
gcctcctcaa taggatctcg gttctggccg tacagacctc ggccgacaat tatgatatcc   4860
gttccggtag acatgacatc ctcaacagtt cggtactgct gtccgagagc gtctcccttg   4920
tcgtcaagac ccaccccggg ggtcagaata agccagtcct cagagtcgcc cttaggtcgg   4980
ttctgggcaa tgaagccaac cacaaactcg ggtcggatc gggcaagctc aatggtctgc    5040
ttggagtact cgccagtggc cagagagccc ttgcaagaca gctcggccag catgagcaga   5100
cctctggcca gcttctcgtt gggagagggg actaggaact ccttgtactg ggagttctcg   5160
tagtcagaga cgtcctcctt cttctgttca gagacagttt cctcggcacc agctcgcagg   5220
ccagcaatga ttccggttcc gggtacaccg tgggcgttgg tgatatcgga ccactcggcg   5280
```

```
attcggtgac accggtactg gtgcttgaca gtgttgccaa tatctgcgaa ctttctgtcc    5340
tcgaacagga agaaaccgtg cttaagagca agttccttga gggggagcac agtgccggcg    5400
taggtgaagt cgtcaatgat gtcgatatgg gttttgatca tgcacacata aggtccgacc    5460
ttatcggcaa gctcaatgag ctccttggtg gtggtaacat ccagagaagc acacaggttg    5520
gttttcttgg ctgccacgag cttgagcact cgagcggcaa aggcggactt gtggacgtta    5580
gctcgagctt cgtaggaggg cattttggtg gtgaagagga gactgaaata aatttagtct    5640
gcagaacttt ttatcggaac cttatctggg gcagtgaagt atatgttatg gtaatagtta    5700
cgagttagtt gaacttatag atagactgga ctatacggct atcggtccaa attagaaaga    5760
acgtcaatgg ctctctgggc gtcgcctttg ccgacaaaaa tgtgatcatg atgaaagcca    5820
gcaatgacgt tgcagctgat attgttgtcg gccaaccgcg ccgaaaacgc agctgtcaga    5880
cccacagcct ccaacgaaga atgtatcgtc aaagtgatcc aagcacactc atagttggag    5940
tcgtactcca aaggcggcaa tgacgagtca gacagatact cgtcgactca ggcgacgacg    6000
gaattcctgc agcccatctg cagaattcag gagagaccgg gttggcggcg tatttgtgtc    6060
ccaaaaaaca gccccaattg ccccggagaa gacggccagg ccgcctagat gacaaattca    6120
acaactcaca gctgactttc tgccattgcc actagggggg ggccttttta tatggccaag    6180
ccaagctctc cacgtcggtt gggctgcacc caacaataaa tgggtagggt tgcaccaaca    6240
aagggatggg atgggggta gaagatacga ggataacggg gctcaatggc acaaataaga    6300
acgaatactg ccattaagac tcgtgatcca gcgactgaca ccattgcatc atctaagggc    6360
ctcaaaacta cctcggaact gctgcgctga tctggacacc acagaggttc cgagcacttt    6420
aggttgcacc aaatgtccca ccaggtgcag gcagaaaacg ctggaacagc gtgtacagtt    6480
tgtcttaaca aaaagtgagg gcgctgaggt cgagcagggt ggtgtgactt gttatagcct    6540
ttagagctgc gaaagcgcgt atggatttgg ctcatcaggc cagattgagg gtctgtggac    6600
acatgtcatg ttagtgtact tcaatcgccc cctggatata gccccgacaa taggccgtgg    6660
cctcattttt ttgccttccg cacatttcca ttgctcggta cccacacctt gcttctcctg    6720
cacttgccaa ccttaatact ggtttacatt gaccaacatc ttacaagcgg ggggcttgtc    6780
tagggtatat ataaacagtg gctctcccaa tcggttgcca gtctcttttt tcctttcttt    6840
ccccacagat tcgaaatcta aactacacat cacacaatgc ctgttactga cgtccttaag    6900
cgaaagtccg gtgtcatcgt cggcgacgat gtccgagccg tgagtatcca cgacaagatc    6960
agtgtcgaga cgacgcgttt tgtgtaatga cacaatccga aagtcgctag caacacacac    7020
tctctacaca aactaaccca gctctccatg gctacaaccc gtctgtcggt tgagggcccc    7080
atctacgtgg gcttcgacgg cattcgtctt ctcaacctgc cgcatctcaa caagggctcg    7140
ggattccccc tcaacgagcg acgggaattc agactcagtg gtcttctgcc ctctgccgaa    7200
gccaccctgg aggaacaggt cgaccgagca taccaacaat tcaaaaagtg tggcactccc    7260
ttagccaaaa acgggttctg cacctcgctc aagttccaaa acgaggtgct ctactacgcc    7320
ctgctgctca gcacgttaa ggaggtcttc cccatcatct atacaccgac tcagggagaa    7380
gccattgaac agtactcgcg gctgttccgg cggcccgaag gctgcttcct cgacatcacc    7440
agtccctacg acgtggagga gcgtctggga gcgtttggag accatgacga cattgactac    7500
attgtcgtga ctgactccga gggtattctc ggaattggag accaaggagt gggcggtatt    7560
ggtatttcca tcgccaagct ggctctcatg actctatgtg ctggagtcaa cccctcacga    7620
```

```
gtcattcctg tggttctgga tacgggaacc aacaaccagg agctgctgca cgaccccctg    7680
tatctcggcc gacgaatgcc ccgagtgcga ggaaagcagt acgacgactt catcgacaac    7740
tttgtgcagt ctgcccgaag gctgtatccc aaggcggtga tccatttcga ggactttggg    7800
ctcgctaacg cacacaagat cctcgacaag tatcgaccgg agatcccctg cttcaacgac    7860
gacatccagg gcactggagc cgtcactttg gcctccatca cggccgctct caaggtgctg    7920
ggcaaaaata tcacagatac tcgaattctc gtgtacggag ctggttcggc cggcatgggt    7980
attgctgaac aggtctatga taacctggtt gcccagggtc tcgacgacaa gactgcgcga    8040
caaaacatct ttctcatgga ccgacccgggt ctactgacca ccgcacttac cgacgagcag    8100
atgagcgacg tgcagaagcc gtttgccaag gacaaggcca attacgaggg agtggacacc    8160
aagactctgg agcacgtggt tgctgccgtc aagcccccata ttctcattgg atgttccact    8220
cagcccggcg cctttaacga aaggtcgtc aaggagatgc tcaaacacac ccctcgaccc    8280
atcattctcc ctcttttccaa ccccacacgt cttcatgagg ctgtccctgc agatctgtac    8340
aagtggaccg acggcaaggc tctggttgcc accggctcgc cctttgaccc agtcaacggc    8400
aaggagacgt ctgagaacaa taactgcttt gttttccccg gaatcgggct gggagccatt    8460
ctgtctcgat caaagctcat caccaacacc atgattgctg ctgccatcga gtgcctcgcc    8520
gaacaggccc ccattctcaa gaaccacgac gagggagtac ttcccgacgt agctctcatc    8580
cagatcattt cggcccgggt ggccactgcc gtggttcttc aggccaaggc tgagggccta    8640
gccactgtcg aggaagagct caagcccggc accaaggaac atgtgcagat tcccgacaac    8700
tttgacgagt gtctcgcctg gtcgagact cagatgtggc ggcccgtcta ccggcctctc    8760
atccatgtgc gggattacga ctagagcgtg gaatagtgga atacagcttg ataacacagc    8820
gttgatcaga gtgagtccga gaagagtcca taggagtcca ttgaagagtc cattggagag    8880
tccattggag tccagtggcg gaccatagta gtcgacagta gttgatagta gtactggtag    8940
atgaatgtat tatcggcgcc agtgacagtt tagtttagta agcagc                  8986
```

<210> SEQ ID NO 11
<211> LENGTH: 31
<212> TYPE: DNA
<213> ORGANISM: Artificial sequence
<220> FEATURE:
<223> OTHER INFORMATION: Primer ME-F

<400> SEQUENCE: 11

```
aaccatggta cggctacgaa ccatgcgacc c                                    31
```

<210> SEQ ID NO 12
<211> LENGTH: 34
<212> TYPE: DNA
<213> ORGANISM: Artificial sequence
<220> FEATURE:
<223> OTHER INFORMATION: Primer ME-R

<400> SEQUENCE: 12

```
aagcggccgc ctagtcgtaa tcccgcacat ggat                                 34
```

<210> SEQ ID NO 13
<211> LENGTH: 8938
<212> TYPE: DNA
<213> ORGANISM: Artificial sequence
<220> FEATURE:
<223> OTHER INFORMATION: Plasmid construct pME

<400> SEQUENCE: 13

-continued

```
gtacgggcgt cgttgcttgt gtgattttg aggacccatc cctttggtat ataagtatac      60
tctggggtta aggttgcccg tgtagtctag gttatagttt tcatgtgaaa taccgagagc    120
cgagggagaa taaacggggg tatttggact tgttttttc gcggaaaagc gtcgaatcaa    180
ccctgcgggc cttgcaccat gtccacgacg tgttctcgc cccaattcgc cccttgcacg    240
tcaaaattag gcctccatct agacccctcc ataacatgtg actgtgggga aagtataag    300 ggaaaccatg caaccataga cgacgtgaaa gacgggagg aaccaatgga ggccaaagaa    360
atggggtagc aacagtccag gagacagaca aggagacaag gagagggcgc ccgaaagatc    420
ggaaaaacaa acatgtccaa ttggggcagt gacggaaacg acacggacac ttcagtacaa    480
tggaccgacc atctccaagc cagggttatt ccggtatcac cttggccgta acctcccgct    540
ggtacctgat attgtacacg ttcacattca atatactttc agctacaata agagaggctg    600
tttgtcgggc atgtgtgtcc gtcgtatggg gtgatgtccg agggcgaaat tcgctacaag    660
cttaactctg gcgcttgtcc agtatgaata gacaagtcaa gaccagtggt gccatgattg    720
acagggaggt acaagacttc gatactcgag cattactcgg acttgtggcg attgaacaga    780
cgggcgatcg cttctccccc gtattgccgg cgcgccagct gcattaatga atcgccaac    840 gcgcggggag aggcggtttg cgtattgggc gctcttccgc ttcctcgctc actgactcgc    900
tgcgctcggt cgttcggctg cggcgagcgg tatcagctca ctcaaaggcg gtaatacggt    960
tatccacaga atcagggat aacgcaggaa agaacatgtg agcaaaaggc cagcaaaagg   1020
ccaggaaccg taaaaaggcc gcgttgctgg cgtttttcca taggctccgc cccctgacg   1080 agcatcacaa aaatcgacgc tcaagtcaga ggtggcgaaa cccgacagga ctataaagat   1140
accaggcgtt tccccctgga agctccctcg tgcgctctcc tgttccgacc ctgccgctta   1200
ccggatacct gtccgccttt ctcccttcgg gaagcgtggc gctttctcat agctcacgct   1260
gtaggtatct cagttcggtg taggtcgttc gctccaagct gggctgtgtg cacgaaccc   1320 ccgttcagcc cgaccgctgc gccttatccg gtaactatcg tcttgagtcc aacccggtaa   1380
gacacgactt atcgccactg gcagcagcca ctggtaacag gattagcaga gcgaggtatg   1440
taggcggtgc tacagagttc ttgaagtggt ggcctaacta cggctacact agaagaacag   1500
tatttggtat ctgcgctctg ctgaagccag ttaccttcgg aaaaagagtt ggtagctctt   1560
gatccggcaa acaaaccacc gctggtagcg gtggtttttt tgtttgcaag cagcagatta   1620
cgcgcagaaa aaaaggatct caagaagatc ctttgatctt ttctacgggg tctgacgctc   1680
agtggaacga aaactcacgt taagggattt tggtcatgag attatcaaaa aggatcttca   1740
cctagatcct tttaaattaa aaatgaagtt ttaaatcaat ctaaagtata tatgagtaaa   1800
cttggtctga cagttaccaa tgcttaatca gtgaggcacc tatctcagcg atctgtctat   1860
ttcgttcatc catagttgcc tgactccccg tcgtgtagat aactacgata cgggagggct   1920
taccatctgg ccccagtgct gcaatgatac cgcgagaccc acgctcaccg gctccagatt   1980
tatcagcaat aaaccagcca gccggaaggg ccgagcgcag aagtggtcct gcaactttat   2040
ccgcctccat ccagtctatt aattgttgcc gggaagctag agtaagtagt tcgccagtta   2100
atagtttgcg caacgttgtt gccattgcta caggcatcgt ggtgtcacgc tcgtcgtttg   2160
gtatggcttc attcagctcc ggttcccaac gatcaaggcg agttacatga tcccccatgt   2220
tgtgcaaaaa agcggttagc tccttcggtc ctccgatcgt tgtcagaagt aagttggccg   2280
cagtgttatc actcatggtt atggcagcac tgcataattc tcttactgtc atgccatccg   2340
```

```
taagatgctt ttctgtgact ggtgagtact caaccaagtc attctgagaa tagtgtatgc    2400
ggcgaccgag ttgctcttgc ccggcgtcaa tacgggataa taccgcgcca catagcagaa    2460
ctttaaaagt gctcatcatt ggaaaacgtt cttcggggcg aaaactctca aggatcttac    2520
cgctgttgag atccagttcg atgtaaccca ctcgtgcacc caactgatct tcagcatctt    2580
ttactttcac cagcgtttct gggtgagcaa aaacaggaag gcaaaatgcc gcaaaaaagg    2640
gaataagggc gacacggaaa tgttgaatac tcatactctt ccttttcaa tattattgaa     2700
gcatttatca gggttattgt ctcatgagcg gatacatatt tgaatgtatt tagaaaaata    2760
aacaaatagg ggttccgcgc acatttcccc gaaaagtgcc acctgatgcg gtgtgaaata    2820
ccgcacagat gcgtaaggag aaaataccgc atcaggaaat tgtaagcgtt aatattttgt    2880
taaaattcgc gttaaatttt tgttaaatca gctcattttt taaccaatag gccgaaatcg    2940
gcaaaatccc ttataaatca aagaataga ccgagatagg gttgagtgtt gttccagttt     3000
ggaacaagag tccactatta agaacgtgg actccaacgt caaagggcga aaaccgtct     3060
atcagggcga tggcccacta cgtgaaccat caccctaatc aagttttttg gggtcgaggt    3120
gccgtaaagc actaaatcgg aaccctaaag ggagccccg atttagagct tgacggggaa    3180
agccggcgaa cgtggcgaga aaggaaggga agaaagcgaa aggagcgggc gctagggcgc    3240
tggcaagtgt agcggtcacg ctgcgcgtaa ccaccacacc cgccgcgctt aatgcgccgc    3300
tacagggcgc gtccattcgc cattcaggct gcgcaactgt tgggaagggc gatcggtgcg    3360
ggcctcttcg ctattacgcc agctggcgaa aggggatgt gctgcaaggc gattaagttg     3420
ggtaacgcca gggttttccc agtcacgacg ttgtaaaacg acggccagtg aattgtaata    3480
cgactcacta tagggcgaat tgggcccgac gtcgcatgcg ctgatgacac tttggtctga    3540
aagagatgca ttttgaatcc caaacttgca gtgcccaagt gacatacatc tccgcgtttt    3600
ggaaaatgtt cagaaacagt tgattgtgtt ggaatgggga atgggaatg gaaaatgac     3660
tcaagtatca attccaaaaa cttctctggc tggcagtacc tactgtccat actactgcat    3720
tttctccagt caggccactc tatactcgac gacacagtag taaaacccag ataatttcga    3780
cataaacaag aaaacagacc caataatatt tatatatagt cagccgtttg tccagttcag    3840
actgtaatag ccgaaaaaaa atccaaagtt tctattctag gaaaatatat tccaatattt    3900
ttaattctta atctcatta ttttattcta gcgaaataca tttcagctac ttgagacatg     3960
tgatacccac aaatcggatt cggactcggt tgttcagaag agcatatggc attcgtgctc    4020
gcttgttcac gtattcttcc tgttccatct cttggccgac aatcacacaa aaatgggtt     4080
ttttttttaa ttctaatgat tcattacagc aaaattgaga tatagcagac cacgtattcc    4140
ataatcacca aggaagttct tgggcgtctt aattaagtca tacacaagtc agctttcttc    4200
gagcctcata taagtataag tagttcaacg tattagcact gtacccagca tctccgtatc    4260
gagaaacaca acaacatgcc ccattggaca gatcatgcgg atacacaggt tgtgcagtat    4320
catacatact cgatcagaca ggtcgtctga ccatcataca agctgaacaa gcgctccata    4380
cttgcacgct ctctatatac acagttaaat tacatatcca tagtctaacc tctaacagtt    4440
aatcttctgg taagcctccc agccagcctt ctggtatcgc ttggcctcct caataggatc    4500
tcggttctgg ccgtacagac ctcggccgac aattatgata tccgttccgg tagacatgac    4560
atcctcaaca gttcggtact gctgtccgag agcgtctccc ttgtcgtcaa gacccacccc    4620
gggggtcaga ataagccagt cctcagagtc gcccttaggt cggttctggg caatgaagcc    4680
aaccacaaac tcggggtcgg atcgggcaag ctcaatggtc tgcttggagt actcgccagt    4740
```

```
ggccagagag cccttgcaag acagctcggc cagcatgagc agacctctgg ccagcttctc    4800
gttgggagag gggactagga actccttgta ctgggagttc tcgtagtcag agacgtcctc    4860
cttcttctgt tcagagacag tttcctcggc accagctcgc aggccagcaa tgattccggt    4920
tccgggtaca ccgtgggcgt tggtgatatc ggaccactcg gcgattcggt gacaccggta    4980
ctggtgcttg acagtgttgc caatatctgc gaactttctg tcctcgaaca ggaagaaacc    5040
gtgcttaaga gcaagttcct tgaggggag cacagtgccg gcgtaggtga agtcgtcaat     5100
gatgtcgata tgggttttga tcatgcacac ataaggtccg accttatcgg caagctcaat    5160
gagctccttg gtggtggtaa catccagaga agcacacagg ttggttttct tggctgccac    5220
gagcttgagc actcgagcgg caaaggcgga cttgtggacg ttagctcgag cttcgtagga    5280
gggcattttg gtggtgaaga ggagactgaa ataaatttag tctgcagaac tttttatcgg    5340
aaccttatct ggggcagtga agtatatgtt atggtaatag ttacgagtta gttgaactta    5400
tagatagact ggactatacg gctatcggtc caaattagaa agaacgtcaa tggctctctg    5460
ggcgtcgcct ttgccgacaa aaatgtgatc atgatgaaag ccagcaatga cgttgcagct    5520
gatattgttg tcgccaacc cgccgaaaa cgcagctgtc agaccacag cctccaacga       5580 agaatgtatc gtcaaagtga tccaagcaca ctcatagttg gagtcgtact ccaaaggcgg    5640
caatgacgag tcagacagat actcgtcgac tcaggcgacg acggaattcc tgcagcccat    5700
ctgcagaatt caggagagac cgggttggcg gcgtatttgt gtcccaaaaa acagccccaa    5760
ttgccccgga gaagacggcc aggccgccta gatgacaaat tcaacaactc acagctgact    5820
ttctgccatt gccactaggg gggggccttt ttatatggcc aagccaagct ctccacgtcg    5880
gttgggctgc acccaacaat aaatgggtag ggttgcacca acaaagggat gggatggggg    5940
gtagaagata cgaggataac ggggctcaat ggcacaaata agaacgaata ctgccattaa    6000
gactcgtgat ccagcgactg acaccattgc atcatctaag ggcctcaaaa ctacctcgga    6060
actgctgcgc tgatctggac accacagagg ttccgagcac tttaggttgc accaaatgtc    6120
ccaccaggtg caggcagaaa acgctggaac agcgtgtaca gtttgtctta acaaaaagtg    6180
agggcgctga ggtcgagcag ggtggtgtga cttgttatag cctttagagc tgcgaaagcg    6240
cgtatggatt tggctcatca ggccagattg agggtctgtg gacacatgtc atgttagtgt    6300
acttcaatcg cccctggat atagcccga caataggccg tggcctcatt tttttgcctt       6360
ccgcacattt ccattgctcg gtacccacac cttgcttctc ctgcacttgc caaccttaat    6420
actggtttac attgaccaac atcttacaag cgggggggctt gtctagggta tatataaaca   6480
gtggctctcc caatcggttg ccagtctctt ttttcctttc tttccccaca gattcgaaat    6540
ctaaactaca catcacacaa tgcctgttac tgacgtcctt aagcgaaagt ccggtgtcat    6600
cgtcggcgac gatgtccgag ccgtgagtat ccacgacaag atcagtgtcg agacgacgcg    6660
ttttgtgtaa tgacacaatc cgaaagtcgc tagcaacaca cactctctac acaaactaac    6720
ccagctctcc atggtacgac tacgaaccat gcgacccaca cagaccagcg tcagggcggc    6780
gcttgggccc accgccgcgg cccgaaacat gtcctcctcc agcccctcca gcttcgaata    6840
ctcgtcctac gtcaagggca cgcgggaaat cggccaccga aaggcgccca caacccgtct    6900
gtcggttgag ggccccatct acgtgggctt cgacggcatt cgtcttctca acctgccgca    6960
tctcaacaag ggctcgggat tccccctcaa cgagcgacgg gaattcagac tcagtggtct    7020
tctgccctct gccgaagcca ccctggagga acaggtcgac cgagcatacc aacaattcaa    7080
```

-continued

```
aaagtgtggc actcccttag ccaaaaacgg gttctgcacc tcgctcaagt tccaaaacga      7140
ggtgctctac tacgccctgc tgctcaagca cgttaaggag gtcttcccca tcatctatac      7200
accgactcag ggagaagcca ttgaacagta ctcgcggctg ttccggcggc ccgaaggctg      7260
cttcctcgac atcaccagtc cctacgacgt ggaggagcgt ctgggagcgt ttggagacca      7320
tgacgacatt gactacattg tcgtgactga ctccgagggt attctcggaa ttggagacca      7380
aggagtgggc ggtattggta tttccatcgc caagctggct ctcatgactc tatgtgctgg      7440
agtcaacccc tcacgagtca ttcctgtggt tctggatacg ggaaccaaca accaggagct      7500
gctgcacgac cccctgtatc tcggccgacg aatgccccga gtgcgaggaa agcagtacga      7560
cgacttcatc gacaactttg tgcagtctgc ccgaaggctg tatcccaagg cggtgatcca      7620
tttcgaggac tttgggctcg ctaacgcaca caagatcctc gacaagtatc gaccggagat      7680
cccctgcttc aacgacgaca tccagggcac tggagccgtc actttggcct ccatcacggc      7740
cgctctcaag gtgctgggca aaatatcac agatactcga attctcgtgt acggagctgg      7800
ttcggccggc atgggtattg ctgaacaggt ctatgataac ctggttgccc agggtctcga      7860
cgacaagact gcgcgacaaa acatctttct catggaccga ccgggtctac tgaccaccgc      7920
acttaccgac gagcagatga gcgacgtgca gaagccgttt gccaaggaca aggccaatta      7980
cgagggagtg gacaccaaga ctctggagca cgtggttgct gccgtcaagc cccatattct      8040
cattggatgt tccactcagc ccggcgcctt aacgagaag gtcgtcaagg atgctcaa      8100
acacacccct cgacccatca ttctccctct ttccaacccc acacgtcttc atgaggctgt      8160
ccctgcagat ctgtacaagt ggaccgacg caaggctctg gttgccaccg gctcgccctt      8220
tgacccagtc aacggcaagg agacgtctga gaacaataac tgctttgttt tccccggaat      8280
cgggctggga gccattctgt ctcgatcaaa gctcatcacc aacaccatga ttgctgctgc      8340
catcgagtgc ctcgccgaac aggccccat tctcaagaac cacgacgagg gagtacttcc      8400
cgacgtagct ctcatccaga tcatttcggc ccggtggcc actgccgtgg ttcttcaggc      8460
caaggctgag ggcctagcca ctgtcgagga agagctcaag cccggcacca aggaacatgt      8520
gcagattccc gacaactttg acgagtgtct cgcctgggtc gagactcaga gtgcggcc      8580
cgtctaccgg cctctcatcc atgtgcggga ttacgactag cggccgcaag tgtggatggg      8640
gaagtgagtg cccggttctg tgtgcacaat tggcaatcca agatggatgg attcaacaca      8700
gggatatagc gagctacgtg gtggtgcgag gatatagcaa cggatatta tgtttgacac      8760
ttgagaatgt acgatacaag cactgtccaa gtacaatact aaacatactg tacatactca      8820
tactcgtacc cgggcaacgg tttcacttga gtgcagtggc tagtgctctt actcgtacag      8880
tgtgcaatac tgcgtatcat agtctttgat gtatatcgta ttcattcatg ttagttgc      8938
```

<210> SEQ ID NO 14
<211> LENGTH: 4604
<212> TYPE: DNA
<213> ORGANISM: Artificial sequence
<220> FEATURE:
<223> OTHER INFORMATION: Plasmid construct pBlue-YURA3

<400> SEQUENCE: 14

```
ggccgctcta gaactagtgg atcccccggg ctgcaggaat tcctttacct gcaggataac       60
ttcgtataat gtatgctata cgaagttatg atctctctct tgagcttttc cataacaagt      120
tcttctgcct ccaggaagtc catggtggt ttgatcatgg ttttggtgta gtggtagtgc      180
agtggtggta ttgtgactgg ggatgtagtt gagaataagt catacacaag tcagctttct      240
```

-continued

```
tcgagcctca tataagtata agtagttcaa cgtattagca ctgtacccag catctccgta    300
tcgagaaaca caacaacatg ccccattgga cagatcatgc ggatacacag gttgtgcagt    360
atcatacata ctcgatcaga caggtcgtct gaccatcata caagctgaac aagcgctcca    420
tacttgcacg ctctctatat acacagttaa attacatatc catagtctaa cctctaacag    480
ttaatcttct ggtaagcctc ccagccagcc ttctggtatc gcttggcctc ctcaatagga    540
tctcggttct ggccgtacag acctcggccg acaattatga tatccgttcc ggtagacatg    600
acatcctcaa cagttcggta ctgctgtccg agagcgtctc ccttgtcgtc aagacccacc    660
ccgggggtca gaataagcca gtcctcagag tcgcccttag gtcggttctg ggcaatgaag    720
ccaaccacaa actcggggtc ggatcgggca agctcaatgg tctgcttgga gtactcgcca    780
gtggccagag agcccttgca agacagctcg gccagcatga gcagacctct ggccagcttc    840
tcgttgggag aggggactag gaactccttg tactgggagt tctcgtagtc agagacgtcc    900
tccttcttct gttcagagac agtttcctcg gcaccagctc gcaggccagc aatgattccg    960
gttccgggta caccgtgggc gttggtgata tcggaccact cggcgattcg gtgacaccgg   1020
tactggtgct tgacagtgtt gccaatatct gcgaactttc tgtcctcgaa caggaagaaa   1080
ccgtgcttaa gagcaagttc cttgaggggg agcacagtgc cggcgtaggt gaagtcgtca   1140
atgatgtcga tatgggtttt gatcatgcac acataaggtc cgaccttatc ggcaagctca   1200
atgagctcct tggtggtggt aacatccaga gaagcacaca ggttggtttt cttggctgcc   1260
acgagcttga gcactcgagc ggcaaaggcg gacttgtgga cgttagctcg agcttcgtag   1320
gagggcattt tggtggtgaa gaggagactg aaataaattt agtctgcaga acttttatc    1380 ggaaccttat ctggggcagt gaagtatatg ttatggtaat agttacgagt tagttgaact   1440
tatagataga ctggactata cggctatcgg tccaaattag aaagaacgtc aatggctctc   1500
tgggcgtcgc ctttgccgac aaaaatgtga tcatgatgaa agccagcaat gacgttgcag   1560
ctgatattgt tgtcggccaa ccgcgccgaa aacgcagctg tcagacccac agcctccaac   1620
gaagaatgta tcgtcaaagt gatccaagca cactcatagt tggagtcgta ctccaaaggc   1680
ggcaatgacg agtcagacag atactcgtcg acctcgaggg ggggcccggt acccaattcg   1740
ccctatagtg agtcgtatta cgcgcgctca ctggccgtcg ttttacaacg tcgtgactgg   1800
gaaaaccctg gcgttaccca acttaatcgc cttgcagcac atcccccttt cgccagctgg   1860
cgtaatagcg aagaggcccg caccgatcgc ccttcccaac agttgcgcag cctgaatggc   1920
gaatggaaat tgtaagcgtt aatattttgt taaaattcgc gttaaatttt tgttaaatca   1980
gctcattttt taaccaatag gccgaaatcg gcaaaatccc ttataaatca aaagaataga   2040
ccgagatagg gttgagtgtt gttccagttt ggaacaagag tccactatta agaacgtgg    2100 actccaacgt caaagggcga aaaccgtct atcagggcga tggcccacta cgtgaaccat    2160 cacctaatc aagttttttg gggtcgaggt gccgtaaagc actaaatcgg aaccctaaag    2220 ggagccccg atttagagct tgacggggaa agccggcgaa cgtggcgaga aggaaggga    2280 agaaagcgaa aggagcgggc gctagggcgc tggcaagtgt agcggtcacg ctgcgcgtaa   2340
ccaccacacc cgccgcgctt aatgcgccgc tacagggcgc gtcaggtggc acttttcggg   2400
gaaatgtgcg cggaaccct atttgtttat ttttctaaat acattcaaat atgtatccgc    2460
tcatgagaca ataaccctga taaatgcttc aataatattg aaaaaggaag agtatgagta   2520
ttcaacattt ccgtgtcgcc cttattccct ttttttgcggc attttgcctt cctgtttttg   2580
```

```
ctcacccaga aacgctggtg aaagtaaaag atgctgaaga tcagttgggt gcacgagtgg    2640
gttacatcga actggatctc aacagcggta agatccttga gagttttcgc cccgaagaac    2700
gttttccaat gatgagcact tttaaagttc tgctatgtgg cgcggtatta tcccgtattg    2760
acgccgggca agagcaactc ggtcgccgca tacactattc tcagaatgac ttggttgagt    2820
actcaccagt cacagaaaag catcttacgg atggcatgac agtaagagaa ttatgcagtg    2880
ctgccataac catgagtgat aacactgcgg ccaacttact tctgacaacg atcgaggac    2940 cgaaggagct aaccgctttt ttgcacaaca tgggggatca tgtaactcgc cttgatcgtt    3000
gggaaccgga gctgaatgaa gccataccaa acgacgagcg tgacaccacg atgcctgtag    3060
caatggcaac aacgttgcgc aaactattaa ctggcgaact acttactcta gcttcccggc    3120
aacaattaat agactggatg gaggcggata aagttgcagg accacttctg cgctcggccc    3180
ttccggctgg ctggtttatt gctgataaat ctggagccgg tgagcgtggg tctcgcggta    3240
tcattgcagc actggggcca gatggtaagc cctcccgtat cgtagttatc tacacgacgg    3300
ggagtcaggc aactatggat gaacgaaata gacagatcgc tgagataggt gcctcactga    3360
ttaagcattg gtaactgtca gaccaagttt actcatatat actttagatt gatttaaaac    3420
ttcattttta atttaaaagg atctaggtga agatccttt tgataatctc atgaccaaaa    3480
tcccttaacg tgagttttcg ttccactgag cgtcagaccc cgtagaaaag atcaaaggat    3540
cttcttgaga tccttttttt ctgcgcgtaa tctgctgctt gcaaacaaaa aaaccaccgc    3600
taccagcggt ggtttgtttg ccggatcaag agctaccaac tctttttccg aaggtaactg    3660
gcttcagcag agcgcagata ccaaatactg tccttctagt gtagccgtag ttaggccacc    3720
acttcaagaa ctctgtagca ccgcctacat acctcgctct gctaatcctg ttaccagtgg    3780
ctgctgccag tggcgataag tcgtgtctta ccgggttgga ctcaagacga tagttaccgg    3840
ataaggcgca gcggtcgggc tgaacggggg gttcgtgcac acagcccagc ttggagcgaa    3900
cgacctacac cgaactgaga tacctacagc gtgagctatg agaaagcgcc acgcttcccg    3960
aagggagaaa ggcggacagg tatccggtaa gcggcagggt cggaacagga gagcgcacga    4020
gggagcttcc agggggaaac gcctggtatc tttatagtcc tgtcgggttt cgccacctct    4080
gacttgagcg tcgatttttg tgatgctcgt caggggggcg gagcctatgg aaaaacgcca    4140
gcaacgcggc cttttttacgg ttcctggcct tttgctggcc ttttgctcac atgttctttc    4200
ctgcgttatc ccctgattct gtggataacc gtattaccgc ctttgagtga gctgataccg    4260
ctcgccgcag ccgaacgacc gagcgcagcg agtcagtgag cgaggaagcg gaagagcgcc    4320
caatacgcaa accgcctctc cccgcgcgtt ggccgattca ttaatgcagc tggcacgaca    4380
ggtttcccga ctggaaagcg ggcagtgagc gcaacgcaat taatgtgagt tagctcactc    4440
attaggcacc ccaggcttta cactttatgc ttccggctcg tatgttgtgt ggaattgtga    4500
gcggataaca atttcacaca ggaaacagct atgaccatga ttacgccaag cgcgcaatta    4560
accctcacta aagggaacaa aagctggagc tccaccgcgg tggc                    4604
```

<210> SEQ ID NO 15
<211> LENGTH: 6728
<212> TYPE: DNA
<213> ORGANISM: Artificial sequence
<220> FEATURE:
<223> OTHER INFORMATION: Plasmid construct pME-KO

<400> SEQUENCE: 15

```
aattccttta cctgcaggat aacttcgtat aatgtatgct atacgaagtt atgatctctc      60
```

```
tcttgagctt ttccataaca agttcttctg cctccaggaa gtccatgggt ggtttgatca     120
tggttttggt gtagtggtag tgcagtggtg gtattgtgac tggggatgta gttgagaata     180
agtcatacac aagtcagctt tcttcgagcc tcatataagt ataagtagtt caacgtatta     240
gcactgtacc cagcatctcc gtatcgagaa acacaacaac atgccccatt ggacagatca     300
tgcggataca caggttgtgc agtatcatac atactcgatc agacaggtcg tctgaccatc     360
atacaagctg aacaagcgct ccatacttgc acgctctcta tatacacagt taaattacat     420
atccatagtc taacctctaa cagttaatct tctggtaagc ctcccagcca gccttctggt     480
atcgcttggc ctcctcaata ggatctcggt tctggccgta cagacctcgg ccgacaatta     540
tgatatccgt tccggtagac atgacatcct caacagttcg gtactgctgt ccgagagcgt     600
ctcccttgtc gtcaagaccc accccggggg tcagaataag ccagtcctca gagtcgccct     660
taggtcggtt ctgggcaatg aagccaacca caaactcggg gtcggatcgg caagctcaa      720 tggtctgctt ggagtactcg ccagtggcca gagagccctt gcaagacagc tcggccagca     780
tgagcagacc tctggccagc ttctcgttgg gagagggac taggaactcc ttgtactggg      840
agttctcgta gtcagagacg tcctccttct tctgttcaga dacagtttcc tcggcaccag     900
ctcgcaggcc agcaatgatt ccggttccgg gtacaccgtg ggcgttggtg atatcggacc     960
actcggcgat tcggtgacac cggtactggt gcttgacagt gttgccaata tctgcgaact    1020
ttctgtcctc gaacaggaag aaaccgtgct taagagcaag ttccttgagg gggagcacag    1080
tgccggcgta ggtgaagtcg tcaatgatgt cgatatgggt tttgatcatg cacacataag    1140
gtccgacctt atcggcaagc tcaatgagct ccttggtggt ggtaacatcc agagaagcac    1200
acaggttggt tttcttggct gccacgagct tgagcactcg agcggcaaag gcggacttgt    1260
ggacgttagc tcgagcttcg taggagggca ttttggtggt gaagaggaga ctgaaataaa    1320
tttagtctgc agaactttttt atcggaacct tatctgggc agtgaagtat atgttatggt    1380
aatagttacg agttagttga acttatagat agactggact atacggctat cggtccaaat    1440
tagaagaaac gtcaatggct ctctgggcgt cgcctttgcc gacaaaaatg tgatcatgat    1500
gaaagccagc aatgacgttg cagctgatat tgttgtcggc caaccgcgcc gaaaacgcag    1560
ctgtcagacc cacagcctcc aacgaagaat gtatcgtcaa agtgatccaa gcacactcat    1620
agttggagtc gtactccaaa ggcggcaatg acgagtcaga cagatactcg tcgacctcga    1680
gggggggccc ggtacccaat tcgccctata gtgagtcgta ttacgcgcgc tcactggccg    1740
tcgttttaca acgtcgtgac tgggaaaacc ctggcgttac ccaacttaat cgccttgcag    1800
cacatccccc tttcgccagc tggcgtaata gcgaagaggc ccgcaccgat cgcccttccc    1860
aacagttgcg cagcctgaat ggcgaatgga aattgtaagc gttaatattt tgttaaaatt    1920
cgcgttaaat ttttgttaaa tcagctcatt ttttaaccaa taggccgaaa tcggcaaaat    1980
cccttataaa tcaaaagaat agaccgagat agggttgagt gttgttccag tttggaacaa    2040
gagtccacta ttaaagaacg tggactccaa cgtcaaaggg cgaaaaaccg tctatcaggg    2100
cgatggccca ctacgtgaac catcacccta atcaagtttt tggggtcga ggtgccgtaa      2160 agcactaaat cggaacccta aagggagccc ccgatttaga gcttgacggg gaaagccggc    2220
gaacgtggcg agaaaggaag ggaagaaagc gaaaggagcg ggcgctaggg cgctggcaag    2280
tgtagcggtc acgctgcgcg taaccaccac acccgccgcg cttaatgcgc cgctacaggg    2340
cgcgtcaggt ggcacttttc ggggaaatgt gcgcggaacc cctatttgtt tattttcta     2400
```

```
aatacattca aatatgtatc cgctcatgag acaataaccc tgataaatgc ttcaataata  2460
ttgaaaaagg aagagtatga gtattcaaca tttccgtgtc gcccttattc ccttttttgc  2520
ggcattttgc cttcctgttt ttgctcaccc agaaacgctg gtgaaagtaa aagatgctga  2580
agatcagttg ggtgcacgag tgggttacat cgaactggat ctcaacagcg gtaagatcct  2640
tgagagtttt cgccccgaag aacgttttcc aatgatgagc acttttaaag ttctgctatg  2700
tggcgcggta ttatcccgta ttgacgccgg gcaagagcaa ctcggtcgcc gcatacacta  2760
ttctcagaat gacttggttg agtactcacc agtcacagaa aagcatctta cggatggcat  2820
gacagtaaga gaattatgca gtgctgccat aaccatgagt gataacactg cggccaactt  2880
acttctgaca acgatcggag gaccgaagga gctaaccgct tttttgcaca catgggggga  2940
tcatgtaact cgccttgatc gttgggaacc ggagctgaat gaagccatac caaacgacga  3000
gcgtgacacc acgatgcctg tagcaatggc aacaacgttg cgcaaactat taactggcga  3060
actacttact ctagcttccc ggcaacaatt aatagactgg atggaggcgg ataaagttgc  3120
aggaccactt ctgcgctcgg cccttccggc tggctggttt attgctgata atctggagcc  3180
cggtgagcgt gggtctcgcg gtatcattgc agcactgggg ccagatggta agccctcccg  3240
tatcgtagtt atctacacga cggggagtca ggcaactatg gatgaacgaa atagacagat  3300
cgctgagata ggtgcctcac tgattaagca ttggtaactg tcagaccaag tttactcata  3360
tatactttag attgatttaa aacttcattt ttaatttaaa aggatctagg tgaagatcct  3420
ttttgataat ctcatgacca aaatccctta acgtgagttt tcgttccact gagcgtcaga  3480
ccccgtagaa aagatcaaag gatcttcttg agatcctttt ttctgcgcg taatctgctg  3540
cttgcaaaca aaaaaaccac cgctaccagc ggtggtttgt ttgccggatc aagagctacc  3600
aactcttttt ccgaaggtaa ctggcttcag cagagcgcag ataccaaata ctgtccttct  3660
agtgtagccg tagttaggcc accacttcaa gaactctgta gcaccgccta catacctcgc  3720
tctgctaatc ctgttaccag tggctgctgc cagtggcgat aagtcgtgtc ttaccgggtt  3780
ggactcaaga cgatagttac cggataaggc gcagcggtcg ggctgaacgg ggggttcgtg  3840
cacacagccc agcttggagc gaacgaccta caccgaactg agatacctac agcgtgagct  3900
atgagaaagc gccacgcttc ccgaagggag aaaggcggac aggtatccgg taagcggcag  3960
ggtcggaaca ggagagcgca cgagggagct tccaggggga aacgcctggt atctttatag  4020
tcctgtcggg tttcgccacc tctgacttga gcgtcgattt ttgtgatgct cgtcaggggg  4080
gcggagccta tggaaaaacg ccagcaacgc ggcctttttta cggttcctgg ccttttgctg  4140
gccttttgct cacatgttct ttcctgcgtt atcccctgat tctgtggata accgtattac  4200
cgcctttgag tgagctgata ccgctcgccg cagccgaacg accgagcgca gcgagtcagt  4260
gagcgaggaa gcggaagagc gcccaatacg caaaccgcct ctccccgcgc gttggccgat  4320
tcattaatgc agctggcacg acaggtttcc cgactggaaa gcgggcagtg agcgcaacgc  4380
aattaatgtg agttagctca ctcattaggc accccaggct ttacacttta tgcttccggc  4440
tcgtatgttg tgtggaattg tgagcggata acaatttcac acaggaaaca gctatgacca  4500
tgattacgcc aagcgcgcaa ttaaccctca ctaaagggaa caaaagctgg agctccaccg  4560
cggtggcggc cgctctagaa ctagtggatc cgtgcccacg tttcgtttct tcaccggcgg  4620
cacatccacg cggtcctccg gcccgccgcg ggcctcccct agcttctgtg cttcctcgtc  4680
gcgcttcatc tggtgaaaac gggggttttt gacactcgat ttttcgacac tcgatttttc  4740
gacacttgat ttttcagcga acccagatta tgcgctacac cagcgcctgc atatgcggcg  4800
```

```
ttagtgggga agtggagtag ttggagccgt gtatgatact agagtggcgc tgagggcgcg   4860
tttggtggtc gttccggttg ccctatgaga ctgaacctgg tttcgacagg tgttttgcac   4920
tcattcgcct acctctcgct tatcaccgat ttatgtttca tttcattgga ctattgttag   4980
tttttccgcc aaaactcaaa atgttttctg acatctgact agaacacggc tcctgtcaat   5040
gagcaaggat tgagtgtcta caagtgcaag gagtggtagt gttcaatggc ttttggtcta   5100
gaaccagatg agcatgaaaa aaggaacgtg agtttcctga tattcccgcc gctaatcatt   5160
ctgtctctct tacccaccca aagcgtccct ccgatgacat ttccatacga gtgcttacta   5220
aactaaactg tcactggcgc cgataataca ttcatctacc agtactacta tcaactactg   5280
tcgactacta tggtccgcca ctggactcca atggactctc caatggactc ttcaatggac   5340
tcctatggac tcttctcgga ctcactctga tcaacgctgt gttatcaagc tgtattccac   5400
tattccacgc tctagtcgta atcccgcaca tggatgagag gccggtagac gggccgccac   5460
atctgagtct cgacccaggc gagacactcg tcaaagttgt cgggaatctg cacatgttcc   5520
ttggtgccgg gcttgagctc ttcctcgaca gtggctaggc cctcagcctt ggcctgaaga   5580
accacggcag tggccacccg ggccgaaatg atctggatga gagctacgtc gggaagtact   5640
ccctcgtcgt ggttcttgag aatgggggcc tgttcggcga ggcactcgat ggcagcagca   5700
atcatggtgt tggtgatgag cttttgatcga gacagaatgc tcgaggacgt aggacgagta   5760
ttcgaagctg gaggggctgg aggaggacat gtttcgggcc gcggcggtgg gcccaagcgc   5820
cgccctgacg ctggtctgtg tgggtcgcat ggttcgtagt cgtaacatgg cgaatatcag   5880
cgtgtacagg agtacttgta tactggaagc agtatcttgg caggaattta aatcgccccc   5940
ttaagagttc gacaacactc acaacctctc aacctagatt ggctatcaac cttgcgggat   6000
tatgcagcgc gacagggagc ataaacgggg tgttatgggg gctgaaaacg gctggaaaag   6060
acataaatcg gacaattggc ggccagaaaa tgttgcgggg aaaaaaccgc ccgaaaacc    6120 gccctgctcg tccaattgac cgcatcttct gtccccactg acgccttcca tcctgcaggc   6180
caagacaacg acatgcacgc acgtggaaca ggcagaccta aaatgagggt tgtaggatat   6240
taaagctagt gatttacgac caagaaacat gtagagtacg agtatagtac gtagaacaat   6300
gatgctccaa atagagagaa gatggcatgt cacttggtac ggccatggaa tgcacgcatt   6360
tcctcaatat ggttagtttt taacattgac agcactagtc atgcaccata tcatatcagc   6420
ccacatggtg agacacacat cgcatgcaca ggtcaggttc tgggaggtga tgaataaata   6480
ataatacaat aaataagaaa aatgcaacta aatgaatctg cgctggattt cctccaaatc   6540 ccctgtagc tccttatgtc gtttgatgtt gcgagaaaca atgttcttga tgctcaaggt    6600
cagctcgtgc tcatgaccct ggtagaagcc gccaagctcg gaggccaagg tgatctgggc   6660
gttcttggtc tccatcgaca gtcgtctgat ttcgttctcc gtgatgtgga tacggttttt   6720
gatcagcg                                                            6728
```

<210> SEQ ID NO 16
<211> LENGTH: 34
<212> TYPE: DNA
<213> ORGANISM: Artificial sequence
<220> FEATURE:
<223> OTHER INFORMATION: Primer YME-5-1

<400> SEQUENCE: 16
gatcaagaat tcgctgatca aaaccgtat ccac                                 34

<210> SEQ ID NO 17
<211> LENGTH: 34
<212> TYPE: DNA
<213> ORGANISM: Artificial sequence
<220> FEATURE:
<223> OTHER INFORMATION: Primer YME-5-2

<400> SEQUENCE: 17
gatcaactcg aggacgtagg acgagtattc gaag                          34

<210> SEQ ID NO 18
<211> LENGTH: 34
<212> TYPE: DNA
<213> ORGANISM: Artificial sequence
<220> FEATURE:
<223> OTHER INFORMATION: Primer YME-3-1

<400> SEQUENCE: 18
gatcaactcg agcattctgt ctcgatcaaa gctc                          34

<210> SEQ ID NO 19
<211> LENGTH: 35
<212> TYPE: DNA
<213> ORGANISM: Artificial sequence
<220> FEATURE:
<223> OTHER INFORMATION: Primer YME-3-2

<400> SEQUENCE: 19
gatcaaggat ccgtgcccac gtttcgtttc ttcac                         35

<210> SEQ ID NO 20
<211> LENGTH: 23
<212> TYPE: DNA
<213> ORGANISM: Artificial sequence
<220> FEATURE:
<223> OTHER INFORMATION: Primer YME-5-confirm-1

<400> SEQUENCE: 20
ctcaaatctc gcatttgaga ctc                                      23

<210> SEQ ID NO 21
<211> LENGTH: 21
<212> TYPE: DNA
<213> ORGANISM: Artificial sequence
<220> FEATURE:
<223> OTHER INFORMATION: Primer YME-5-confirm-2

<400> SEQUENCE: 21
gcagcagcaa tcatggtgtt g                                        21

<210> SEQ ID NO 22
<211> LENGTH: 22
<212> TYPE: DNA
<213> ORGANISM: Artificial sequence
<220> FEATURE:
<223> OTHER INFORMATION: Primer YME-3-confirm-1

<400> SEQUENCE: 22
gagtgttgtc gaactcttaa gg                                       22

<210> SEQ ID NO 23
<211> LENGTH: 22
<212> TYPE: DNA
<213> ORGANISM: Artificial sequence
<220> FEATURE:
<223> OTHER INFORMATION: Primer YME-3-confirm-2

<400> SEQUENCE: 23
gttgtgttga gcacgtggca tc                                                  22

<210> SEQ ID NO 24
<211> LENGTH: 1017
<212> TYPE: DNA
<213> ORGANISM: Yarrowia lipolytica

<400> SEQUENCE: 24
atgttccgaa cccgagttac cggctccacc ctgcgatcct tctccacctc cgctgcccga     60
cagcacaagg ttgtcgtcct tggcgccaac ggaggcattg ccagcccct gtctctgctg     120
ctcaagctca caagaacgt gaccgacctc ggtctgtacg atctgcgagg cgcccccggc     180
gttgctgccg atgtctccca catccccacc aactccaccg tggccggcta ctctcccgac     240
aacaacggca ttgccgaggc cctcaagggc gccaagctgg tgctgatccc cgccggtgtc     300
ccccgaaagc ccggcatgac ccgagacgat ctgttcaaca ccaacgcctc cattgtgcga     360
gacctggcca aggccgtcgg tgagcacgcc cccgacgcct tgtcggagt cattgctaac     420
cccgtcaact ccaccgtccc cattgtcgcc gaggtgctca gtccaaggg caagtacgac     480
cccaagaagc tcttcggtgt caccaccctc gacgtcatcc gagccgagcg attcgtctcc     540
cagctcgagc acaccaaccc caccaaggag tacttccccg ttgttggcgg ccactccggt     600
gtcaccattg tccccctcgt gtcccagtcc gaccaccccg acattgccgg tgaggctcga     660
gacaagcttg tccaccgaat ccagtttggc ggtgacgagg ttgtcaaggc caaggacggt     720
gccggatccg ccaccctttc catggcccag gctgccgccc gattcgccga ctctctcctc     780
cgaggtgtca acggcgagaa ggacgttgtt gagcccactt cgtcgactc tcctctgttc     840
aagggtgagg gcatcgactt cttctccacc aaggtcactc ttggccctaa cggtgttgag     900
gagatccacc ccatcggaaa ggtcaacgag tacgaggaga agctcatcga ggctgccaag     960
gccgatctca agaagaacat tgagaagggt gtcaactttg tcaagcagaa cccttaa       1017

<210> SEQ ID NO 25
<211> LENGTH: 338
<212> TYPE: PRT
<213> ORGANISM: Yarrowia lipolytica

<400> SEQUENCE: 25

Met Phe Arg Thr Arg Val Thr Gly Ser Thr Leu Arg Ser Phe Ser Thr
1               5                   10                  15

Ser Ala Ala Arg Gln His Lys Val Val Leu Gly Ala Asn Gly Gly
            20                  25                  30

Ile Gly Gln Pro Leu Ser Leu Leu Leu Lys Leu Asn Lys Asn Val Thr
        35                  40                  45

Asp Leu Gly Leu Tyr Asp Leu Arg Gly Ala Pro Gly Val Ala Ala Asp
    50                  55                  60

Val Ser His Ile Pro Thr Asn Ser Thr Val Ala Gly Tyr Ser Pro Asp
65                  70                  75                  80

Asn Asn Gly Ile Ala Glu Ala Leu Lys Gly Ala Lys Leu Val Leu Ile
                85                  90                  95

Pro Ala Gly Val Pro Arg Lys Pro Gly Met Thr Arg Asp Asp Leu Phe
            100                 105                 110

Asn Thr Asn Ala Ser Ile Val Arg Asp Leu Ala Lys Ala Val Gly Glu
        115                 120                 125

His Ala Pro Asp Ala Phe Val Gly Val Ile Ala Asn Pro Val Asn Ser
    130                 135                 140

Thr Val Pro Ile Val Ala Glu Val Leu Lys Ser Lys Gly Lys Tyr Asp
145                 150                 155                 160

Pro Lys Lys Leu Phe Gly Val Thr Thr Leu Asp Val Ile Arg Ala Glu
                165                 170                 175

Arg Phe Val Ser Gln Leu Glu His Thr Asn Pro Thr Lys Glu Tyr Phe
            180                 185                 190

Pro Val Gly Gly His Ser Gly Val Thr Ile Val Pro Leu Val Ser
            195                 200                 205

Gln Ser Asp His Pro Asp Ile Ala Gly Glu Ala Arg Asp Lys Leu Val
    210                 215                 220

His Arg Ile Gln Phe Gly Gly Asp Glu Val Val Lys Ala Lys Asp Gly
225                 230                 235                 240

Ala Gly Ser Ala Thr Leu Ser Met Ala Gln Ala Ala Arg Phe Ala
                245                 250                 255

Asp Ser Leu Leu Arg Gly Val Asn Gly Glu Lys Asp Val Val Glu Pro
            260                 265                 270

Thr Phe Val Asp Ser Pro Leu Phe Lys Gly Glu Gly Ile Asp Phe Phe
    275                 280                 285

Ser Thr Lys Val Thr Leu Gly Pro Asn Gly Val Glu Glu Ile His Pro
290                 295                 300

Ile Gly Lys Val Asn Glu Tyr Glu Glu Lys Leu Ile Glu Ala Ala Lys
305                 310                 315                 320

Ala Asp Leu Lys Lys Asn Ile Glu Lys Gly Val Asn Phe Val Lys Gln
                325                 330                 335

Asn Pro

<210> SEQ ID NO 26
<211> LENGTH: 996
<212> TYPE: DNA
<213> ORGANISM: Yarrowia lipolytica

<400> SEQUENCE: 26
atggttaaag ctgtcgttgc cggagccgct ggtggtattg ccagcccct ttctcttctc      60 ctcaaactct ctccttacgt gaccgagctt gctctctacg atgtcgtcaa ctcccccggt    120
gttgccgctg acctctccca catctccacc aaggctaagg tcactggcta cctccccaag    180
gatgacggtc tcaagaacgc tctgaccggc gccaacattg tcgttatccc cgccggtatc    240
cccgaaaagc ccgtatgac ccgagacgat ctgttcaaga tcaacgctgg tatcgtccga    300
gatctcgtca ccggtgtcgc ccagtacgcc cctgacgcct tgtgctcat catctccaac    360 cccgtcaact ctaccgtccc tattgctgcc gaggtcctca gaagcacaa cgtcttcaac    420 cctaagaagc tcttcggtgt caccaccctt gacgttgtcc gagcccagac cttcaccgcc    480
gctgttgttg gcgagtctga ccccaccaag ctcaacatcc ccgtcgttgg tggccactcc    540
ggagacacca ttgtccctct cctgtctctg accaagccta aggtcgagat cccgccgac    600 aagctcgacg acctcgtcaa gcgaatccag tttggtggtg acgaggttgt ccaggctaag    660
gacggtcttg gatccgctac cctctccatg gcccaggctg tttccgatt tgccgaggct    720 gtcctcaagg gtgccgctgg tgagaagggc atcatcgagc cgcctacat ctaccttgac    780 ggtattgatg gcacctccga catcaagcga gaggtcggtg tcgccttctt ctctgtccct    840
gtcgagttcg gccctgaggg tgccgctaag gcttacaaca tccttcccga ggccaacgac    900

```
tacgagaaga agcttctcaa ggtctccatc gacggtcttt acggcaacat tgccaagggc    960
gaggagttca ttgttaaccc tcctcctgcc aactag                              996
```

<210> SEQ ID NO 27
<211> LENGTH: 331
<212> TYPE: PRT
<213> ORGANISM: Yarrowia lipolytica

<400> SEQUENCE: 27

```
Met Val Lys Ala Val Val Ala Gly Ala Ala Gly Gly Ile Gly Gln Pro
1               5                   10                  15

Leu Ser Leu Leu Leu Lys Leu Ser Pro Tyr Val Thr Glu Leu Ala Leu
            20                  25                  30

Tyr Asp Val Val Asn Ser Pro Gly Val Ala Ala Asp Leu Ser His Ile
        35                  40                  45

Ser Thr Lys Ala Lys Val Thr Gly Tyr Leu Pro Lys Asp Asp Gly Leu
    50                  55                  60

Lys Asn Ala Leu Thr Gly Ala Asn Ile Val Val Ile Pro Ala Gly Ile
65                  70                  75                  80

Pro Arg Lys Pro Gly Met Thr Arg Asp Asp Leu Phe Lys Ile Asn Ala
                85                  90                  95

Gly Ile Val Arg Asp Leu Val Thr Gly Val Ala Gln Tyr Ala Pro Asp
            100                 105                 110

Ala Phe Val Leu Ile Ile Ser Asn Pro Val Asn Ser Thr Val Pro Ile
        115                 120                 125

Ala Ala Glu Val Leu Lys Lys His Asn Val Phe Asn Pro Lys Lys Leu
    130                 135                 140

Phe Gly Val Thr Thr Leu Asp Val Val Arg Ala Gln Thr Phe Thr Ala
145                 150                 155                 160

Ala Val Val Gly Glu Ser Asp Pro Thr Lys Leu Asn Ile Pro Val Val
                165                 170                 175

Gly Gly His Ser Gly Asp Thr Ile Val Pro Leu Leu Ser Leu Thr Lys
            180                 185                 190

Pro Lys Val Glu Ile Pro Ala Asp Lys Leu Asp Asp Leu Val Lys Arg
        195                 200                 205

Ile Gln Phe Gly Gly Asp Glu Val Val Gln Ala Lys Asp Gly Leu Gly
    210                 215                 220

Ser Ala Thr Leu Ser Met Ala Gln Ala Gly Phe Arg Phe Ala Glu Ala
225                 230                 235                 240

Val Leu Lys Gly Ala Ala Gly Glu Lys Gly Ile Ile Glu Pro Ala Tyr
                245                 250                 255

Ile Tyr Leu Asp Gly Ile Asp Gly Thr Ser Asp Ile Lys Arg Glu Val
            260                 265                 270

Gly Val Ala Phe Phe Ser Val Pro Val Glu Phe Gly Pro Glu Gly Ala
        275                 280                 285

Ala Lys Ala Tyr Asn Ile Leu Pro Glu Ala Asn Asp Tyr Glu Lys Lys
    290                 295                 300

Leu Leu Lys Val Ser Ile Asp Gly Leu Tyr Gly Asn Ile Ala Lys Gly
305                 310                 315                 320

Glu Glu Phe Ile Val Asn Pro Pro Ala Asn
                325                 330
```

<210> SEQ ID NO 28
<211> LENGTH: 999
<212> TYPE: DNA

<213> ORGANISM: Yarrowia lipolytica

<400> SEQUENCE: 28

```
atggttaaag ctgtcgttgc cggagccgct ggtggtattg gccagcccct ttctcttctc    60
ctcaaactct ctccttacgt gaccgagctt gctctctacg atgtcgtcaa ctcccccggt   120
gttgccgctg acctctccca catctccacc aaggctaagg tcactggcta cctccccaag   180
gatgacggtc tcaagaacgc tctgaccggc gccaacattg tcgttatccc cgccggtatc   240
ccccgaaagc ccggtatgac ccgagacgat ctgttcaaga tcaacgctgg tatcgtccga   300
gatctcgtca ccggtgtcgc ccagtacgcc cctgacgcct tgtgctcat catctccaac    360
cccgtcaact ctaccgtccc tattgctgcc gaggtcctca agaagcacaa cgtcttcaac   420
cctaagaagc tcttcggtgt caccacccct gacgttgtcc gagcccagac cttcaccgcc   480
gctgttgttg gcgagtctga ccccaccaag ctcaacatcc ccgtcgttgg tggccactcc   540
ggagacacca ttgtccctct cctgtctctg accaagccta aggtcgagat ccccgccgac   600
aagctcgacg acctcgtcaa gcgaatccag tttggtggtg acgaggttgt ccaggctaag   660
gacggtcttg gatccgctac cctctccatg gcccaggctg gtttccgatt tgccgaggct   720
gtcctcaagg gtgccgctgg tgagaagggc atcatcgagc ccgcctacat ctaccttgac   780
ggtattgatg caccctccga catcaagcga gaggtcggtg tcgccttctt ctctgtccct   840
gtcgagttcg cccctgaggg tgccgctaag gcttacaaca tccttcccga ggccaacgac   900
tacgagaaga gcttctcaa ggtctccatc gacggtcttt acggcaacat gccaagggc    960
gaggagttca ttgttaaccc tcctcctgcc aagatctaa                          999
```

<210> SEQ ID NO 29
<211> LENGTH: 332
<212> TYPE: PRT
<213> ORGANISM: Yarrowia lipolytica

<400> SEQUENCE: 29

```
Met Val Lys Ala Val Val Ala Gly Ala Ala Gly Gly Ile Gly Gln Pro
 1               5                  10                  15

Leu Ser Leu Leu Lys Leu Ser Pro Tyr Val Thr Glu Leu Ala Leu
            20                  25                  30

Tyr Asp Val Val Asn Ser Pro Gly Val Ala Ala Asp Leu Ser His Ile
        35                  40                  45

Ser Thr Lys Ala Lys Val Thr Gly Tyr Leu Pro Lys Asp Asp Gly Leu
    50                  55                  60

Lys Asn Ala Leu Thr Gly Ala Asn Ile Val Val Ile Pro Ala Gly Ile
65                  70                  75                  80

Pro Arg Lys Pro Gly Met Thr Arg Asp Asp Leu Phe Lys Ile Asn Ala
                85                  90                  95

Gly Ile Val Arg Asp Leu Val Thr Gly Val Ala Gln Tyr Ala Pro Asp
            100                 105                 110

Ala Phe Val Leu Ile Ile Ser Asn Pro Val Asn Ser Thr Val Pro Ile
        115                 120                 125

Ala Ala Glu Val Leu Lys Lys His Asn Val Phe Asn Pro Lys Lys Leu
    130                 135                 140

Phe Gly Val Thr Thr Leu Asp Val Val Arg Ala Gln Thr Phe Thr Ala
145                 150                 155                 160

Ala Val Val Gly Glu Ser Asp Pro Thr Lys Leu Asn Ile Pro Val Val
                165                 170                 175
```

-continued

```
Gly Gly His Ser Gly Asp Thr Ile Val Pro Leu Leu Ser Leu Thr Lys
            180                 185                 190

Pro Lys Val Glu Ile Pro Ala Asp Lys Leu Asp Asp Leu Val Lys Arg
        195                 200                 205

Ile Gln Phe Gly Gly Asp Glu Val Val Gln Ala Lys Asp Gly Leu Gly
    210                 215                 220

Ser Ala Thr Leu Ser Met Ala Gln Ala Gly Phe Arg Phe Ala Glu Ala
225                 230                 235                 240

Val Leu Lys Gly Ala Gly Glu Lys Gly Ile Ile Glu Pro Ala Tyr
                245                 250                 255

Ile Tyr Leu Asp Gly Ile Asp Gly Thr Ser Asp Ile Lys Arg Glu Val
        260                 265                 270

Gly Val Ala Phe Phe Ser Val Pro Val Glu Phe Gly Pro Glu Gly Ala
    275                 280                 285

Ala Lys Ala Tyr Asn Ile Leu Pro Glu Ala Asn Asp Tyr Glu Lys Lys
        290                 295                 300

Leu Leu Lys Val Ser Ile Asp Gly Leu Tyr Gly Asn Ile Ala Lys Gly
305                 310                 315                 320

Glu Glu Phe Ile Val Asn Pro Pro Ala Lys Ile
                325                 330
```

<210> SEQ ID NO 30
<211> LENGTH: 338
<212> TYPE: PRT
<213> ORGANISM: Yarrowia lipolytica

<400> SEQUENCE: 30

```
Met Val Arg Thr Arg Val Thr Gly Ser Thr Leu Arg Ser Phe Ser Thr
1               5                   10                  15

Ser Ala Ala Arg Gln His Lys Val Val Leu Gly Ala Asn Gly Gly
            20                  25                  30

Ile Gly Gln Pro Leu Ser Leu Leu Leu Lys Leu Asn Lys Asn Val Thr
        35                  40                  45

Asp Leu Gly Leu Tyr Asp Leu Arg Gly Ala Pro Gly Val Ala Ala Asp
    50                  55                  60

Val Ser His Ile Pro Thr Asn Ser Thr Val Ala Gly Tyr Ser Pro Asp
65                  70                  75                  80

Asn Asn Gly Ile Ala Glu Ala Leu Lys Gly Ala Lys Leu Val Leu Ile
                85                  90                  95

Pro Ala Gly Val Pro Arg Lys Pro Gly Met Thr Arg Asp Asp Leu Phe
            100                 105                 110

Asn Thr Asn Ala Ser Ile Val Arg Asp Leu Ala Lys Ala Val Gly Glu
        115                 120                 125

His Ala Pro Asp Ala Phe Gly Val Ile Ala Asn Pro Val Asn Ser
    130                 135                 140

Thr Val Pro Ile Val Ala Glu Val Leu Lys Ser Lys Gly Lys Tyr Asp
145                 150                 155                 160

Pro Lys Lys Leu Phe Gly Val Thr Thr Leu Asp Val Ile Arg Ala Glu
                165                 170                 175

Arg Phe Val Ser Gln Leu Glu His Thr Asn Pro Thr Lys Glu Tyr Phe
            180                 185                 190

Pro Val Val Gly Gly His Ser Gly Val Thr Ile Val Pro Leu Val Ser
        195                 200                 205

Gln Ser Asp His Pro Asp Ile Ala Gly Glu Ala Arg Asp Lys Leu Val
    210                 215                 220
```

```
His Arg Ile Gln Phe Gly Gly Asp Glu Val Val Lys Ala Lys Asp Gly
225                 230                 235                 240

Ala Gly Ser Ala Thr Leu Ser Met Ala Gln Ala Ala Ala Arg Phe Ala
                245                 250                 255

Asp Ser Leu Leu Arg Gly Val Asn Gly Glu Lys Asp Val Val Glu Pro
            260                 265                 270

Thr Phe Val Asp Ser Pro Leu Phe Lys Gly Glu Gly Ile Asp Phe Phe
            275                 280                 285

Ser Thr Lys Val Thr Leu Gly Pro Asn Gly Val Glu Glu Ile His Pro
        290             295                 300

Ile Gly Lys Val Asn Glu Tyr Glu Glu Lys Leu Ile Glu Ala Ala Lys
305             310                 315                 320

Ala Asp Leu Lys Lys Asn Ile Glu Lys Gly Val Asn Phe Val Lys Gln
                325                 330                 335

Asn Pro

<210> SEQ ID NO 31
<211> LENGTH: 32
<212> TYPE: DNA
<213> ORGANISM: Artificial sequence
<220> FEATURE:
<223> OTHER INFORMATION: Primer YMDH1-F

<400> SEQUENCE: 31
gatcaaccat ggtccgaacc cgagttaccg gc                                    32

<210> SEQ ID NO 32
<211> LENGTH: 36
<212> TYPE: DNA
<213> ORGANISM: Artificial sequence
<220> FEATURE:
<223> OTHER INFORMATION: Primer YMDH1-R

<400> SEQUENCE: 32
gatcaagcgg ccgcttaagg gttctgcttg acaaag                                36
```